(12) United States Patent
Dempsey

(10) Patent No.: US 8,883,144 B2
(45) Date of Patent: Nov. 11, 2014

(54) TREATMENT OF PULMONARY VASCULAR REMODELING WITH NEPRILYSIN

(75) Inventor: Edward C. Dempsey, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/224,126

(22) Filed: Sep. 1, 2011

(65) Prior Publication Data
US 2012/0121573 A1    May 17, 2012

Related U.S. Application Data

(60) Provisional application No. 61/379,641, filed on Sep. 2, 2010.

(51) Int. Cl.
| | | |
|---|---|---|
| A61K 38/48 | (2006.01) | |
| A61P 9/00 | (2006.01) | |
| C12Q 1/37 | (2006.01) | |
| G01N 33/573 | (2006.01) | |
| A61K 48/00 | (2006.01) | |

(52) U.S. Cl.
CPC .............. *C12Q 1/37* (2013.01); *A61K 38/4886* (2013.01); *G01N 2333/96419* (2013.01); *G01N 2800/7014* (2013.01); *G01N 2500/10* (2013.01); *A61K 48/005* (2013.01)
USPC ........ 424/94.67; 435/23; 435/6.12; 435/6.13; 435/6.18; 435/7.4; 514/44 R

(58) Field of Classification Search
None
See application file for complete search history.

(56) References Cited

U.S. PATENT DOCUMENTS

| | | | | |
|---|---|---|---|---|
| 2004/0224356 | A1* | 11/2004 | Deleersnijder et al. ........... | 435/6 |
| 2005/0020811 | A1* | 1/2005 | Currie et al. ................... | 530/327 |
| 2011/0021419 | A1* | 1/2011 | Zimmer et al. ................ | 514/4.8 |

OTHER PUBLICATIONS

Carpenter and Stenmark, "Hypoxia decreases lung neprilysin expression and increases pulmonary vascular leak," *Am. J. Physiol. Lung Cell Mol. Physiol.*, 281:L941-948, 2001.
Cohen et al., "Neutral endopeptidase: variable expression in human lung, inactivation in lung cancer, and modulation of peptide-induced calcium flux," *Cancer Res.*, 56:831-839, 1996.
Dempsey et al., "Neprilysin null mice develop exaggerated pulmonary vascular remodeling in response to chronic hypoxia," *Am. J. Pathol.*, 174(3):782-796, 2009.
Dempsey et al., "Recent advances in lung neuro peptide biology using neprilysin and VIP knockout mice," *Drug Discovery Today: Disease Models—Pulmonary Vascular Disease*, 7(3-4):67-75, 2010.
Dusser et al., "Cigarette smoke induces bronchoconstrictor hyperresponsiveness to substance P and inactivates airway neutral endopeptidase in the guinea pig. Possible role of free radicals," *Clin. Invest.*, 84:900-906, 1989.
Gourlet et al., "Vasoactive intestinal peptide (VIP) and pituitary adenylate cyclase-activating peptide (PACAP-27, but not PACAP-38) degradation by the neutral endopeptidase EC 3.4.24.11," *Biochem. Pharmacol.*, 54:509-515, 1997.
Grasemann et al., "Targeted deletion of the neutral endopeptidase gene alters ventilatory responses to acute hypoxia in mice," *J. Appl. Physiol.*, 87:1266-1271, 1999.
Jensen et al., "International Union of Pharmacology. LXVIII. Mammalian bombesin receptors: nomenclature, distribution, pharmacology, signaling, and functions in normal and disease states," *Pharmacol. Rev.*, 60:1-42, 2008.
Jung et al., "CD26/dipeptidylpeptidase IV-targeted therapy of acute lung rejection in rats," *J. Heart Lung Transplant.*, 25:1109-1116, 2006.
Karoor et al., "Neprilysin Regulates PASMC Phenotype and PDGFR Signaling in Mice," *Am. J. Respir. Crit. Care Med.*, American Thoracic Society International Conference Abstracts, 181:A1171, 2010.
Lambeir et al., "Kinetic study of the processing by dipeptidyl-peptidase IV/CD26 of neuropeptides involved in pancreatic insulin secretion," *FEBS. Lett.*, 507:327-330, 2001.
Lee and Channick, "Endothelin antagonism in pulmonary arterial hypertension," *Semin. Respir. Crit. Care Med.*, 26:402-408, 2005.
Lu et al., "Neutral endopeptidase modulates septic shock," *Ann. NY Acad. Sci.*, 780:156-163, 1996.
Lu et al., "The control of microvascular permeability and blood pressure by neutral endopeptidase," *Nat. Med.*, 3:904-907, 1997.
Mentlein, "Dipeptidyl-peptidase IV (CD26)—role in the inactivation of regulatory peptides," *Regul. Pept.*, 85:9-24, 1999.
Mentlein, "Cell-surface peptidases," *Int. Rev. Cytol.*, 235:165-213, 2004.
Papandreou and Nanus, "Is methylation the key to CD10 loss?,"*J. Pediatr. Hematol. Oncol.*, 32:2-3, 2010.
Shinall et al., "Susceptibility of amyloid beta peptide degrading enzymes to oxidative damage: a potential Alzheimer's disease spiral," *Biochemistry*, 44:15345-15350, 2005.
Shipp et al., "Molecular cloning of the common acute lymphoblastic leukemia antigen (CALLA) identifies a type II integral membrane protein," *Proc. Nat'l. Acad. Sci. USA* 85: 4819-4923, 1988.
Sumitomo et al., "Involvement of neutral endopeptidase in neoplastic progression," *Biochim. Biophys. Acta*, 1751:52-59, 2005.
Sunday et al., "CD10/neutral endopeptidase 24.11 in developing human fetal lung. Patterns of expression and modulation of peptide-mediated proliferation," *Clin. Invest.*, 90:2517-2525, 1992.
Thabut et al., "Pulmonary hemodynamics in advanced COPD candidates for lung volume reduction surgery or lung transplantation," *Chest*, 127:1531-1536, 2005.

(Continued)

*Primary Examiner* — Lisa J Hobbs
(74) *Attorney, Agent, or Firm* — Parker Highlander PLLC

(57) ABSTRACT

The present invention relates to agonists of Neprilysin and their use in preventing and treating pulmonary vascular remodeling. Also described are diagnostic and screening applications stemming from the inventor's discovery that Neprilysin is expressed at reduced levels in disease tissues.

15 Claims, 22 Drawing Sheets

(56) References Cited

OTHER PUBLICATIONS van der Velden and Hulsmann, "Peptidases: structure, function and modulation of peptide-mediated effects in the human lung," *Clin. Exp. Allergy*, 29:445-456, 1999.

Weitzenblum et al., "Pulmonary hypertension in chronic obstructive pulmonary disease and interstitial lung diseases," *Semin. Respir. Crit. Care Med.*, 30:458-470, 2009.

Wick et al., "Lung neprilysin activity and expression are decreased in a human model of chronic hypoxic PHTN," *Am. J. Respir. Crit. Care Med.*, 175:A44, 2007.

Wick et al., "Lung neprilysin activity and expression are decreased in humans with COPD and pulmonary vascular remodeling," *FASEB J.*, Meeting Abstract, 23:770, 2009.

Wick et al., "Decreased neprilysin and pulmonary vascular remodeling in chronic obstructive pulmonary disease," *Am. J. Respir. Crit. Care Med.*, Meeting Abstract, 181:A3952, 2010.

* cited by examiner

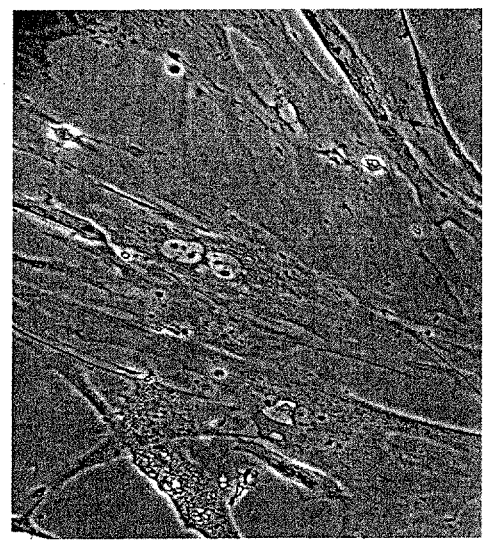
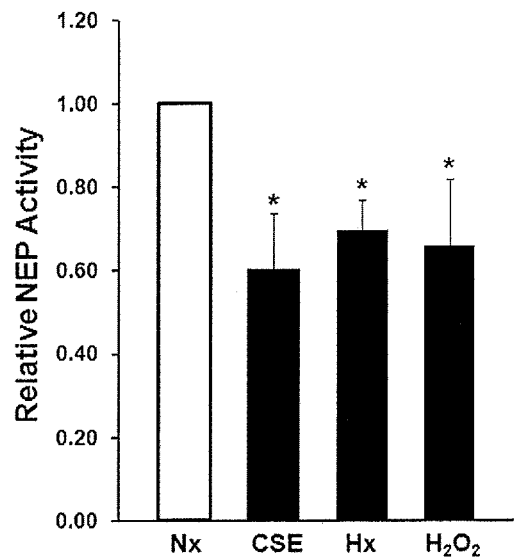
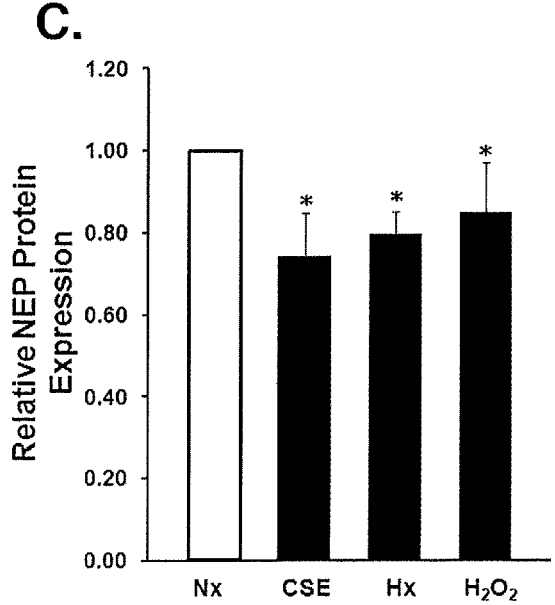
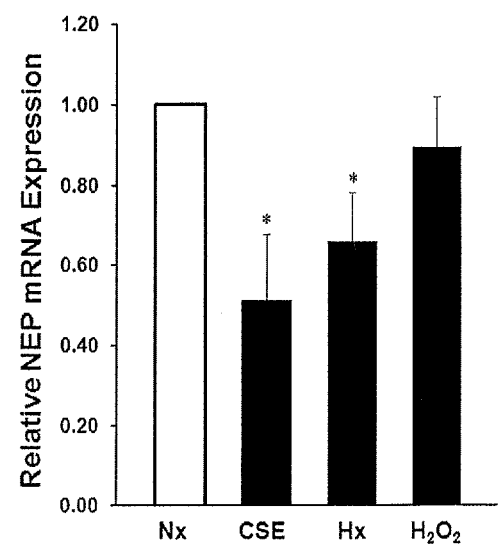
FIG. 7A-D

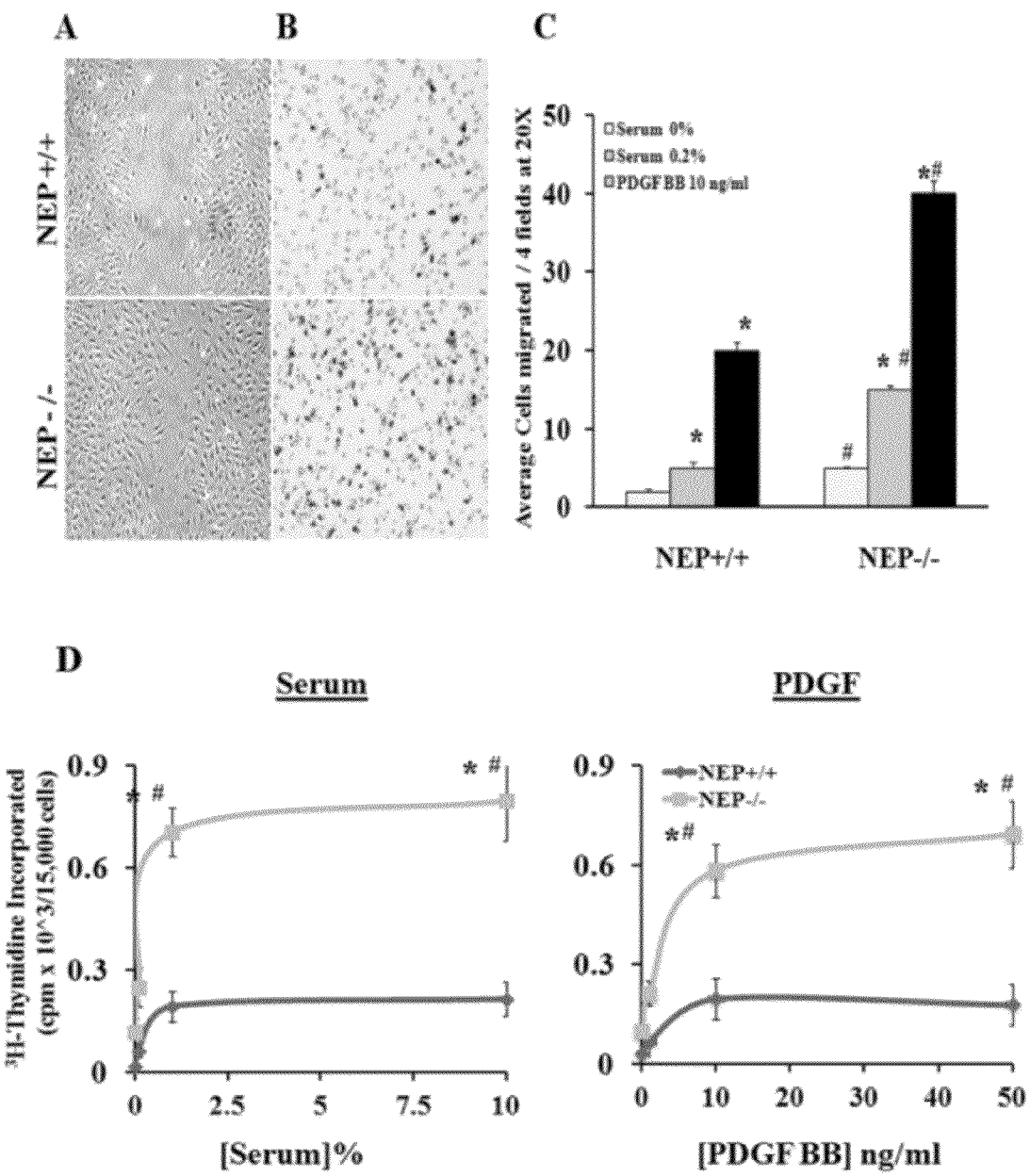
FIGS. 9A-D

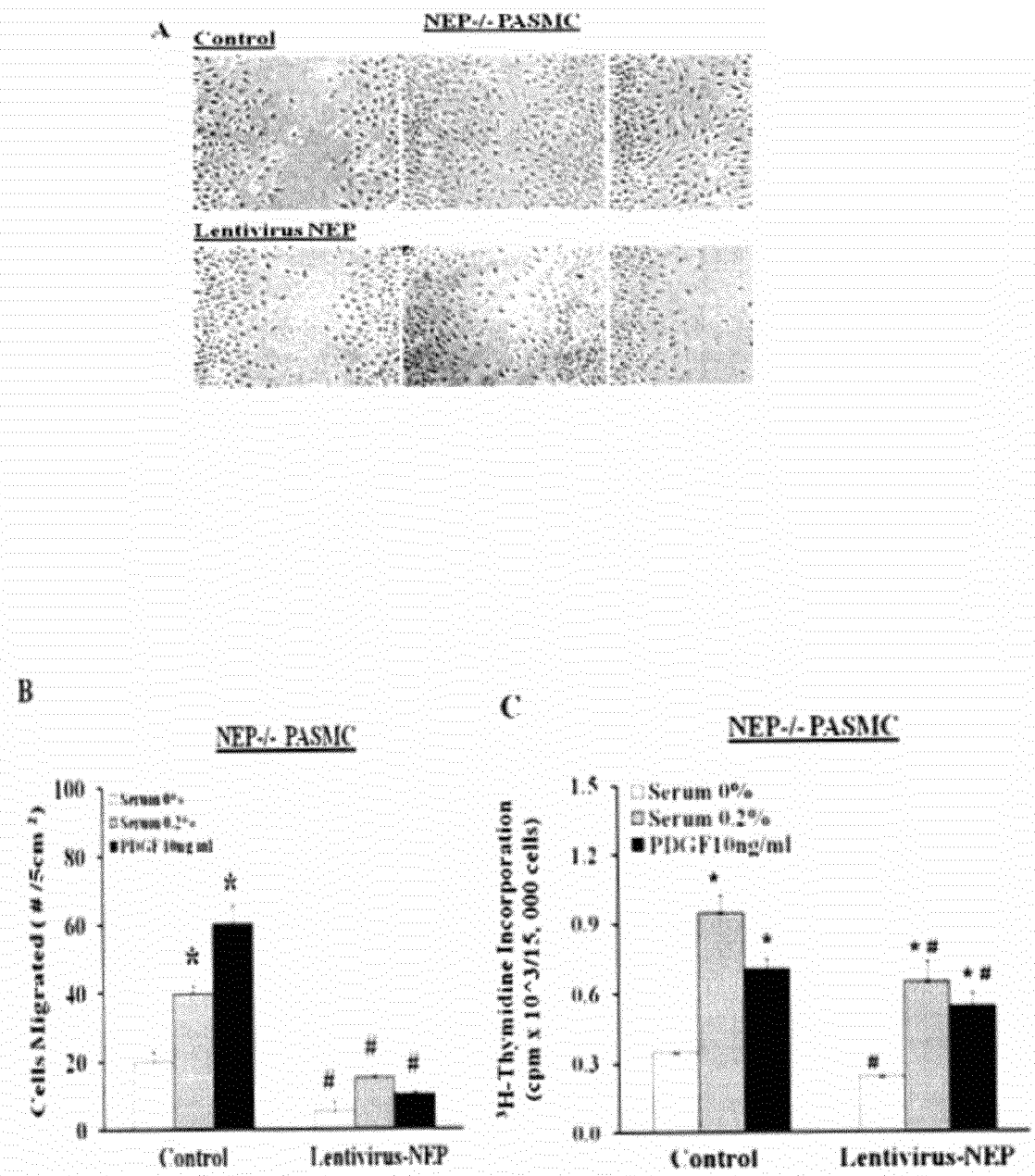
FIGS. 10A-C

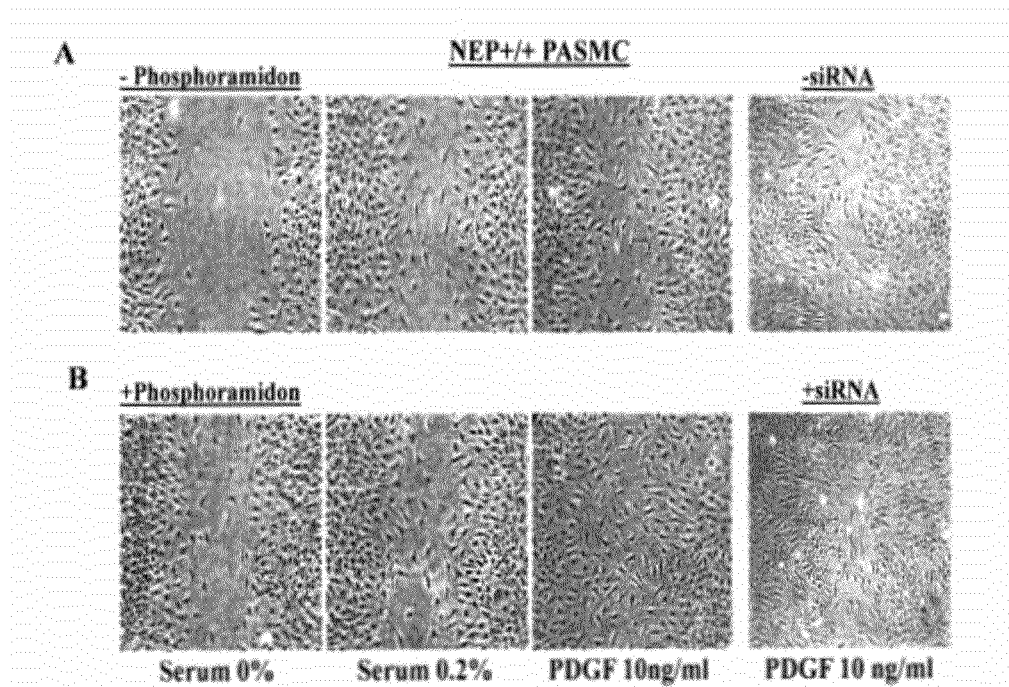
FIGS. 11A-B

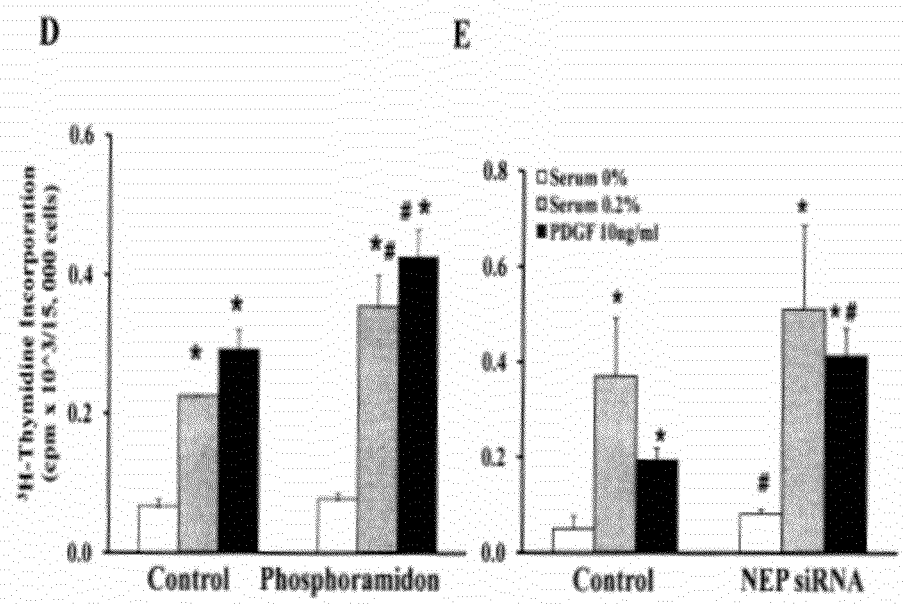
FIGS. 11D-E

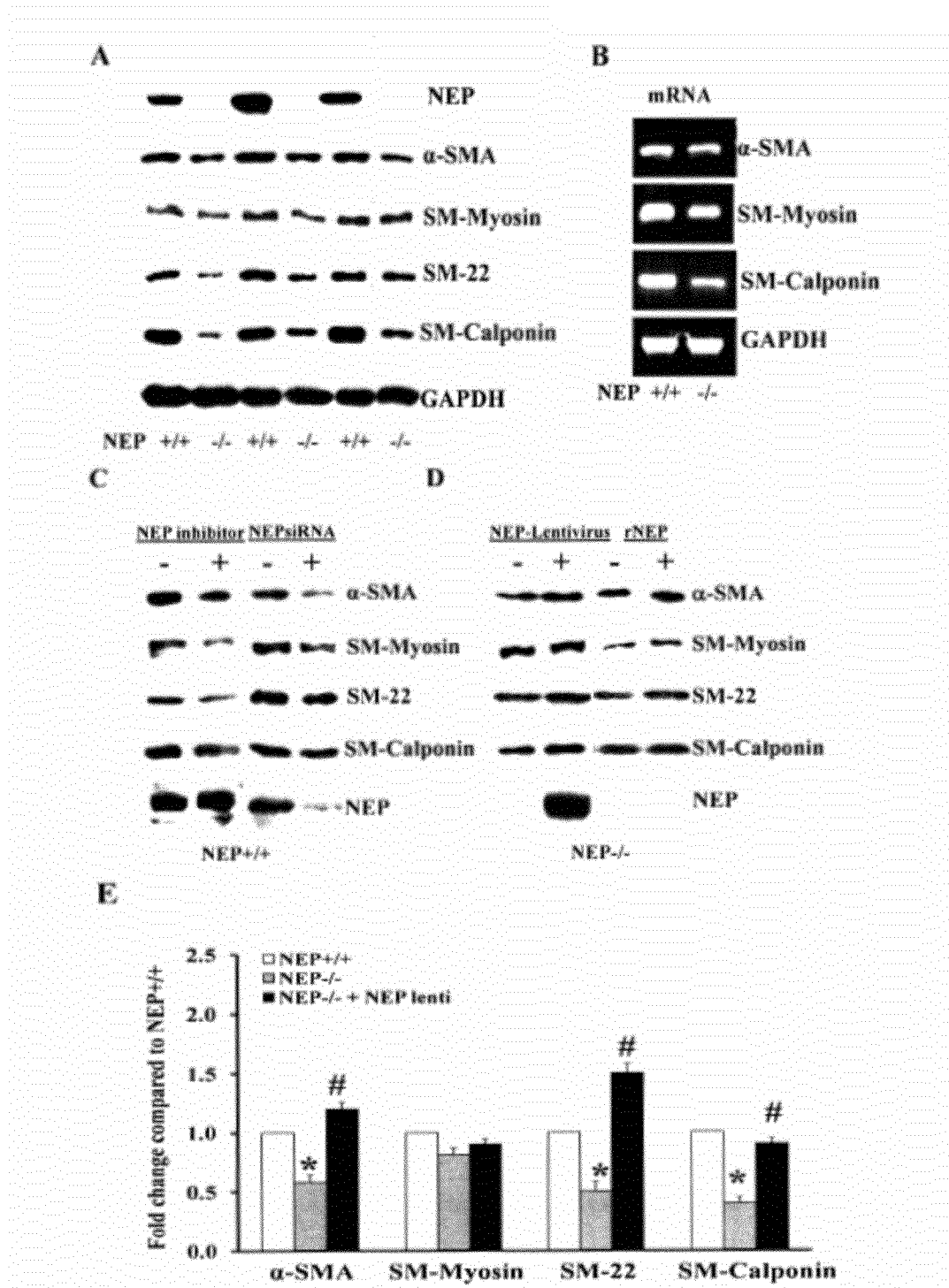
FIGS. 12A-E

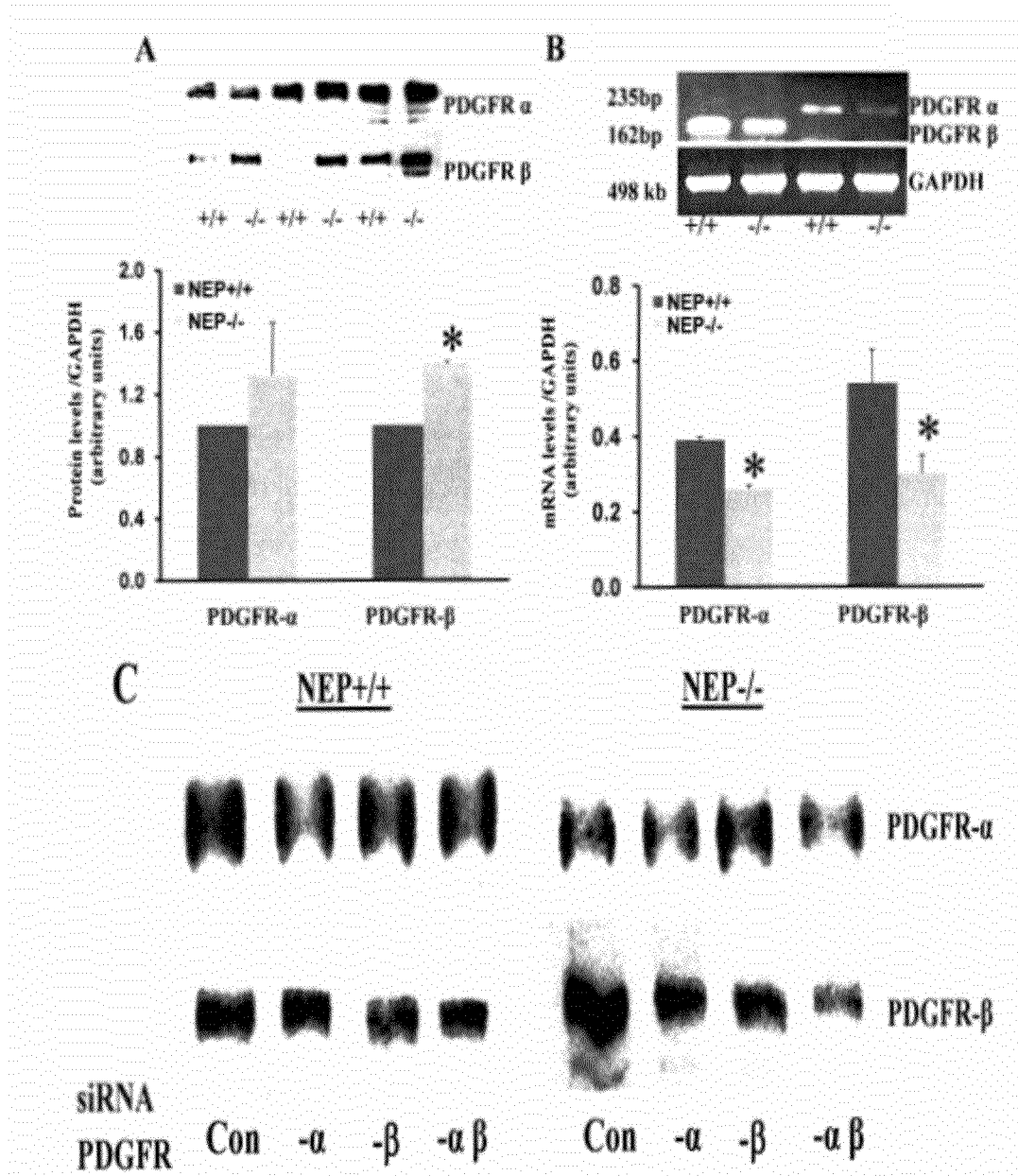
FIGS. 13A-C

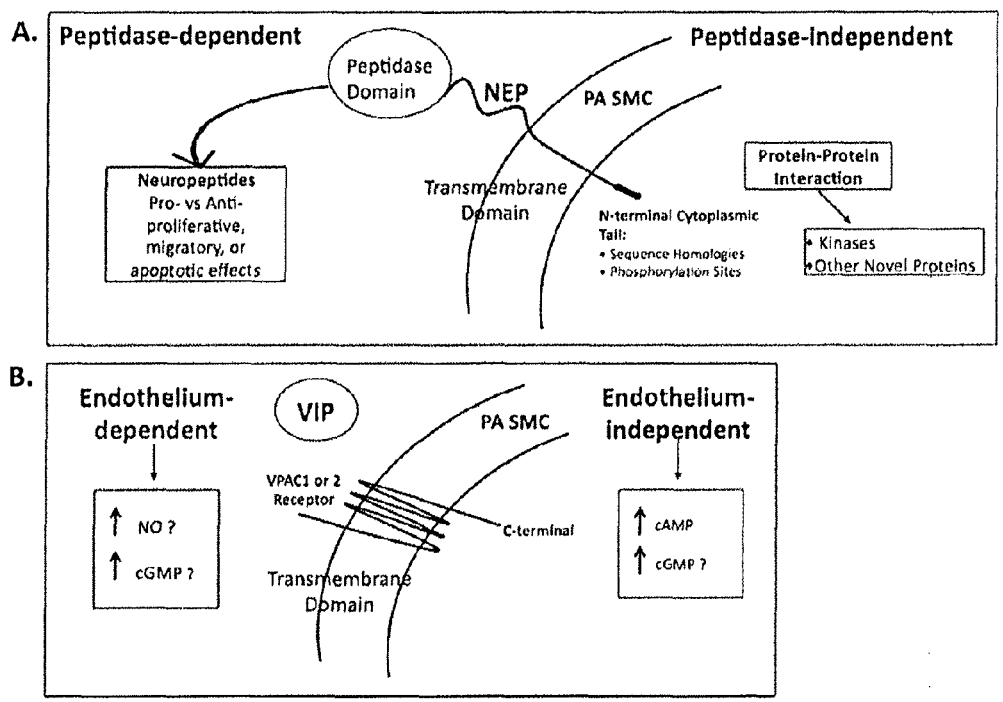
FIG. 14A-B

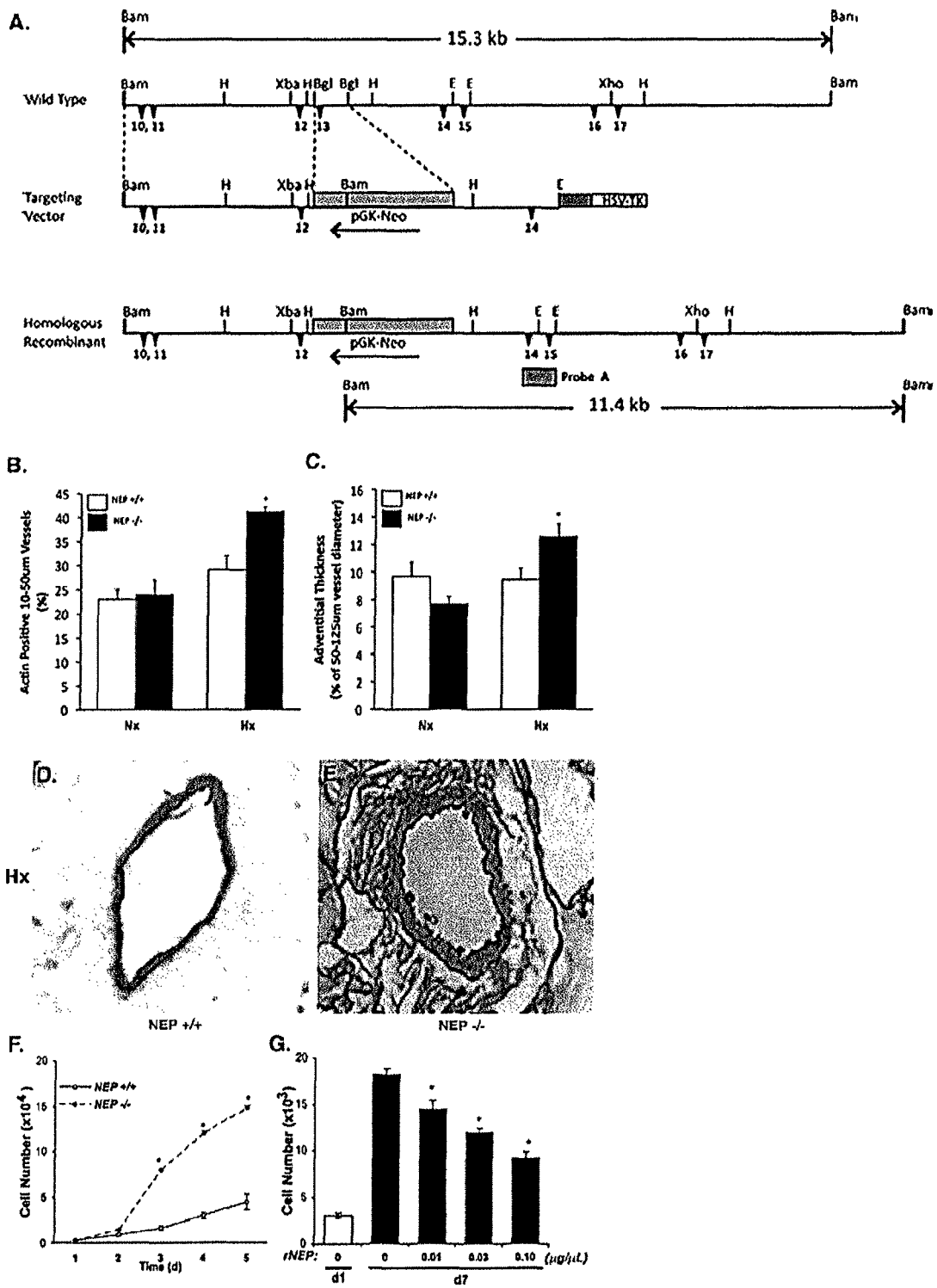
FIG. 15A-G

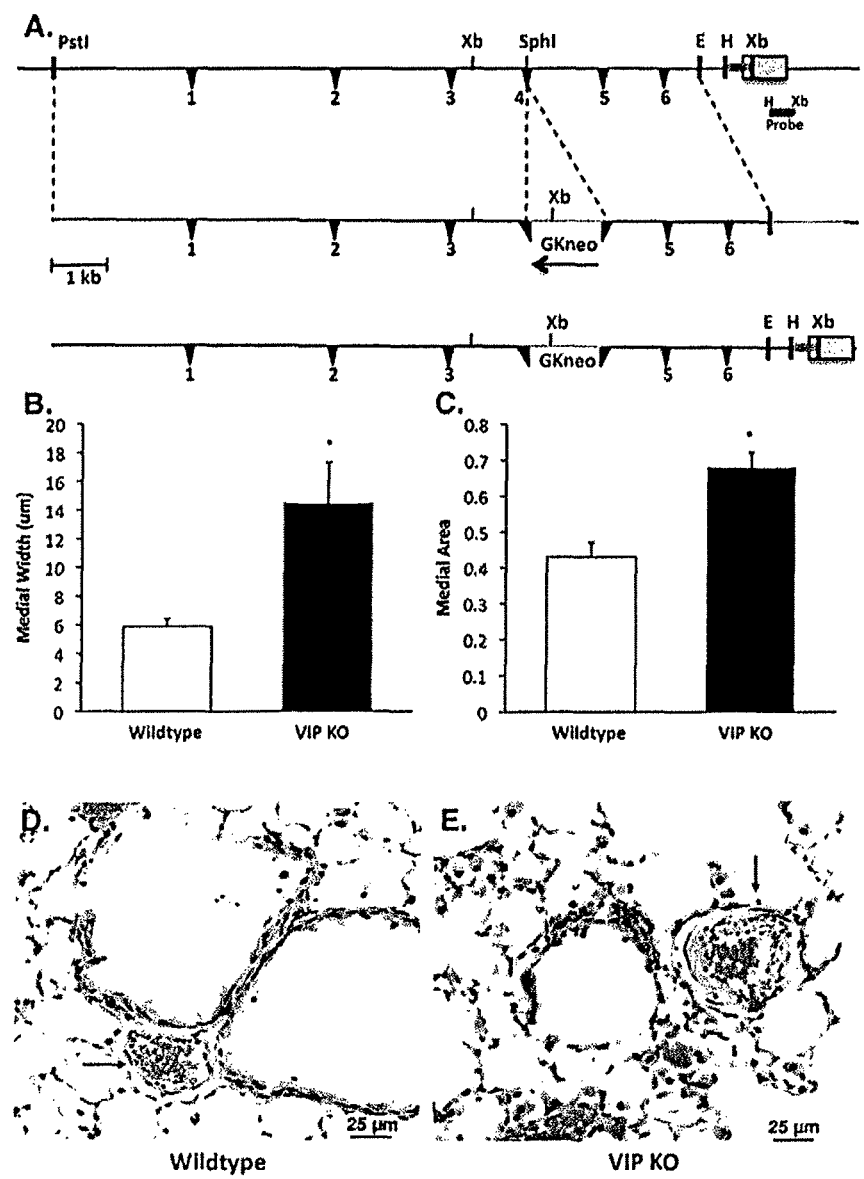
FIG. 16A-E

SEQUENCE LISTING

<160> NUMBER OF SEQ ID NOS: 16

<210> SEQ ID NO 1
<211> LENGTH: 750
<212> TYPE: PRT
<213> ORGANISM: Artificial Sequence
<220> FEATURE:
<223> OTHER INFORMATION: Synthetic primer

<400> SEQUENCE: 1

```
Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
            20                  25                  30

Val Leu Val Leu Leu Thr Ile Ile Ala Val Thr Met Ile Ala Leu
        35                  40                  45

Tyr Ala Thr Tyr Asp Asp Gly Ile Cys Lys Ser Ser Asp Cys Ile Lys
50                  55                  60

Ser Ala Ala Arg Leu Ile Gln Asn Met Asp Ala Thr Thr Glu Pro Cys
65                  70                  75                  80

Thr Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285

Lys Pro Glu Asp Arg Asn Asp Pro Met Leu Leu Tyr Asn Lys Met Thr
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350
```

```
Thr Lys Leu Lys Pro Ile Leu Thr Lys Tyr Ser Ala Arg Asp Leu Gln
            355                 360                 365

Asn Leu Met Ser Trp Arg Phe Ile Met Asp Leu Val Ser Ser Leu Ser
        370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
        435                 440                 445

Glu Val Phe Ile Gln Thr Leu Asp Asp Leu Thr Trp Met Asp Ala Glu
        450                 455                 460

Thr Lys Lys Arg Ala Glu Glu Lys Ala Leu Ala Ile Lys Glu Arg Ile
465                 470                 475                 480

Gly Tyr Pro Asp Ile Val Ser Asn Asp Asn Lys Leu Asn Asn Glu
                485                 490                 495

Tyr Leu Glu Leu Asn Tyr Lys Glu Asp Glu Tyr Phe Glu Asn Ile Ile
            500                 505                 510

Gln Asn Leu Lys Phe Ser Gln Ser Lys Gln Leu Lys Lys Leu Arg Glu
        515                 520                 525

Lys Val Asp Lys Asp Glu Trp Ile Ser Gly Ala Ala Val Val Asn Ala
        530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
        595                 600                 605

Gln Gln Ser Ala Ser Asn Phe Lys Glu Gln Ser Gln Cys Met Val Tyr
610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
        675                 680                 685

Asn Phe Ala Gln Val Trp Cys Gly Thr Tyr Arg Pro Glu Tyr Ala Val
        690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750

<210> SEQ ID NO 2
<211> LENGTH: 5643
<212> TYPE: DNA
```

<213> ORGANISM: Artificial Sequence
<220> FEATURE:
<223> OTHER INFORMATION: Synthetic primer

<400> SEQUENCE: 2

```
gagagcgccg agacgcgcgg ggcgcggaga tgtgcaagtg gcgaagcttg accgagagca      60
ggctggagca gccgcccaac tcctggcgcg ggatctgctg aggggtcacg attttaggtg     120
atgggcaagt cagaaagtca gatggatata actgatatca acactccaaa gccaaagaag     180
aaacagcgat ggactccact ggagatcagc ctctcggtcc ttgtcctgct cctcaccatc     240
atagctgtga caatgatcgc actctatgca acctacgatg atggtatttg caagtcatca     300
gactgcataa aatcagctgc tcgactgatc caaaacatgg atgccaccac tgagccttgt     360
acagactttt tcaaatatgc ttgcggaggc tggttgaaac gtaatgtcat tcccgagacc     420
agctcccgtt acggcaactt tgacatttta agagatgaac tagaagtcgt tttgaaagat     480
gtccttcaag aacccaaaac tgaagatata gtagcagtgc agaaagcaaa agcattgtac     540
aggtcttgta taaatgaatc tgctattgat agcagaggtg agaacctct actcaaactg      600
ttaccagaca tatatgggtg gccagtagca acagaaaact gggagcaaaa atatggtgct     660
tcttggacag ctgaaaaagc tattgcacaa ctgaattcta aatatgggaa aaagtccttt     720
attaatttgt tgttggcac tgatgataag aattctgtga atcatgtaat tcatattgac      780
caacctcgac ttggcctccc ttctagagat tactatgaat gcactggaat ctataaagag     840
gcttgtacag catatgtgga tttatgatt tctgtggcca gattgattcg tcaggaagaa      900
agattgccca tcgatgaaaa ccagcttgct ttggaaatga aaaagttat ggaattggaa      960
aaagaaattg ccaatgctac ggctaaacct gaagatcgaa atgatccaat gcttctgtat    1020
aacaagatga cattggccca gatccaaaat aacttttcac tagagatcaa tgggaagcca    1080
ttcagctggt tgaatttcac aaatgaaatc atgtcaactg tgaatattag tattacaaat    1140
gaggaagatg tggttgttta tgctccagaa tatttaacca aacttaagcc cattcttacc    1200
aaatattctg ccagagatct tcaaaattta atgtcctgga gattcataat ggatcttgta    1260
agcagcctca gccgaaccta caaggagtcc agaaatgctt ccgcaaggc ccttttatggt    1320
acaacctcag aaacagcaac ttggagacgt tgtgcaaact atgtcaatgg gaatatggaa    1380
aatgctgtgg ggaggcttta tgtggaagca gcatttgctg agagagtaa acatgtggtc     1440
gaggatttga ttgcacagat ccgagaagtt tttattcaga ctttagatga cctcacttgg    1500
atggatgccg agacaaaaaa gagagctgaa gaaaaggcct tagcaattaa agaaaggatc    1560
ggctatcctg atgacattgt ttcaaatgat aacaaactga ataatgagta cctcgagttg    1620
aactacaaag aagatgaata cttcgagaac ataattcaaa atttgaaatt cagccaaagt    1680
aaacaactga agaagctccg agaaaaggtg gacaaagatg agtggataag tggagcagct    1740
gtagtcaatg cattttactc ttcaggaaga atcagatag tcttcccagc cggcattctg     1800
cagccccct tctttagtgc ccagcagtcc aactcattga actatggggg catcggcatg    1860
gtcataggac acgaaatcac ccatggcttc gatgacaatg gcagaaactt taacaaagat    1920
ggagacctcg ttgactggtg gactcaacag tctgcaagta actttaagga gcaatcccag    1980
tgcatggtgt atcagtatgg aaactttcc tgggacctgg caggtggaca gcaccttaat     2040
ggaattaata cactgggaga aaacattgct gataatggag tcttggtca agcatacaga     2100
gcctatcaga attatattaa aaagaatggc gaagaaaaat tacttcctgg acttgaccta    2160
aatcacaaac aactatttt cttgaacttt gcacaggtgt ggtgtggaac ctataggcca    2220
```

```
gagtatgcgg ttaactccat taaaacagat gtgcacagtc caggcaattt caggattatt    2280
gggactttgc agaactctgc agagttttca gaagcctttc actgccgcaa gaattcatac    2340
atgaatccag aaaagaagtg ccgggtttgg tgatcttcaa agaagcatt  gcagcccttg    2400
gctagacttg ccaacaccac agaaatgggg aattctctaa tcgaaagaaa atgggcccta    2460
ggggtcactg tactgacttg agggtgatta acagagaggg caccatcaca atacagataa    2520
cattaggttg tcctagaaag ggtgtggagg gaggaagggg gtctaaggtc tatcaagtca    2580
atcatttctc actgtgtaca taatgcttaa tttctaaaga taatattact gtttatttct    2640
gtttctcata tggtctacca gtttgctgat gtccctagaa aacaatgcaa aacctttgag    2700
gtagaccagg atttctaatc aaaagggaaa agaagatgtt gaagaataca gttaggcacc    2760
agaagaacag taggtgacac tatagtttaa aacacattgc ctaactacta gtttttactt    2820
ttatttgcaa catttacagt ccttcaaaat ccttccaaag aattcttata cacattgggg    2880
ccttggagct tacatagttt taaactcatt tttgccatac atcagttatt cattctgtga    2940
tcatttattt taagcactct taaagcaaaa aatgaatgtc taaaattgtt ttttgttgta    3000
cctgctttga ctgatgctga gattcttcag gcttcctgca attttctaag caatttcttg    3060
ctctatctct caaaacttgg tattttttcag agatttatat aaatgtaaaa ataataattt    3120
ttatatttaa ttattaacta catttatgag taactattat tataggtaat caatgaatat    3180
tgaagtttca gcttaaaata aacagttgtg aaccaagatc tataaagcga tatacagatg    3240
aaaatttgag actatttaaa cttataaatc atattgatga aaagatttaa gcacaaactt    3300
tagggtaaaa attgccattg gacagttgtc tagagatata tatacttgtg gttttcaaat    3360
tggactttca aaattaaatc tgtccctgag agtgtctctg ataaaagggc aaatctgcac    3420
ctatgtagct ctgcatctcc tgtcttttca ggtttgtcat cagatggaaa tattttgata    3480
ataaattgaa attgtgaact cattgctccc taagactgtg acaactgtct aactttagaa    3540
gtgcatttct gaatagaaat gggaggcctc tgatggacct tctagaatta taagtcacaa    3600
agagttctgg aaaagaactg tttactgctt gataggaatt catcttttga ggcttctgtt    3660
cctctctttt cctgttgtat tgactatttt cgttcattac ttgattaaga ttttacaaaa    3720
gaggagcact tccaaaattc ttattttttcc taacaaaaga tgaaagcagg gaatttctat    3780
ctaaatgatg agtattagtt ccctgtctct tgaaaaatgc ccatttgcct ttaaaaaaaa    3840
aagttacaga aatactataa catatgtaca taaattgcat aaagcataag tatacagttc    3900
aataaactta actttaactg aacaatggcc ctgtagccag cacctgtaag aaacagagca    3960
gtaccagcgc tctaaaagca cctccttgtc actttattac tcccagaaca acaactatcc    4020
tgacttctaa tatcattcac tagctttgcc tggttttgtc ttttatgcag atagaatcaa    4080
tcagtatgta ttcttttgtg cctggcttct ttctctcagc cttacatttg tgagattcct    4140
ctgtattgtg ctgattgtgg atcttttcat tctcattgca gaataatgtt ctattgtggg    4200
acttattaca atttgttcat cctattgttg atgggcactt gagaactttc cattttggcg    4260
ctattacaaa tagtgcaact atgaatgtac tgcatgttac catcttactt gagcctttaa    4320
tggacttatt tcttcaaatc cttccaaaaa ttattataag cattgaaatt atagtttcaa    4380
gccaactgtg gatacccctta cccttttcctc ctttatcaca accaccgtta caagtatact    4440
tatatttccc taaatacat  ttaaaactta cctaagtgac atttgtagtt ggagtaatag    4500
gagcttccag ctctaataaa acagctgtct ctaacttatt ttatttccat catgtcagag    4560
```

```
caggtgaaga gccagaagtg aagagtgact agtacaaatt ataaaaagcc actagactct   4620
tcactgttag cttttttaaaa cattaggctc ccatccctat ggaggaacaa ctctccagtg   4680
cctggatccc ctctgtctac aaatataaga ttttctgggc ctaaaggata gatcaaagtc   4740
aaaaatagca atgcctccct atccctcaca catccagaca tcatgaattt acatggtac    4800 tcttgttgag ttctgtagag ccttctgatg tctctaaagc actaccgatt ctttggagtt   4860
gtcacatcag ataagacata tctctaattc catccataaa tccagttcta ctatggctga   4920
gttctggtca agaaagaaa gtttagaagc tgagacacaa agggttggga gctgatgaaa    4980
ctcacaaatg atggtaggaa gaagctctcg acaatacccg ttggcaagga gtctgcctcc   5040
atgctgcagt gttcgagtgg attgtaggtg caagatggaa aggattgtag gtgcaagctg   5100
tccagagaaa agagtccttg ttccagccct attctgccac tcctgacagg gtgaccttgg   5160
gtatttgcaa tattcctttg ggcctctgct tctctcacct aaaaaaagag aattagatta   5220
tattggtggt tctcagcaag agaaggagta tgtgtccaat gctgccttcc catgaatctg   5280
tctcccagtt atgaatcagt gggcaggata aactgaaaac tcccatttac gtgtctgaat   5340
cgagtgagac aaaatttag tccaaataac aagtaccaaa gttttatcaa gtttgggtct    5400
gtgctgctgt tactgttaac catttaagtg gggcaaaacc ttgctaattt tctcaaaagc   5460
atttatcatt cttgttgcca cagctggagc tctcaaacta aaagacattt gttattttgg   5520
aaagaagaaa gactctattc tcaaagtttc ctaatcagaa atttttatca gtttccagtc   5580
tcaaaaatac aaaataaaaa caaacgtttt taatactatt gcttttatgc ctagtcaact   5640
ctg                                                                 5643

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
ggtggctttt aggatggcaa g                                             21

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
actggaacgg tgaaggtgac ag                                            22

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gtcccagaca tcagggagta a                                             21

<210> SEQ ID NO 6
<211> LENGTH: 21
<212> TYPE: DNA
<213> ORGANISM: Artificial Sequence
```

```
<220> FEATURE:
<223> OTHER INFORMATION: Synthetic primer

<400> SEQUENCE: 6
tcggatactt cagcgtcagg a                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
caacaagggt ccatcctacg g                                              21

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
atctgggcgg cctacatca                                                 19

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
aagctgcggc tagaggtca                                                 19

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ccctcccttt gatggctgag                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
caaaccctga gaccacaatg                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tcccccaaca gtaacccaag                                                20
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tgcctcagcc aaatgtcacc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tgctcaccac ctcgtattcc                                               20

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
gccaaggtca tccatgacaa c                                             21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
gtccaccacc ctgttgctgt a                                             21
```

TREATMENT OF PULMONARY VASCULAR REMODELING WITH NEPRILYSIN

This application claims benefit of priority to U.S. Provisional Application Ser. No. 61/379,641, filed Sep. 2, 2010, the entire contents of which are hereby incorporated by reference.

This invention was made with government support under grant numbers RO1 HL078927, R03 HL095439 and PPG HL14985 awarded by the National Institutes of Health. The government has certain rights in the invention.

BACKGROUND OF THE INVENTION

I. Field of the Invention

The present invention relates to the fields of medicine, pathology and molecular biology.

More particular the invention relates to the role of neprilysin in pulmonary hypertension and chronic obstructive pulmonary disease (COPD), and methods of using neprilysin to diagnose and treat these diseases.

II. Related Art

Chronic obstructive pulmonary disease (COPD) is a leading cause of death; cigarette smoking is its primary risk factor (Churg et al., 2008). Pulmonary vascular remodeling, characterized by thickening, muscularization, and rarification of the distal vasculature (Rabinovitch, 2008; Preston, 2007; Peinado et al., 2008), complicates COPD by contributing to pulmonary hypertension (PHTN) (Preston, 2007; Jeffery, 2001). Many COPD patients have mild PHTN at rest (Steiner, 2009; Naeije and Barbera, 2001; Thabut et al., 2005); however, the prevalence of exercise-induced PHTN, which also may lead to right heart failure in COPD (Weitzenblum et al., 2009), is much higher (over 91%; Steiner, 2009; Kubo et al., 2000).

COPD-associated PHTN is likely caused by initial injury of the pulmonary vascular endothelium by cigarette smoke (CS) (Peinado et al., 2008), followed by inflammation and hypoxia, all which may involve oxidant mechanisms (Dempsey et al., 1996; Kong et al., 2006). Factors that may contribute to variable susceptibility to COPD-associated PHTN, including interleukin-6 (IL-6) and the serotonin transporter (5HTT) (Steiner, 2009; Kubo et al., 2000; Chaouat et al., 2009; Ulrich et al., 2010), have been extensively investigated.

Neprilysin (NEP, CD10) is a transmembrane zinc peptidase that degrades specific peptides, and is widely expressed, including in pulmonary arterial (PA) SMCs, endothelial cells, and fibroblasts (Shipp et al., 1988; Sunday et al., 1992). NEP activity/expression is decreased by CS (Dusser et al., 1989), hypoxia (Dempsey et al., 2009; Carpenter and Stenmark, 2001), or reactive oxygen species (ROS) (Shinall et al., 2005). Hypoxic NEP null mice develop greater PHTN, and PA SMCs from these mice grow faster than those from wt mice, suggesting that NEP protects against chronic hypoxic PHTN, in part by suppressing PA SMC growth and migration (Dempsey et al., 2009). However, NEP's role in human pulmonary vascular remodeling complicating chronic lung disease, has not been investigated.

SUMMARY OF THE INVENTION

Thus, in accordance with the present invention, there is provided a method for treating a subject with pulmonary vascular remodeling comprising administering to said subject an agonist of neprilysin. The agonist may be administered orally, intravenously, intraarterially, subcutaneously, transdermally or by inhalation. The subject is a human, is or was a smoker, and/or have emphysema. The agonist may be given more than once, such as given daily in a chronic dosing regimen. The subject may be administered a second therapy.

The agonist of neprilysin may be an expression cassette comprising a polynucleotide encoding a neprilysin polypeptide under the control of a promoter operable in eukaryotic cells. The promoter may be heterologous to the polynucleotide sequence, and may be selected from the group consisting of hsp68, SV40, CMV, MKC, $GAL4_{UAS}$, HSV and β-actin. The promoter may be a tissue specific promoter or an inducible promoter. The expression cassette may be contained in a viral vector, such as a retroviral vector, an adenoviral vector, and adeno-associated viral vector, a vaccinia viral vector, a lentivirus vector or a herpesviral vector. Alternatively, the expression cassette may be contained in a non-viral vector, such as one comprised within a lipid formulation. The expression cassette may further comprise a polyadenylation signal. The agonist may instead be neprilysin or an enzymatically active fragment of neprilysin, an antioxidant, a lysosomal inhibitor or a proteasomal inhibitor.

The subject may have pulmonary arterial hypertension (Group 1 PAH), pulmonary veno-occlusive disease (PVOD) and pulmonary capillary hemangiomatosis (PCH) (Group 1'), pulmonary hypertension due to left heart disease (Group 2 PH), pulmonary hypertension due to lung disease and/or hypoxia (Group 3), chronic thromboembolic pulmonary hypertension (Group 4), pulmonary hypertension with unclear or multifactorial etiologies (Group 5), idiopathic forms of pulmonary vascular disease, or a lung disorder that including any form of acute and chronic lung injury and inflammation (ARDS, ILD, pneumonia, COPD, asthma), or primary lung vascular disorders (idiopathic, collagen vascular-associated, liver disease-associated, drug-associated, HIV-associated, blood clot-induced pulmonary hypertension).

In another embodiment, there is provided a method of diagnosing pulmonary vascular remodeling in a subject comprising the steps of (i) obtaining a tissue sample comprising lung tissue, pulmonary vascular tissue, endothelial tissue or fibroblast tissue from a subject; and (ii) assessing the expression of neprilysin in cells of said sample, wherein a reduced amount of neprilysin expression in cells of said sample, as compared to healthy cells, indicates that said subject has pulmonary vascular remodeling. The sample may be a lung tissue homogenate. The cells may be circulating progenitor cells, stem cells or inflammatory cells. The sample may be pulmonary arterial smooth muscle. Step (ii) may comprise assessing neprilysin protein expression, or assessing neprilysin mRNA expression, such as under conditions suitable to amplify said mRNA. Assessing protein expression may comprise contacting a cell lysate of said sample with an antibody that binds immunologically to neprilysin, such as by ELISA or Western blot. Assessing may also comprise measuring zinc peptidase activity in cells of said sample. The pulmonary vascular remodeling may underlie pulmonary hypertension, idiopathic forms of pulmonary vascular disease, or a lung disorder that could include any form of acute and chronic lung injury and inflammation (ARDS, ILD, pneumonia, COPD, asthma), primary lung vascular disorders (idiopathic, collagen vascular associated, liver disease associated, drug-associated, HIV-associated, blood clot-induced pulmonary hypertension).

In still a further embodiment, there is provided a method of screening a candidate substance for activity against pulmonary vascular remodeling comprising the steps of (i) providing a cell expressing neprilysin; (ii) contacting said cell with said candidate substance; and (iii) determining the effect of said candidate substance on expression or activity of neprilysin, wherein an increase in neprilysin expression or activity identifies said substance as having activity against pulmonary vascular remodeling. The cell may be a lung cell, a pulmonary arterial smooth muscle cell, and endothelial cell or a fibroblast cell. The cell may be contacted in vitro or in vivo. The method may further comprise testing said candidate substance in a disease model for pulmonary vascular remodeling. Determining may comprise measuring zinc peptidase activity, measuring neprilysin mRNA expression, or measuring neprilysin protein expression, such as by contacting a lysate of said cell with an antibody that binds immunologically to neprilysin, including subjecting proteins of said sample to ELISA or Western blot.

In yet another embodiment, there is provided a method of screening a candidate substance for activity against pulmonary vascular remodeling comprising the steps of (i) providing a cell comprising an expression construct comprising a native neprilysin promoter operably linked to a detectable marker; (ii) contacting said cell with said candidate substance; and (iii) determining the effect of said candidate substance on expression of the detectable marker, wherein an increase in expression of the detectable marker identifies said substance as having activity against pulmonary vascular remodeling. The cell may be a lung cell, a pulmonary arterial smooth muscle cell, and endothelial cell or a fibroblast cell. The cell may be contacted in vitro or in vivo. The method may further comprise testing said candidate substance in a disease model for pulmonary vascular remodeling. The detectable marker may be an enzyme and determining may comprise measuring enzyme activity. The detectable marker may be a fluorescent or chemiluminescent molecule and determining may comprise measuring fluorescence or chemiluminescence. The detectable marker may be an antigen and determining may comprise measuring binding of an antibody to said antigen. The cell may be transiently transformed or stably transformed with said expression construct.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIGS. 1A and B), Morphometric Analysis. (FIG. 1A) Endothelial stain demonstrates rarification in areas of emphysematous lung. Lung slides were stained with an antibody to the endothelial marker, CD31. The number of CD31 positive small pulmonary arteries (25-100 µm) per unit area were counted in 10 similarly inflated areas per sample and averaged. N=4 lung samples for 'Control' or COPD. (FIG. 1B) Human lung sample slides were stained with H&E and reviewed by a blinded lung pathologist. The three layers (intima, media, adventitia) of the small pulmonary arteries (25-100 µm) in each sample were scored from 0 to 3+ for structural changes (i.e. increased thickness). Five arteries were analyzed from each lung slide and the score was averaged for each lung. N=7 lung samples for 'Control' or COPD. *$p<0.05$ compared to 'Control'. (FIGS. 1C-H), Representative immunohistological images demonstrating prominent pulmonary vascular remodeling in COPD samples. (FIGS. 1C, D, and F, G) Pentachrome-stained intermediate and distal PAs (gray: endothelial, pink: medial, and yellow: adventitial layers are shown; FIG. 1C and FIG. 1F are 'Control'; FIG. 1D and FIG. 1G are COPD). (FIG. 1E) CD31-stained distal PA of COPD sample (endothelium is brown: DAB). Note the absence of intimal changes in this vessel, an example of the variability in this signal. (FIG. 1H) α-SM actin-stained distal PA of COPD sample (media is brown: DAB). Note the prominent adjacent adventitia. Small, distal vessels are 25-100 µm. Larger, intermediate vessels are 100-500 µm. Small arrowheads (FIGS. 1D and E) point to the intimal (endothelial) vessel layer. Small arrows (FIGS. 1D, E, G, and H) point to the medial (SMC) vessel layer. Large arrowhead (FIG. 1H) points to the adventitial vessel layer. Black scale bars represent 50 µm; striped scale bars represent 100 µm.

(FIG. 2A) NEP activity was determined fluorometrically, n=13-14 per group, *$p<0.017$ compared to 'Control' ($p<0.05/3$ after application of Bonferroni Correction for multiple comparisons). (FIG. 2B) DPPIV activity was determined by luminescence. N=4-5 per group.

(FIG. 3A) NEP expression was determined by Western blot using NEP specific antibody, n=13-14 per group. *$p<0.017$ compared to 'Control' ($p<0.05/3$ after application of Bonferroni Correction for multiple comparisons). (FIG. 3B, upper) Representative Western analysis of 'Control' and COPD lung homogenates (30 µg each), probed with anti-human NEP antibody as described in the Methods. The two lanes were not adjacent to one another on gel, but were from the same gel and were treated identically. (FIG. 3B, lower) Representative nitrocellulose membrane stained with Coomassie-Blue, after transfer of human lung homogenates, routinely used as a loading control, as well as a check on sample and transfer integrity. (FIG. 3C) NEP mRNA expression was determined by qRTPCR using human NEP primers from Qiagen. N=9 per group.

(FIG. 4A) Human lung sample slides were stained with anti-NEP antibody at 1:100 dilution and blindly reviewed. The intensity of NEP signal in alveolar walls and in the distal pulmonary vessels (25-100 µm) in each sample were scored from 0 to 4+. Nine areas were analyzed from each lung sample and the score was averaged for each lung. Control samples are represented by an open box, and COPD samples are represented by a black box. N=5 lung samples for 'Control' or COPD. *p<0.001 compared to 'Control' alveolar walls; **p<0.001 compared to all other groups. 'Control' alveolar walls did not differ significantly from 'Control' distal vessels. (FIGS. 4B and C), Representative images of NEP-stained distal vessels from 'Control' and COPD samples. (FIG. 4B) 'Control' lung, n=6. (FIG. 4C) Advanced COPD lung with pulmonary vascular remodeling, n=9. NEP signal is brown (DAB). Arrows point to endothelial cells. Arrowheads point to alveolar wall. Scale bars represent 50 µm.

(FIGS. 5A and C) 'Control' lung, n=2. (FIGS. 5B and D) Advanced COPD lung, n=3. Shown are images of lung parenchyma (FIGS. 5A and B) or distal (25-100 µm) pulmonary vessels (FIGS. 5C and D). Nitrotyrosine signal is brown (DAB). Black scale bars represent 50 µm; striped scale bars represent 100 µm. (FIG. 6A) Human recombinant NEP was incubated at 37° C. for 24 h with the indicated concentrations of $H_2O_2$, diluted 40-fold and assayed for residual NEP activity, n=1. (FIG. 6B) 'Control' whole human lung homogenates (n=6, 4 different samples) were incubated at 37° C. for 24 h with or without 100 µM $H_2O_2$, diluted 60-fold and assayed for residual NEP activity.

FIGS. 7A-D. Cigarette Smoke Extract (CSE), Hypoxia (Hx), and a Potent ROS ($H_2O_2$) Decrease NEP Activity and Expression in Human PA SMC. (FIG. 7A) Light microscopic image of normoxic human PA SMC (Clonetics). Note characteristic spindle shape. (FIG. 7B-D), PA SMC were exposed to CSE (5 µg/ml), hypoxia (3% $O_2$), or $H_2O_2$ (100 µM), as indicated, for 48 h. Values for normoxic control cells (1.00) were used to normalize others. (FIG. 7B) NEP catalytic activity, n=4-8 (4-6 cell populations). (FIG. 7C) NEP protein expression, measured by Western analysis and calculated by densitometry, n=5 (4 cell populations). (FIG. 7D) NEP mRNA levels measured by qRT-PCR, n=3 (3 cell populations). *p<0.05 vs Nx.

FIGS. 9A-E. Loss of NEP leads to increased migration and proliferation of murine PASMCs. Migration of PASMCs isolated from NEP+/+ and NEP−/− mice was measured by scratch and Boyden chamber assays and proliferation by $^3$H-thymidine incorporation as described in Methods. FIG. 9A shows a representative scratch assay and FIG. 9B a stained filter of migrated cells from a Boyden chamber assay. Number of cells migrated in 20× field from three different populations of PASMCs in response to serum (0.2%) and PDGF-BB (10 ng/ml) using Boyden chamber assay is shown in FIG. 9C. Thymidine incorporation in the presence of increasing concentrations of serum (0, 0.2, 1 and 10%) and PDGF-BB (0, 1, 10 and 50 ng/ml) from 3 different populations of PASMCs is shown in FIG. 9D. The inventor measured adhesion of NEP+/+ and NEP−/− PASMCs and is shown in FIG. 9E. (*) represents p≤0.05 for comparisons of treatments in a group and (#) represents p≤0.05 for comparisons between NEP+/+ and NEP−/− PASMCs.

FIGS. 10A-C. Lentivirus expression of wild-type NEP attenuates enhanced migration and proliferation observed with NEP−/− PASMCs. NEP−/− PASMCs were infected with lentivirus expressing full length human NEP at a multiplicity of infection (MOI) of 10 and its effects on migration and proliferation were assessed after 48 hr. FIG. 10A shows migration of cells in the presence of serum (0.2%) and PDGF (10 ng/ml) for 6 hr−/+ lentivirus expressing human NEP in a scratch assay. FIG. 10B shows a graphical representation of the number of cells migrated/5 $cm^2$ area of the scratch in the absence and presence of lentivirus expression from three different isolates. Thymidine incorporation in three different cell populations without and with lentivirus is shown in FIG. 10C. PASMCs were treated with 0.2% serum or PDGF (10 ng/ml) for 24 h for thymidine incorporation. (*) represents p≤0.05 for comparisons of treatments in a group and (#) represents p≤0.05 for comparisons between NEP+/+ and NEP−/− PASMCs.

FIGS. 11A-E. Inhibition of NEP activity or knock down with siRNA increases migration and proliferation in NEP+/+ PASMCs. NEP+/+ PASMCs were treated with either the NEP inhibitor, phosphoramidon (10 µMole/L), or transfected with NEP siRNA (10 nMole/L), and effects on migration and proliferation were assessed after 48 hr. FIG. 11A shows migration of cells in the presence of serum (0.2%) and PDGF (10 ng/ml) for 6 h−/+ phosphoramidon and FIG. 11B shows effect of NEP siRNA on PDGF induced migration. Graphical representation of the number of cells migrated in 5 $cm^2$ from 3 different populations is shown in FIG. 11C. FIG. 11D shows effect of phosphoramidon and FIG. 11E of NEP siRNA on thymidine incorporation in three different PASMC populations. Cells were treated with serum (0.2%) or PDGF (10 ng/ml) for 24 hr for thymidine incorporation. (*) represents p≤0.05 for comparison of treatments in a group and (#) represents p≤0.05 for comparisons between NEP+/+ and NEP−/− PASMCs.

FIGS. 12A-E. NEP regulates expression of SM-contractile proteins. Levels of SM-contractile proteins were measured in NEP+/+ and NEP−/− PASMC lysates by Western blotting shown in FIG. 12A and by semi quantitative RT-PCR for select genes in FIG. 12B. Effect of NEP inhibition on SM-contractile protein expression in NEP+/+ cells using the NEP inhibitor, phosphoramidon (10 µMole/L), and mouse specific NEP siRNA (10 nMole/L) is shown in FIG. 12C. FIG. 12D shows the effect of re-expression of NEP on levels of SM contractile proteins in NEP−/− PASMC. NEP was expressed using a lentiviral human NEP construct or incubation with rNEP (10 µg/ml). GAPDH was used as loading control. At least 6 different paired isolates of cells were analyzed for protein expression. FIG. 12E shows—fold change in expression for the different proteins in NEP−/− compared to that in NEP+/+ PASMC. (*) represents p≤0.05 for comparison between NEP+/+ and NEP−/− PASMC.

FIGS. 13A-E. Loss of NEP increases PDGFR expression and its inhibition attenuates migration and proliferation in PASMCs. Levels of PDGFR α and β were measured at the protein level by Western blotting and mRNA level by semi quantitative RTPCR. Quantification of protein from 3 different isolates normalized to GAPDH is shown in FIGS. 13A and 13B show normalized mRNA levels. Flow cytometry analysis was performed to assess levels of PDGFR a and B levels and is shown in FIG. 13C. Cells were treated with siRNA (10 nM) to PDGFRα, PDGFRβ or αβ and migration and proliferation were measured after 48 hr. Panel C shows levels of PDGFR α and −β receptors in presence of siRNA.

PDGF AA ligand specific for PDGFRα and PDGF BB specific for PDGFR β were used to assess the contribution of each receptor to migration and proliferation in siRNA or PDGFR antagonist III (PDGFRI, 500 nM/L) treated NEP+/+ and NEP−/− cells. FIG. 13D shows migration and FIG. 13E thymidine incorporation in response to PDGF AA (10 ng/ml) and PDGF BB (10 ng/ml). Cells were treated for 24 h with inhibitor. (*) represents p≤0.05 for comparisons of treatments in a group (n=3).

FIGS. 14A-B. Potential mechanisms by which NEP and VIP may exert protective effects on PA SMC. (FIG. 14A) Peptidase-dependent, as well as -independent, effects of NEP contribute to anti-proliferative, anti-migratory, and pro-apoptotic effects which may be protective against pulmonary hypertension (PHTN). Various forms of injury including smoke and hypoxia can stimulate secondary PHTN. Genetic factors can potentiate this response to injury or promote the spontaneous development of PHTN. (FIG. 14B) Endothelium-dependent, as well as -independent, effects of VIP contribute to its vasodilatory and anti-proliferative properties which may be protective against PHTN.

FIGS. 15A-G. Development and elucidation of pulmonary vascular phenotype of the NEP KO mouse. (FIG. 15A) Gene targeting of the neprilysin (NEP) locus. Restriction map of the murine NEP locus (exons 10-17), targeting vector, and predicted map following homologous recombination. (Barn, BamHI; Bgl, BglII; E, EcoRI; H, HindIII; Xba, XbaI; Xho, XhoI) (reproduced with minor modifications with permission from the Journal of Experimental Medicine (Lu et al., 1995)). (FIGS. 15B-C) Increased pulmonary vascular remodeling in C57BL6 NEP−/− mice in response to chronic hypoxia (Hx; 5 wks, 18,000 ft.). (FIG. 15B) Increased muscularization of distal 10-50 μm pulmonary vessels in response to chronic hypoxia in NEP−/− mice; no change in vessel density. Lung sections were stained for both factor VIII (endothelial cell marker) and α-SMA; α-SMA-positive vessels were expressed as a percentage of factor VIII positive (total) vessels. (FIG. 15C) Hypoxia-induced thickening of proximal (50-100 μm) pulmonary arteries in NEP−/− mice. Medial and adventitial wall thickness were each measured with Stereo Investigator software. Adventitial thickness shown (medial thickening not shown). (FIGS. 15D-E) Histological demonstration of chronic hypoxia-induced structural changes in 50-125 μm pulmonary vessels from NEP+/+ and NEP−/− mice. Sections were stained for factor VIII (DAB, brown) and α-SMA (alkaline phosphatase, red). (FIG. 15D) NEP+/+5 weeks Hx. (FIG. 15E) NEP−/−5 weeks Hx. Magnification equals original×640. (FIGS. 15F-G) Quantification of proliferative changes for mouse NEP+/+ and NEP−/− isolated PA SMCs. (FIG. 15F) Isolated PA SMCs from NEP−/− mice grow faster than NEP+/+-derived cells. (FIG. 15G) Exogenous recombinant NEP inhibits the enhanced growth of PA SMCs isolated from NEP−/− mice (FIGS. 15B-G reproduced with minor modification with permission from the American Journal of Pathology (Dempsey et al., 2009)).

FIGS. 16A-E. Development and elucidation of pulmonary vascular phenotype of the VIP KO mouse. (FIG. 16A) Gene targeting of the vasoactive intestinal peptide (VIP) locus. Restriction map of the IP locus encompassing exons 1-7, targeting vector, and predicted map following homologous recombination. The targeting vector (neomycin cassette) was placed in inverse orientation just upstream from the PHI-encoding sequences on exon 4. Xb, XbaI; E, EcoRI; H, HindIII; GKneo, pPGK neo bpA; TK, pIC19R/MC-1-TK (reproduced with minor modifications with permission from the American Journal of Physiology: Regul Integ Comp Physiol. (Colwell et al., 2003)). (FIGS. 16B-C) In small PAs of comparable diameter (45 to 50 μm), media from male VIP−/− mice were considerably thicker than media from wt control mice. (FIG. 16D-E) Histological evidence of pulmonary vascular remodeling (wall thickening) in small pulmonary arteries of male VIP−/− mice breathing room air. Hematoxylin and eosin-stained sections of lungs from a male control mouse (FIG. 16D) and a male VIP−/− mouse (FIG. 16E). Media of vessels marked by arrows are 5 and 17 μm wide, respectively (FIGS. 16B-E were reproduced, with minor modifications, with permission from Circulation (Said et al., 2007)).

DETAILED DESCRIPTION OF THE PREFERRED EMBODIMENTS

Figure 1:
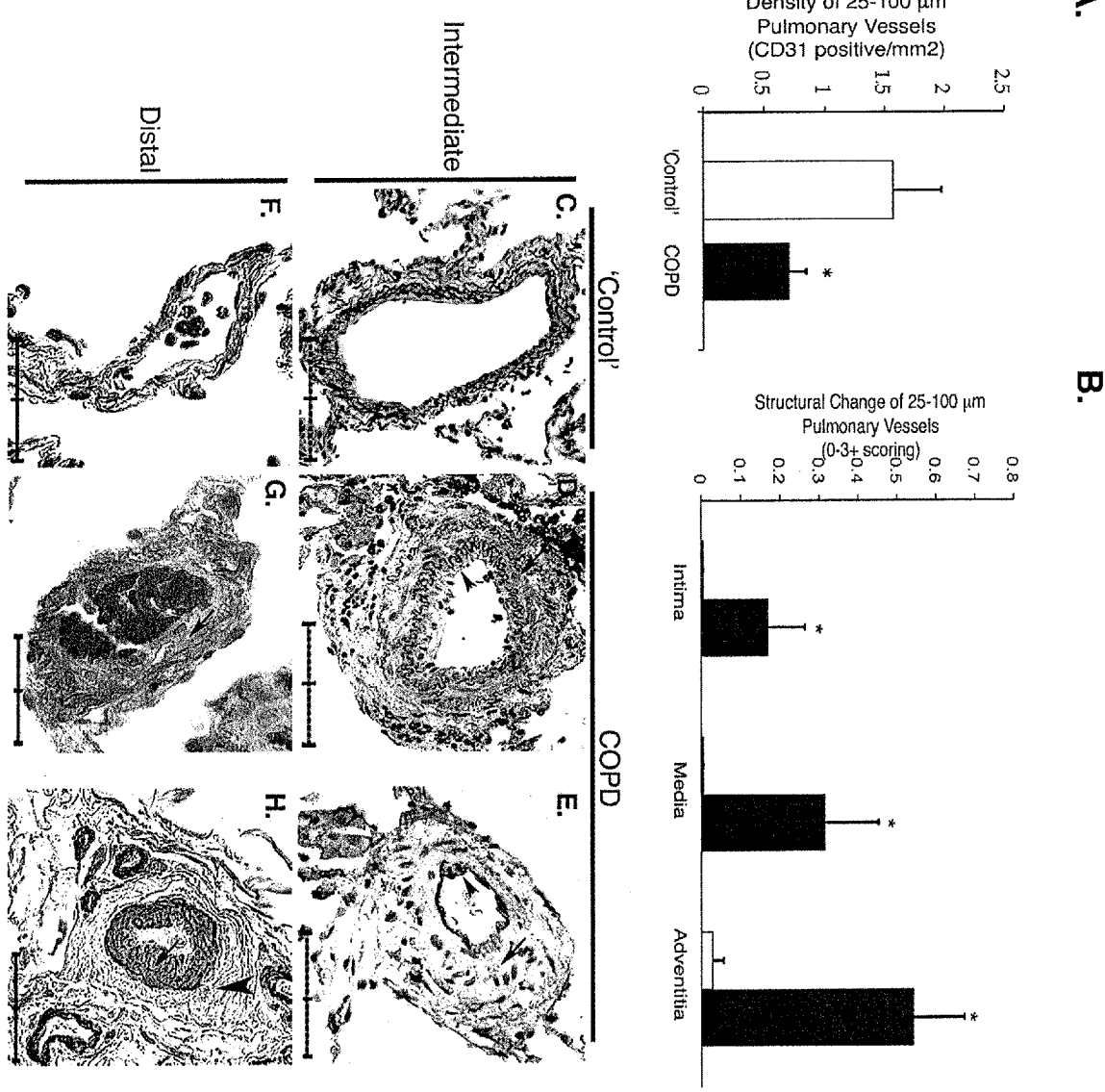
FIGS. 1A-H. Increased Vascular Remodeling in COPD vs 'Control' Lungs.

Chronic pulmonary hypertension (PHTN) is a major clinical problem, in the general and Veteran populations, and complicates most lung and heart disorders, including chronic obstructive pulmonary disease (COPD). Many factors, including cigarette smoke (CS), oxidant stress, inflammation and eventually hypoxia, contribute to the observed vascular dysfunction and remodeling in this form of chronic PHTN. Proliferation of pulmonary artery (PA) smooth muscle cells (SMCs) at the medial/adventitial border and migration to more distal sites are prominent features of the structural change.

Neprilysin (NEP) is a transmembrane protein with a cell surface peptidase activity that degrades select pro- and anti-inflammatory neuropeptides and may take part in signaling cascades by directly coupling to intracellular proteins via peptidase-independent mechanisms. Novel substrates of NEP have also recently been described. There is growing evidence that lung NEP activity and expression decrease in response to chronic CS and hypoxia by as yet unknown mechanisms.

The inventor investigated whether a reduction in NEP occurs in human lungs with smoke and hypoxia-induced vascular remodeling, similar to that observed in hypoxic mice (Dempsey et al., 2009). As a control, dipeptidyl peptidase IV (DPPIV, CD26) also was analyzed; this peptidase is also widely expressed, including in the pulmonary vasculature. Its structure is similar to that of NEP (Mentlein, 2004; van der Velden and Hulsmann, 1999); the two enzymes share some substrates, but others are unique (Gourlet et al., 1997; Lambeir et al., 2001; Mentlein, 1999). In contrast to NEP, DPPIV inhibition may promote lung function (Jung et al., 2006). DPPIV's involvement in COPD or PHTN is unknown. Advanced COPD lungs were obtained from patients with $FEV_1 < 30\%$, as worsening PHTN has been associated with decreased FEV (Thabut et al., 2005; Scharf et al., 2002). The inventor measured NEP activity, protein, and mRNA in human lung samples and PA SMCs exposed to CS extract (CSE), hypoxia, and hydrogen peroxide ($H_2O_2$). Further mechanisms relevant to COPD-associated PHTN, including oxidant effects on NEP activity and protein degradative changes, were studied in human PA SMCs.

The findings presented here suggest that lung NEP levels may be predictive of susceptibility to pulmonary vascular remodeling and PHTN in COPD, and that higher levels may protect against vascular injury induced by chronic CS and hypoxia. These results, some of which have been reported in the form of abstracts (Wick et al., 2007; Wick et al., 2009; Wick et al., 2010), may lead to novel preventions, tests, and treatments.

The inventor now has evidence that NEP is also selectively reduced in lungs of patients with advanced COPD. NEP null mice have exaggerated pulmonary vascular remodeling and PHTN in response to chronic hypoxia, and resident PA SMCs have increased growth compared to their wild-type counterparts. The decrease in human and mouse NEP is most striking in distal vessels where early PA SMC proliferation and migration occurs. The inventor has also observed that CS extract (CSE) and hypoxia decrease NEP activity and expression in isolated human and mouse PA SMCs. These observations support the idea that NEP exerts a protective effect on the lung circulation and is a disease modifying gene for chronic forms of PHTN.

I. NEPRILYSIN

Neprilysin, also known as membrane metallo-endopeptidase, neutral endopeptidase (NEP), CD10, and common acute lymphoblastic leukemia antigen (CALLA), is a zinc-dependent metalloprotease enzyme that degrades a number of small secreted peptides, most notably the amyloid beta peptide whose abnormal misfolding and aggregation in neural tissue has been implicated as a cause of Alzheimer's disease. Synthesized as a membrane-bound protein, the neprilysin ectodomain is released into the extracellular domain after it has been transported from the Golgi apparatus to the cell surface. In neurons, neprilysin is regulated by the protein nicastrin, a component of the gamma secretase complex that performs a necessary step in processing amyloid precursor protein to amyloid beta.

Mutations in the neprilysin gene have been associated with familial forms of Alzheimer's disease, and neprilysin-deficient knockout mice show both Alzheimer's-like behavioral impairment and amyloid-beta deposition in the brain, providing strong evidence for the protein's association with the Alzheimer's disease process. Because neprilysin is thought to be the rate-limiting step in amyloid beta degradation, it has been considered a potential therapeutic target; compounds such as the peptide hormone somatostatin have been identified that increase the enzyme's activity level. One hypothesis for the strong dependence of Alzheimer's incidence on age focuses on the declining production of somatostatin the brains of elderly people, which thus depresses the activity of neprilysin and promotes aggregation of unprocessed amyloid beta. Declining neprilysin activity with increasing age may also be explained by oxidative damage, known to be a causative factor in Alzheimer's disease; higher levels of inappropriately oxidized neprilysin have been found in Alzheimer's patients compared to cognitively normal elderly people.

A. Features of the Polypeptide

The sequence for Neprilysin is found at NP_000893 and in SEQ ID NO:1. When the present application refers to the function of Neprilysin or "wild-type" activity, it is meant that the molecule in question has the zinc peptidase activity. The first 27 or 28 amino acids are cytosolic, with the next 22-24 amino acids representing the transmembrane domain. The peptidase domain lies in the remainder of the molecule, with a mutation that destroys peptidase activity being E585V.

B. Variants of Neprilysin

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent or improved molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventor that various changes may be made in the DNA sequences of genes without appreciable loss of their biological utility or activity, as discussed below. Table 1 shows the codons that encode particular amino acids.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |

TABLE 1-continued

| Amino Acids | | | Codons |
|---|---|---|---|
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Specific variants of Neprilysin include a shortened secretory form can be generated with a construct that encodes only the ectodomain of the enzyme and thus does not get inserted in cell membrane. Also, fragments of interest include a peptidase domain that degrades selected neuropeptides and other proteins like FGFs. There is a transmembrane domain that may interect with other membrane proteins and anchors the enzyme, and an intracellular domain that may directly tether or inhibit intracellular signaling proteins.

Another embodiment for the preparation of polypeptides according to the invention is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of Neprilysin, but with altered and even improved characteristics.

C. Purification of Proteins

It will be desirable to purify Neprilysin or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fuctose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

D. Synthetic Peptides

The present invention also describes smaller Neprilysin-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

E. Antigen Compositions

The present invention also provides for the use of Neprilysin proteins or peptides as antigens for the immunization of animals relating to the production of antibodies. It is envisioned that either Neprilysin, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

II. NUCLEIC ACIDS

The mRNA sequence encoding Neprilysin is provided at NM_000902 and in SEQ ID NO:2. The present invention is not limited in scope to this sequence, however, as one of ordinary skill in the could readily identify related homologs in various other species (e.g., mouse, rat, rabbit, dog, monkey, gibbon, chimp, ape, baboon, cow, pig, horse, sheep, cat and other species).

In addition, it should be clear that the present invention is not limited to the specific nucleic acids disclosed herein. As discussed below, a "Neprilysin gene" may contain a variety of different bases and yet still produce a corresponding polypeptide that is functionally indistinguishable from, and in some cases structurally identical to, the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of Neprilysin.

A. Nucleic Acids Encoding Neprilysin

Nucleic acids according to the present invention may encode an entire Neprilysin gene, a domain of Neprilysin that expresses a enzyme function, or any other fragment of the Neprilysin sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given Neprilysin from a given species may be represented by natural variants that have slightly different nucleic acid sequences but, nonetheless, encode the same protein (see Table 1, above).

As used in this application, the term "a nucleic acid encoding a Neprilysin" refers to a nucleic acid molecule that has been isolated free of total cellular nucleic acid. In certain embodiments, the invention concerns a nucleic acid sequence essentially as set forth in SEQ ID NO:2. The term "as set forth in SEQ ID NO:2" means that the nucleic acid sequence substantially corresponds to a portion of SEQ ID NO:2. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:2. Sequences that are essentially the same as those set forth in SEQ ID NO:2 also may be functionally defined as sequences that are capable of hybridizing to a nucleic acid segment containing the complement of SEQ ID NO:2 under standard conditions.

The DNA segments of the present invention include those encoding biologically functional equivalent Neprilysin proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses nucleice acids that are complementary, or essentially complementary, to the sequence set forth in SEQ ID NO:2. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 under relatively stringent conditions such as those described herein. Such sequences may encode the entire Neprilysin protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to Neprilysin or, more particularly, homologs of Neprilysin from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Vectors for Cloning, Gene Transfer and Expression

Within certain embodiments, expression vectors are employed to express the Neprilysin polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example is the native Neprilysin promoter. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |

TABLE 2-continued

Promoter and/or Enhancer

| Promoter/Enhancer | References |
|---|---|
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| $\beta$-Interferon | poly(rI) × poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| $\alpha$-2-Macroglobulin | IL-6 | Kunz et al., 1989 |
| Vimentin | Serum | Rittling et al., 1989 |
| MHC Class I Gene H-2$\kappa$b | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |

TABLE 3-continued

Inducible Elements

| Element | Inducer | References |
| --- | --- | --- |
| Tumor Necrosis Factor | PMA | Hensel et al., 1989 |
| Thyroid Stimulating Hormone α Gene | Thyroid Hormone | Chatterjee et al., 1989 |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference.)

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors.

In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The ψ sequence is required for the packaging of the adenoviral genome.

A common approach for generating an adenoviruses for use as a gene transfer vector is the deletion of the E1 gene (E1), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The EY, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or subgroups A-F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors.

In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. No. 5,858,744; U.S. Pat. No. 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. No. 5,955,331; U.S. Pat. No. 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado et al., 1999; Engel and Kohn, 1999), cancer (Clay et al., 1999), cerebrovascular disease (Weihl et al., 1999) and hemophilia (Kay, 1998).

Herpesviral Vectors.

Herpes simplex virus (HSV) type I and type II contain a double-stranded, linear DNA genome of approximately 150 kb, encoding 70-80 genes. Wild-type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Gamido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors.

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence; such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors.

The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference). In other embodiments, sindbis viral vectors are contemplated for use in gene delivery.

Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors.

Chimeric or hybrid viral vectors are being developed for use in therapeutic gene delivery and are contemplated for use in the present invention. Chimeric poxyiral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection:

In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

Electroporation.

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate.

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading.

Additional embodiments of the present invention include the introduction of a nucleic acid by direct sonic loading. LTK-negative fibroblasts have been transfected with the thymidine kinase gene by sonication loading (Fechheimer et al., 1987).

Liposome-Mediated Transfection.

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium.

They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection:

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

III. ANTIBODIES REACTIVE WITH NEPRILYSIN

In another aspect, the present invention contemplates an antibody that is immunoreactive with a Neprilysin molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Neprilysin-related antigen epitopes. Additionally, it is proposed that monoclonal antibodies specific to the particular Neprilysin of different species may be utilized in other useful applications In general, both polyclonal and monoclonal antibodies against Neprilysin may be used in a variety of embodiments. For example, they may be employed in antibody cloning protocols to obtain cDNAs or genes encoding other Neprilysin. They may also be used in inhibition studies to analyze the effects of Neprilysin related peptides in cells or animals. Anti-Neprilysin antibodies will also be useful in immunolocalization studies to analyze the distribution of Neprilysin during various cellular events, for example, to determine the cellular or tissue-specific distribution of Neprilysin polypeptides under different points in the cell cycle. A particularly useful application of such antibodies is in purifying native or recombinant Neprilysin, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

IV. DIAGNOSING DISEASES INVOLVING NEPRILYSIN

Neprilysin and the corresponding gene may be employed as a diagnostic or prognostic indicator of pulmonary vascular remodeling, dysfunction and pulmonary hypertension complicating any lung or heart disorder; also idiopathic forms of pulmonary vascular disease. The lung disorders would include any form of acute and chronic lung injury and inflammation (like ARDS, ILD, pneumonia, COPD, asthma). The lung disorders also include any other primary lung vascular disorders (like idiopathic, collagen vascular-associated, liver disease-associated, drug-associated, HIV-associated, blood clot-induced pulmonary hypertension). Other conditions include low oxygen disorders such as residence at high altitude, sleep disorders, and blunted ventitlatory drive which cause hypoxic pulmonary hypertension. Heart disorders would include those that cause abnormal increases in vascular flow (congenital heart disease) and pressure (systolic and diastolic dysfunction of any cause; valvular heart disease).

More generally, one may wish to diagnose pulmonary hypertension prior to a therapy according to the present invention. Pulmonary hypertension is caused by progressive structural changes in the lung vasculature (i.e., "pulmonary vascular remodeling") and increased pulmonary vasoconstriction. Rest pulmonary hypertension is not detectable until there is substantial remodeling of the pulmonary vascular bed or loss of the vascular bed (as results from pneumonectomy). Pulmonary vascular remodeling and pulmonary hypertension are usually diagnosed initially based on clinical suspicion and accumulating indirect evidence. The evidence includes a clinical history of unexplained shortness of breath, lack of lung parenchymal abnormalities to explain it, unexplained decline in oxygen saturation with exercise, accentuation of the pulmonic component of the second heart sound on exam, physical findings of right heart dysfunction due to strain from elevated pulmonary artery pressures, enlargement of proximal pulmonary arteries on chest imaging, unexplained reduction in diffusion capacity on pulmonary function testing, elevation of brain naturetic peptide level in serum, and elevated estimate of pulmonary artery pressures on cardiac ultrasound. In selected cases, the diagnosis needs to be confirmed and directly quantitated by right heart catheterization. Lung tissue either from biopsy, resection or transplant is rarely available at time of diagnosis, but if available, tissue analysis reveals vascular remodeling before pressure elevation is detectable.

A. Genetic Diagnosis

One embodiment of the instant invention comprises a method for detecting levels of expression of Neprilysin. The biological sample can be lung tissue generally, or pulmonary arterial smooth muscle in particular. mRNA is isolated from cells contained in such samples, according to standard methodologies (Sambrook et al., 1989). In one embodiment, the RNA is whole cell RNA; in another, it is poly-A RNA. Normally, the mRNA is amplified, and may be converted to cDNA for ease of handling.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994). Following detection, one may compare the results seen in a given patient with a statistically significant reference group of normal patients and patients that have Neprilysin-related pathologies. In this way, it is possible to correlate the amount or kind of Neprilysin detected with various clinical states.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process. In particular embodiments, the probes or primers are labeled with radioactive species ($^{32}P$, $^{14}C$, $^{35}S$, $^{3}H$, or other label), with a fluorophore (rhodamine, fluorescein) or a chemilluminscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCRT™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single-stranded DNA, which is then converted to double stranded DNA, and then transcribed once again with an RNA polymerase such as T7 or SP6. The resulting products, whether truncated or complete, indicate target specific sequences.

Davey et al., EP 0 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the Neprilysin gene that may then be analyzed by direct sequencing.

(vi) Kit Components

All the essential materials and reagents required for detecting and sequencing NEPRILYSIN and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5- to 100-fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventor is chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the Neprilysin content of healthy and diseased tissues, through techniques such as ELISAs and Western blotting. This may provide a screen for the presence or absence of any of the diseases set out above.

The use of antibodies of the present invention, in an ELISA assay is contemplated. For example, anti-Neprilysin antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a nonreactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Neprilysin that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody. Also contemplated are competitive formats, with labeled and unlabeled antibodies competing for antigen.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. METHODS OF THERAPY

The present invention also involves, in another embodiment, the treatment of disease, including pulmonary vascular remodeling, dysfunction and pulmonary hypertension complicating any lung or heart disorder; also idiopathic forms of pulmonary vascular disease. The lung disorders would include any form of acute and chronic lung injury and inflammation (like ARDS, ILD, Pneumonia, COPD, Asthma). The lung disorders also include any other primary lung vascular disorders (like Idiopathic, Collagen Vascular Associated, Liver Disease Associated, Drug Associated, HIV Associated, Blood Clot Induced Pulmonary Hypertension). Other conditions include low oxygen disorders such as Residence at High Altitude, Sleep Disorders, and Blunted Ventitlatory Drive which cause Hypoxic Pulmonary Hypertension. Heart Disorders would include those that cause abnormal increases in vascular flow (Congenital Heart Disease) and pressure (Systolic and Diastolic Dysfunction of any Cause; Valvular Heart Disease).

A. Genetic Based Therapies

In one embodiment, the present inventor intends to provide, to a target, an expression construct capable of providing Neprilysin to that cell. The lengthy discussion of expression vectors and the genetic elements employed therein is incorporated into this section by reference. Particularly contemplated expression vectors are viral vectors such as adenovirus, adeno-associated virus, herpesvirus, vaccinia virus and retrovirus. Also preferred is liposomally-encapsulated expression vector, optionally a non-viral vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

B. Protein Therapy

Another therapy approach is the provision, to a subject, of Neprilysin polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

C. Combined Therapy

To improve the effectiveness of Neprilysin, one may contact a target cell with a Neprilysin expression construct/Neprilysin and at least one other agent. These compositions would be provided in a combined amount effective to improve at least one symptom associated with the disease to be treated. This process may involve contacting the cells with the expression construct/protein and the second agent(s) or factor(s) at the same time. This may be achieved by contacting the cell with a single composition or pharmacological formulation that includes both, or by contacting the cell with two distinct compositions or formulations, at the same time, wherein one composition includes the expression construct/protein and the other includes the other agent.

Alternatively, the Neprilysin therapy may precede or follow the other agent treatment by intervals ranging from minutes to weeks. In embodiments where the other agent and Neprilysin therapy are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either Neprilysin or the other agent will be desired. Various combinations may be employed, where Neprilysin or an expression construct encoding Neprilysin is "A" and the other agent is "B," as exemplified below:

```
A/B/A  B/A/B  B/B/A  A/A/B  B/A/A A/B/B  B/B/B/A B/B/A/B

A/A/B/B A/B/A/B  A/B/B/A B/B/A/A B/A/B/A B/A/A/B B/B/B/A

A/A/A/B B/A/A/A  A/B/A/A A/A/B/A A/B/B/B B/A/B/B B/B/A/B
```

Other combinations are contemplated.

Agents or factors suitable for use in a combined therapy are brochodilators, β2 agonists, anticholinergics, corticosteroids, phosphodiesterase type 5 inhibitors, endothelin receptor antagonists, prostagladins, diuretics, acetylcholinesterase inhibitors, anticoagulants and supplemental oxygen.

D. Formulations and Routes for Administration to Patients

Where clinical applications are contemplated, it will be necessary to prepare pharmaceutical compositions—expression vectors, virus stocks, proteins, drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, aerosol, intramuscular, intraperitoneal or intravenous injection. Such compositions would normally be administered as pharmaceutically acceptable compositions, described supra. Of particular interest is inhalation administration by aerosol, and an exemplary technology is Cape et al. (2008).

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Such powders are advantageously used for inhalation therapies.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The agents of the present invention may further be modified for delivery by encapsulating or embedding in a delivery vehicle. For example, liposomes, which are artificially prepared vesicles made of lipid bilayers have been used to delivery a variety of drugs. Liposomes can be composed of naturally-derived phospholipids with mixed lipid chains (like egg phosphatidylethanolamine) or other surfactants. In particular, liposomes containing cationic or neutural lipids have been used in the formulation of drugs. Liposomes should not be confused with micelles and reverse micelles composed of monolayers, which also can be used for, delivery.

Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate and polylactic-co-glycolic acid, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

Both liposomes and nanoparticles/nanoshells/nanobeads can be further modified to have additional desirable properties. For example, masking agents such as polyethylene glycol ("PEG-ylation") can be employed to reduce clearance of the agents. Also, targeting agents such as antibodies and receptor ligands may be introduced to increase the delivery of the active agent to target sites in the patient. In particular, the surface of the particles are modified with agents that facilitate targeting of endothelial cells, smooth muscle cells or fibroblasts, including but not limited to lectins (especially, from *Griffonia simplicifolia*), P-selectin, von Willebrand Factor, N-cadherin, and activated leukocyte cell adhesion molecule (ALCAM).

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Human Lung Tissue.

'Control' and COPD ($FEV_1$% of predicted=>80 and <30, respectively) frozen lungs and slides were from the UC Denver COPD Center (early samples), NIH Lung Tissue Research Consortium (LTRC; world-wide-web at ltrcpublic.com; Tissue Core Director, Dr. C. Cool), or ILD Program, National Jewish Health, Denver (NJH). Sample processing conformed to LTRC guidelines. Samples frozen in RNAlater® (Ambion) were from the LTRC and NJH. Sections were reviewed by a lung pathologist, Dr. C. Cool, to verify designations. COMIRB exemption #07-0791.

Immunohistochemistry.

'Control' or COPD sections (4 µm), were fixed in 10% formalin and embedded in paraffin at the LTRC, UCD or NJH sites, as per LTRC guidelines; because the LTRC Tissue Core is located at UCD, local samples were also handled in the same way. Staining was performed equivalently with all slides (Dempsey et al., 2009), with anti-human NEP (56C6, Fitzgerald, 1:100, following preliminary serial dilution), nitrotyrosine (Upstate, 1:100), CD31 (PECAM-1, Santa Cruz, 1:100), or α-SM actin (Thermo, 1:2); counterstain was hematoxylin.

Pulmonary Vascular Remodeling and NEP Scoring.

Distal (25-100 μm) PA (5/lung) were scored 'blindly', 0-3+, by a lung pathologist for intimal, medial, and adventitial structural changes on H&E-stained slides. Additional morphometric analysis (Littler et al., 2005) (Stereo Investigator, MBF Bioscience) was performed on pentachrome-stained (Cool et al., 2006) slides. Density of distal pulmonary arteries was measured in CD31-stained, similarly inflated, areas. For evaluation of NEP-stained slides, intensity in the alveolar walls and distal vessels (9 areas/lung) was scored blindly, 0-4+ (Dempsey et al., 2009).

Western and Activity Analyses.

Lung samples (~50 mg) or PA SMCs were homogenized in 0.5 ml 20 mM MES, pH 6.5, containing protease inhibitors, and for PA SMCs, 0.5% CHAPS. After centrifugation (10,000×g, 10 min), supernatant was stored at −80° C. NEP activity was measured as described (Dempsey et al., 2009). DPPIV activity was measured by DPPIV-Glo Protease Assay (Promega). Western analyses (Dempsey et al., 2009) with anti-human NEP (56C6, Neomarkers) were assessed by densitometry. Routine examination of Coomassie-Blue-stained blots assured sample integrity, equal loading and transfer.

Transcriptional Analysis.

DNase-treated RNA of samples in RNAlater®, or of PA SMCs, was isolated with the RNeasy kit (Qiagen). Human mRNA was semiquantitated as described (Pfaffl, 2001, in triplicateXtwo, by real-time PCR (iCycler IQ, BioRad). Reactions (25 μl), containing 0.25 μg cDNA (iScript, Bio-Rad), 0.1 μM primers, and iQ SYBR Green Supermix (BioRad), were amplified by 40 cycles of 15 sec at 94° C., 30 sec at 55° C., and 30 sec at 72° C. NEP primers were from Qiagen (QT00048755); reference was β-actin (sense, 5'-GGTG-GCTTTTAGGATGGCAAG-3' (SEQ ID NO:3); antisense, 5'-ACTGGAACGGTGAAGGTGACAG-3' (SEQ ID NO:4)). Melting curves established product specificity.

Inactivation of NEP Activity by $H_2O_2$.

Incubations of human rNEP (R&D Systems) with varying concentrations of $H_2O_2$, or of 'Control' human lung homogenates with 100 μM $H_2O_2$, were conducted for 24 h at 37° C., diluted 40-60-fold, and assayed for remaining NEP activity (Shinall et al., 2005).

Human PA SMC.

PA SMCs were isolated from the main PA of 'normal' human tissue donors (Clonetics®, Basel, Switzerland, α-SM actin positive, Factor VIII negative). Passages 6-10 were maintained in SmBM® (5% FBS), at 37° C., and used for experimentation. Cells were made quiescent with 0.1% FBS and exposed to normoxia (20% $O_2$), 5 μg/ml CSE (Murty Pharmaceuticals, Lexington, Ky.), hypoxia (3% $O_2$), or 100 μM $H_2O_2$ at 37° C. for 4 or 48 h. The antioxidants Tiron (2.5 mM; Sigma) (Taiwo, 2008), MnTMPyp (an SOD/catalase mimetic (Day et al., 1997), 20 μM; Calbiochem), or polyethylene glycol (PEG) conjugated catalase Beckman et al., 1988) (40 units/ml; Sigma), or the protein degradation inhibitors (Folimycin Huss and Wieczorek, 2009) for lysosomes, 50 nM; Clastolactacystin β-lactone (Dick et al., 1996) for proteasomes, 1 μM; Calbiochem) were added 0.5 or 2 h, respectively, before exposures.

Statistical Analyses.

Data are mean+/−SEM. Group sizes needed were determined with PASS 2008 (NCSS, UT). Statistical significance ($p \leq 0.05$) was determined by t-test, one- or two-way analysis of variance, as appropriate (JMP, SAS Institute) (Dempsey et al., 2009).

Reagents and Antibodies.

Recombinant human NEP (rNEP) was provided by Dr. Catherine Magill, AXYS Pharmaceuticals, Inc (San Francisco, Calif.). Lentivirus expressing full length human NEP was obtained from Dr. Louis Hersh (University of Kentucky). PDGF-BB and neuropeptides were obtained from Bachem (Torrence, Calif.). Other chemicals were from Sigma (St. Louis, Mo.) unless specified. PDGFRIII antagonist was obtained from EMD Biosciences (Gibbstown N.J.). Neutralizing antibody to PDGF was obtained from R&D Systems (Minneapolis, Minn.). Antibodies used were as follows: mouse NEP from R&D Systems; calponin, SM-22 from Abcam (Cambridge, Mass.); p-PDGFR and PDGFR alpha and beta, Phospho and total PTEN and phospho and total Src from Cell Signal Technology (Danvers, Mass.); α-SM-actin and SM-myosin from Sigma Aldrich (St. Louis, Mo.).

NEP−/− Mice.

NEP−/− mice on a C57/BL6 background were originally obtained from Drs. Norma and Craig Gerard (Harvard Medical School) (Said et al., 2010). Mice were routinely out bred with C57/BL6 mice obtained from Jackson Laboratories (Bar Harbor, Me.). NEP+/+ and NEP−/− mice were obtained by heterozygous mating. NEP+/+ and NEP−/− mice were identified by PCR of genomic DNA obtained from tail samples as previously described (Petkov et al., 2003). Approval of animal protocols was obtained from the University of Colorado and Denver Va. Medical Center Institutional Animal Care and Use Committees.

Isolation and Characterization of PASMC from Adult C57 B1/6 Mice.

Mice were anesthetized with sodium pentobarbital (100 mg/kg i.p.). Proximal medial tissue was micro dissected from individual age matched 13-17 wk old NEP+/+ and NEP−/− littermate mice. Tissue was digested with collagen and cells were grown in DMEM-F-12 medium containing 10% fetal bovine serum (FBS) as described (Petkov et al., 2003). PASMCs were characterized by light microscopic appearance, growth characteristics, and stained for α-SM-actin, SM-myosin, Factor VIII and LDL between passage 3 and 6. PASMCs were used for studies between passage 6 and 13.

Scratch Assay.

Briefly, PASMCs were grown to confluence on 60 mm plates (Hamidi et al., 2008). The cells were serum starved in DMEM-F-12 medium with 0.2% serum for 24 h, and scraped with a sterile P200 pipette tip to generate a cell-free zone. PASMCs were then rinsed with medium and incubated with either 0.2% serum or 10 ng/ml PDGF-BB and cells that migrated into the scratch were visualized by light microscopic imaging. Quantitation of migration was done by counting the number of PASMCs in a 5 $cm^2$ area of the scratch. Average from three different populations was used for statistical analysis.

$^3$[H] Thymidine Incorporation.

The effects of growth factors and neuropeptides on DNA synthesis were evaluated as previously reported (Petkov et al., 2003). SMCs were grown in DMEM containing 10% FBS in 24-well plates for about 16 hr. PASMCs were then incubated in DMEM supplemented with 0.2% FBS for 24 hr to make them quiescent. Then cells were incubated with stimulants in the presence or absence of inhibitors for 24 hr. [$^3$H]-thymidine obtained from Perkin Elmer (Waltham, Mass.) at 1 mCi/ml was added for the last 6 hr. After labeling was completed, the cells were washed twice with ice-cold PBS, and proteins were precipitated with 5% perchloric acid. The precipitate was dissolved with 0.5 N NaOH and SDS and radioactivity was measured using a liquid scintillation counter made by Beckman Coulter, Inc. (Brea, Calif.).

Boyden Chamber Assay.

Migration was determined by a modified Boyden chamber assay using a polycarbonate filter with 8 μM pore diameter obtained from Neuroprobe (Gaithersburg, Md.) (Said et al., 2007). Briefly, $2\times10^4$ cells in 250 μl of serum-free DMEM were added to the top wells. The lower chamber was filled with serum or PDGF (10 ng/ml). PDGF treatment was always performed in serum-free media. The chambers were incubated at 37° C. in a 5% $CO_2$ atmosphere for 6 hr. The cells that did not migrate through the filter were removed from the insides of the inserts with a cotton swab. The cells that migrated to the underside of the membrane were fixed with methanol and stained using crystal violet. The membranes were examined under a microscope and the cells that migrated to the lower surface were counted (five random 20× fields/well).

Western Blotting.

Cell lysates were prepared in immunoprecipitation buffer (20 mM Tris HCl (pH 7.5), 150 mM NaCl, 1 mM EDTA, 10% glycerol, 1% Nonidet P-40; 1 mM dithiothreitol, 10 mM NaF, 1 mM sodium orthovanadate, 10 μg/ml leupeptin, 10 μg/ml aprotinin, 10 μg/ml pepstatin A, and 1 mM phenylmethylsulfonyl fluoride) (Petkov et al., 2003). Cells were scraped from the plates, lysed on ice for 30 min. Cellular debris was eliminated by centrifugation for 10 min at 10,000 rpm. The protein concentration was determined by the BCA protein Assay®. Proteins (20-100 μg) were separated on SDS-PAGE and transferred to nitrocellulose membranes obtained from GE Healthcare, (Piscataway, N.J.). Membranes were blocked in PBS containing 0.1% Tween-20 and 1% BSA for 1 h at room temperature. Membranes were incubated with primary antibodies overnight at 4° C., and with secondary antibodies for 1 h at room temperature. All antibodies were diluted in PBS containing 0.1% Tween 20 and 1% BSA, and ECL reagent obtained from Perkin Elmer (Waltham, Mass.) was used for immunodetection. GAPDH was used as a loading control.

Densitometry.

A Bio-Rad gel scanner and densitometer (Gel DocXR with Quantity 1 program) were used to assess the intensity of the bands obtained by Western blots. Samples from NEP+/+ and NEP−/− PASMCs were run on the same gel. The arbitrary units obtained were normalized to GAPDH and the ratios for NEP+/+ to NEP−/− PASMCs were calculated. Numbers obtained from 3-6 different isolates were used for statistical analysis.

Semi-Quantitative RT-PCR.

Total cellular RNA was extracted from NEP+/+ and NEP−/− PASMCs using a kit from Qiagen (Valencia, Calif.) as per manufacturer suggestions. cDNA was generated from RNA extracts using a reverse transcription (RT) kit from Applied Biosystems/Ambion (Austin, Tex.). Polymerase chain reaction (PCR) was done using the following primers obtained from Primer bank MGH Harvard (SM-markers) and PDGFR primer sequence was from (Said, 2008).

α-SM-actin:
(SEQ ID NO: 5)
Forward 5'-GTCCCAGACATCAGGGAGTAA-3';

(SEQ ID NO: 6)
Reverse 5'TCGGATACTTCAGCGTCAGGA-3'

SM-22α:
(SEQ ID NO: 7)
Forward 5'-CAACAAGGGTCCATCCTACGG-3';

(SEQ ID NO: 8)
Reverse 5'-ATCTGGGCGGCCTACATCA-3'.

SM-myosin:
(SEQ ID NO: 9)
Forward 5'-AAGCTGCGGCTAGAGGTCA-3';

(SEQ ID NO: 10)
Reverse 5'-CCCTCCCTTTGATGGCTGAG-3'

PDGFR-α:
(SEQ ID NO: 11)
Forward 5'-CAAACCCTGAGACCACAATG-3';

(SEQ ID NO: 12)
Reverse 5'-TCCCCCAACAGTAACCCAAG-3'

PDGFR-β:
(SEQ ID NO: 13)
Forward 5'-TGCCTCAGCCAAATGTCACC-3';

(SEQ ID NO: 14)
Reverse 5'-TGCTCACCACCTCGTATTCC-3'

GAPDH:
(SEQ ID NO: 15)
Forward 5'-GCCAAGGTCATCCATGACAAC-3';

(SEQ ID NO: 16)
Reverse 5'-GTCCACCACCCTGTTGCTGTA-3'

Annealing temperatures for the PCR reactions were as follows: 55° C. for α-SM-actin, 58° C. for SM-22α and 50° C. for SM-myosin; 55° C. for PDGFR α, PDGFR β and GAPDH. Extension time for all reactions was 3 min and 35 cycles were performed.

SiRNA Transfection.

The inventor tested three different siRNA (Novus, Santa Cruz and Sigma) for knockdown of NEP. NEP siRNA from Sigma decreased protein expression by >90%. PASMC were transfected with mouse specific siRNA for NEP or universal siRNA from Sigma Aldrich, using Dharmafect Reagent® from Dharmacon (Denver, Colo.) as per manufacturer recommendations. The final concentration of siRNA was 10 nM. Universal siRNA was used as a negative control. Cells were used 48 h after transfection for migration and proliferation assays. Protein lysates were analyzed by Western blotting to determine efficiency of knock down.

Statistical Analysis.

Data were analyzed using GraphPad Prism 4.02 for Windows (GraphPad Software for Science Inc., San Diego, Calif.). Results are presented as mean±SEM. The significance of differences between two measurements was determined by unpaired, two-tailed t-tests; one-way analysis of variance was used for multiple comparisons. $P \leq 0.05$ was considered statistically significant. The 'n' for each experiment represents number of cell isolates each obtained from a different mouse.

Example 2

Results

Human Lung Tissue.

'Control' lung tissue from tissue donors and lung lobectomies/wedge resections, was from the UC Denver COPD Center, the ILD Program (NJH) and the NIH LTRC. Advanced COPD lung tissue from transplants was from the UC Denver COPD Center and the NIH LTRC. Clinical sites were designated 'Denver' or 'near sea level', since Denver altitude (5,280 ft) impacts $PaO_2$ measurements and may subtly alter vascular structure compared to the other procurement sites. The average age of the 'Control' group (n=14) was 57.5±4.7 years, and that of the advanced COPD group (n=13) was 51.0±1.6 years. The 'Control' group contained 9 females and 5 males, 3 of whom were smokers and 11 of whom were non-smokers. The advanced COPD group contained 7 females and 6 males, 11 of whom were smokers, 1 non-smoker, and 1 with unknown smoking status. Some pulmonary function data was available for 'Control' patients from the LTRC, and for all the advanced COPD patients undergoing lung transplantation. Those 'Controls' that were tested had averages of 106.0±3.2% for $FEV_1$, 103.0±4.5% for DLCO, and 100.0±0 mm Hg for $PaO_2$. The advanced COPD group had averages of 19.3±1.2% for $FEV_1$, 31.3±5.6% for DLCO, and 58.3±3.8 mm Hg for $PaO_2$. No hemodynamic data was available for the LTRC patients, and therefore this endpoint was not included in the analysis.

Analysis of Vascular Remodeling in 'Control' versus COPD Human Lungs.

To screen for rarification of the distal lung vasculature, the inventor determined the density of distal PAs in 'Control' and advanced COPD sections. Lung sections were stained with an antibody for CD31, which stains endothelial cells. There were more CD31 positive distal, small (25-100 µm) pulmonary blood vessels per $mm^2$ in 'Control' lung sections than in comparably inflated areas of emphysematous lung in the advanced COPD sections, indicating that there had been 'dropout' or rarification of the distal lung vasculature in the COPD samples (FIG. 1A). Even in these advanced COPD samples, patchy areas of relatively normal lung parenchyma and vascular density were encountered near areas of emphysematous lung. To evaluate remodeling of the pulmonary vessel wall, H&E-stained lung sections were scored on a 0-3+ scale by a blinded lung pathologist for relative thickening of the intima, media, and adventitia of distal (25-100 µm) PAs (0 equals normal and 1, 2, and 3+ represent progressively more substantial thickening). As shown in FIG. 1B, the COPD lung sections displayed progressively more thickening of the intimal, medial, and adventitial layers of the distal pulmonary vessels (25-100 µm), compared to 'Control' samples. Additional distal vascular wall measurements using MicroBrightfield digital image analysis of pentachrome-stained sections corroborated these findings, although the magnitude of the differences was less (not shown). Examination of intermediate vessels (100-500 µm) demonstrated that there was also pulmonary vascular remodeling at this site in COPD lungs, with intimal changes being more prominent here. Medial and adventitial differences vs 'Control' were again noted but were not as substantial (not shown).

FIGS. 1C-H show representative images of intermediate (100-500 µm) and distal (25-100 µm) PAs stained with pentachrome, or with antibodies to CD31 or α-SM actin. Pentachrome staining of 'Control' vs advanced COPD lungs demonstrates intimal thickening (especially in the intermediate vessels), expansion of the medial layer between the internal and external elastic lamina, and prominent adventitia with loose yellow staining of matrix protein beyond the external elastic lamina. CD31 staining highlights the endothelium; note the lack of intimal change in the vessel shown (1E), demonstrating the variable remodeling observed at that site. Alpha-Smooth Muscle actin stain demonstrates medial and adjacent adventitial thickening in advanced COPD lungs.

NEP Activity and Expression in 'Control' and COPD Lung.

Figure 2:
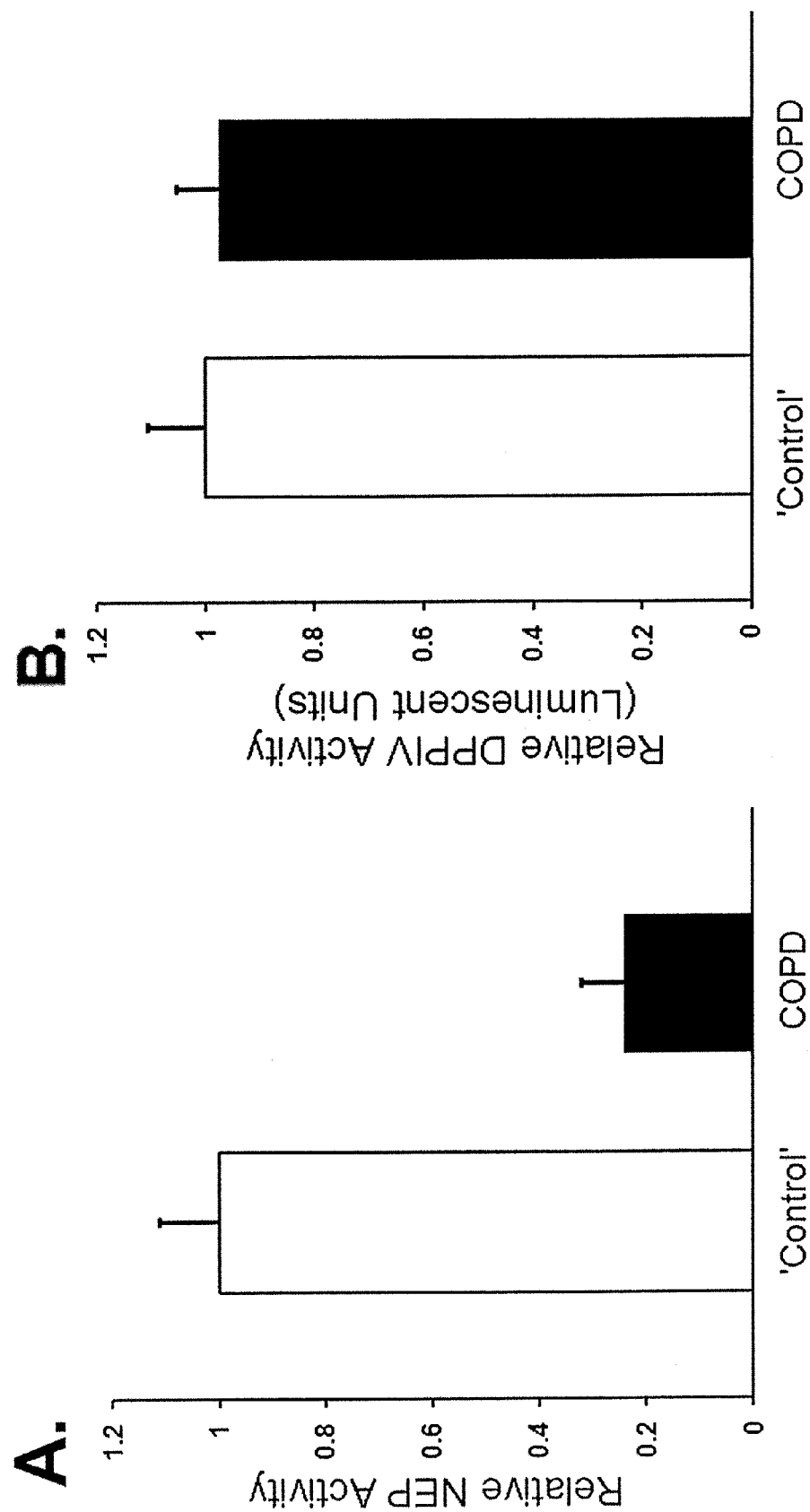
FIG. 2A-B. NEP, but not DPPIV, Activity is Reduced in Lung Lysates from COPD Patients with Pulmonary Vascular Remodeling.
Figure 3:
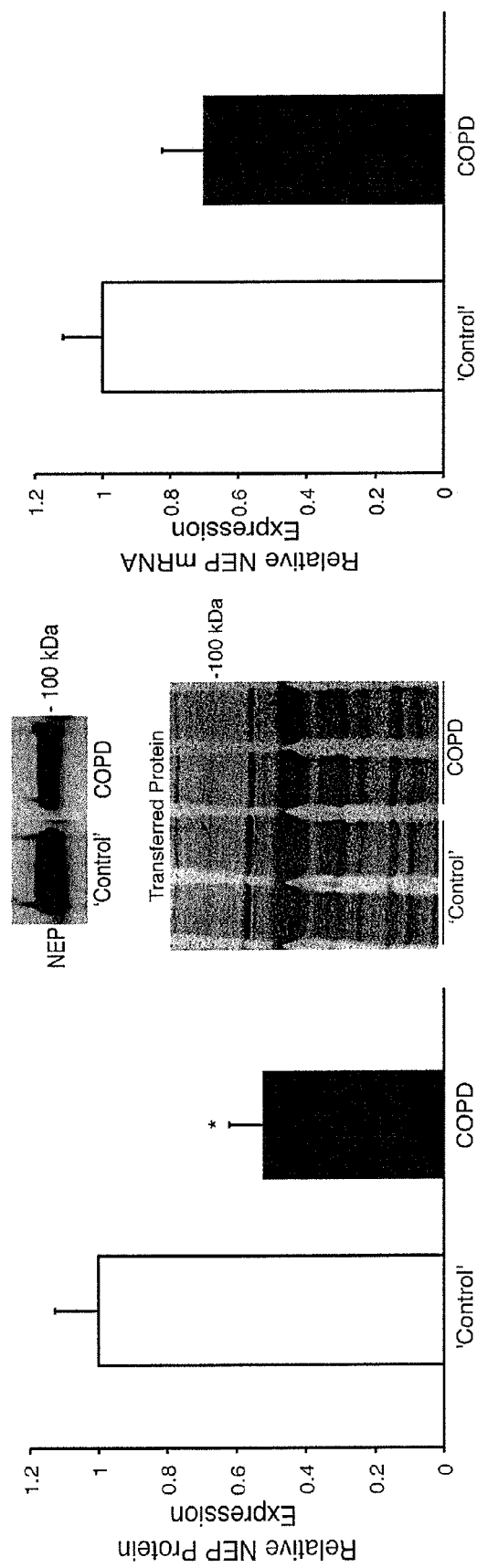
FIGS. 3A-C. NEP Protein and mRNA Expression are Reduced in Lung Lysates from Patients with COPD and Pulmonary Vascular Remodeling.

The inventor first assayed 'Control' and advanced COPD lungs for changes in NEP activity and expression. As shown in FIG. 2A, there was a 76% decrease in NEP activity between 'Control' and COPD human lung lysates. The activity of another peptidase also found within the lung, DPPIV, measured for comparison, displayed no differences, between 'Control' and COPD lung (p=NS; FIG. 2B). Results of Western analyses, summarized in FIG. 3 (left), demonstrate a 48% decrease in NEP protein expression between 'Control' and COPD samples. Representative NEP-stained Western blots and Coomassie-Blue stained nitrocellulose membranes are shown in FIG. 3 (middle). Coomassie-Blue staining was routinely used as a control for the Western blots, as well as for a check on sample and transfer integrity (Aldridge et al., 2008; Garat et al., 2006). The inventor could not detect DPPIV by Western analyses, despite using five different primary antibodies (n=16). Next, NEP mRNA levels were semiquantitated in whole lung samples (stored in RNAlater®) by qRT-PCR. As shown in FIG. 3 (right), a trend to an approximately 30% decrease in relative NEP mRNA level was observed between 'Control' and COPD samples (p=NS).

Figure 4:
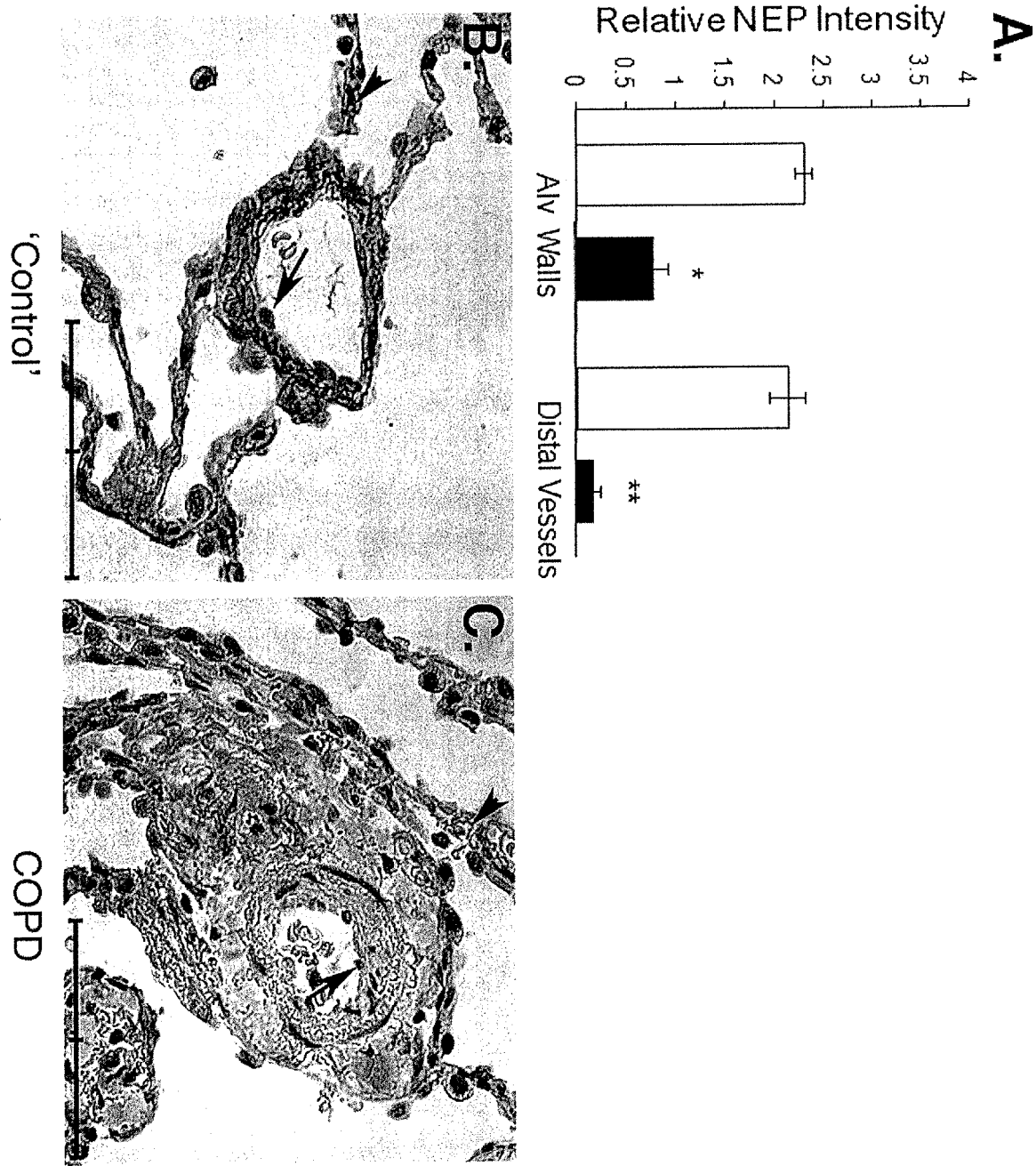
FIGS. 4A-C. NEP Expression is Decreased in Alveolar Walls and Distal (25-100 µm) Remodeled Vessels in COPD Lungs Compared to 'Control' Lungs.

Immunostaining with an NEP antibody which has been well-characterized (Dempsey et al., 2009), was used to localize the expression of NEP in the lung. In preliminary serial dilution studies, alveolar walls and distal vessels (25-100 µm) were noted to retain the strongest signal; more proximal structures had less staining than the inventor had previously observed in mice (Dempsey et al., 2009). Proximal structures in slides of peripheral human lung are really intermediate in size, and thus are different than those encountered in sections of mouse lung. A faint signal may be better appreciated without counterstain. NEP expression was widely decreased in COPD vs 'Control' lungs. The biggest differences appeared to be within alveolar walls and distal vessels, so these were studied in more detail; a 1:100 dilution of antibody was selected for comparative analysis. 'Control' and COPD samples (n=5 slides each) were evaluated in nine different areas of the slide. The intensity of NEP stain in the alveolar walls and distal vessels was scored in a blinded fashion, on a 0-4+ scale. As seen graphically in FIG. 4A, in 'Control' lungs, NEP is expressed prominently in alveolar walls and distal PAs, and expression does not vary significantly between these two areas in 'Control' lungs (2.32+/−0.09 vs 2.15+/−0.18). However, in the COPD samples, NEP expression is decreased compared to 'Control' samples, in both the alveolar walls and distal vessels. In the COPD lungs, NEP expression may vary between these two areas; NEP expression is particularly low in the distal vasculature of the COPD lungs (the site of the greatest pulmonary vascular remodeling in the COPD lungs; COPD alveolar walls=0.78+/−0.16; COPD vessels=0.16+/−0.08). FIGS. 4B-C show representative images of alveolar walls and adjacent distal vessels from slides of 'Control' and COPD lung tissue stained with this anti-NEP antibody. Preliminary examination of NEP-stained lungs from subjects with other causes of PHTN not associated with substantial parenchymal disease (including idiopathic and collagen vascular disease associated PHTN, n=6), suggested, also, that distal remodeled pulmonary vessels had decreased levels of NEP (not shown).

Consistent with the peptidase activity measurements, immunohistochemical analyses for DPPIV using two primary antibodies with different levels of stringency confirmed DPPIV protein expression was unchanged in 'Control' vs COPD lungs (n=12; not shown).

Finally, the inventor looked for potential differences in NEP activity/expression and smoking history in the 'Control' and advanced COPD groups. Among the 3 'Control' smokers, NEP activity and protein expression were reduced about 30% vs the highest 'Control' values, but NEP mRNA levels were normal. Advanced COPD non- or light smokers with confirmed (183, SO4 2570H) or suspected (294945 and 224471) α1-antitrypsin deficiency had decreases in NEP activity and expression that were consistent with what was observed with the heavier smokers within the advanced COPD group. Thus, CS probably can inhibit NEP activity and protein expression, but CS might not decrease NEP mRNA. A subtle primary or secondary smoke exposure history, increased genetic susceptibility, and ongoing inflammation and parenchymal destruction may be associated with decreases in NEP activity and both NEP protein and mRNA expression.

Figure 5:
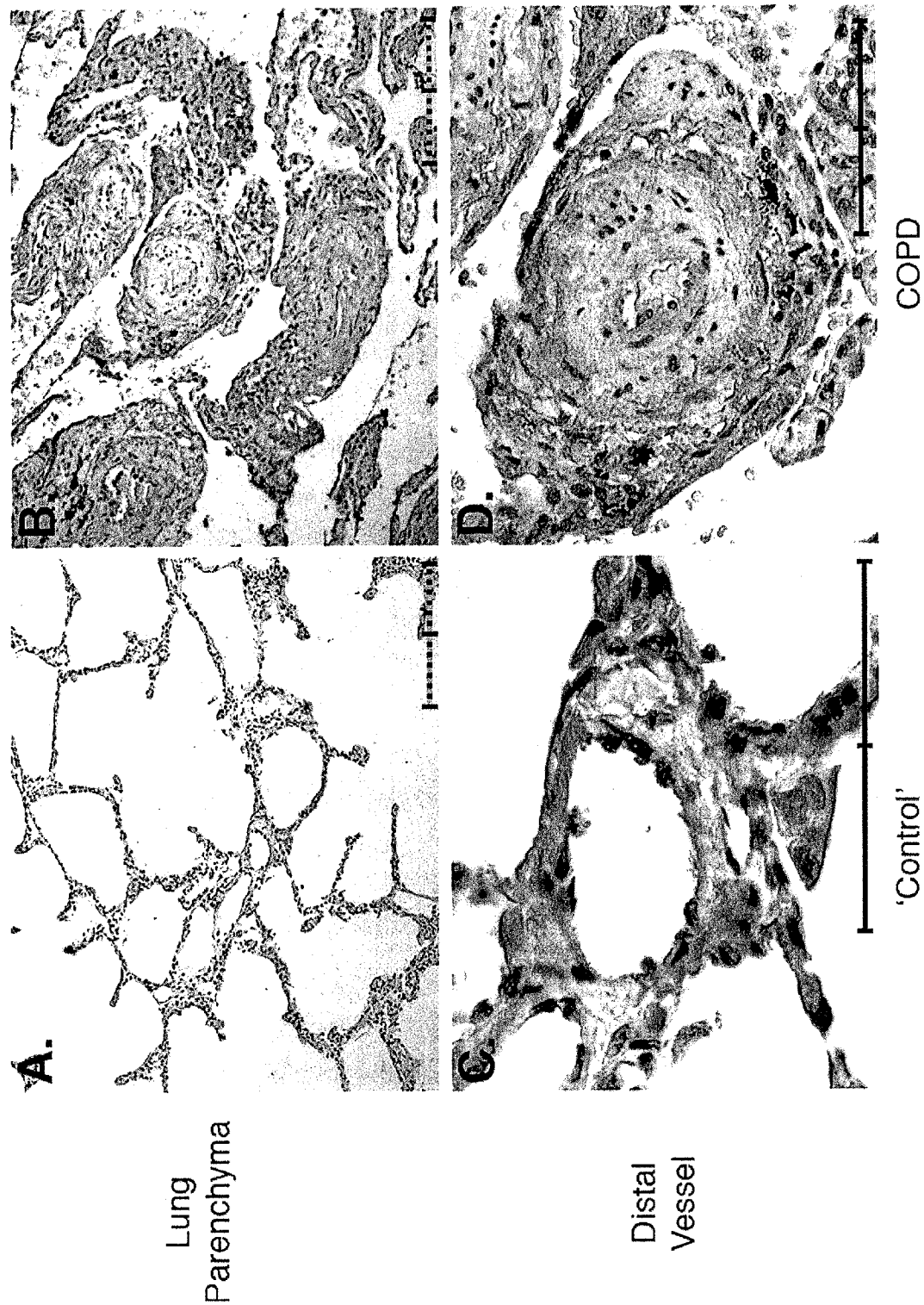
FIGS. 5A-D. Nitrotyrosine Staining for Oxidant-Damaged Proteins is Higher in COPD Lungs Compared to 'Control' Lungs. The presence of nitrotyrosine residues on proteins can be used as a marker for peroxynitrite formation, and indicates oxidant damage to proteins.

Nitrotyrosine Staining of 'Control' and COPD Lungs. To determine whether lungs from patients with advanced COPD are under increased oxidant stress, the inventor stained 'Control' and advanced COPD lung sections for nitrotyrosine residues (formed by reaction of tyrosine residues with peroxynitrite, indicating that both reactive nitrogen and reactive oxygen species have been present). Nitrotyrosine staining is widely used to indicate oxidative stress (Sultana et al., 2009; Bowers et al., 2004). As seen in FIGS. 5A-B, the COPD samples had greatly increased nitrotyrosine staining compared to 'Control' samples, indicating that the COPD lungs had been exposed to much higher levels of oxidative stress than had the 'Control' lungs. The inventor also stained 'Control' vs advanced COPD slides for 8-hydroxyguanosine residues (8-HG; formed by reaction of ROS with the DNA base guanine) and found similar results (not shown).

Reaction or Recombinant NEP and Lung Homogenates with Hydrogen Peroxide.

Figure 6:
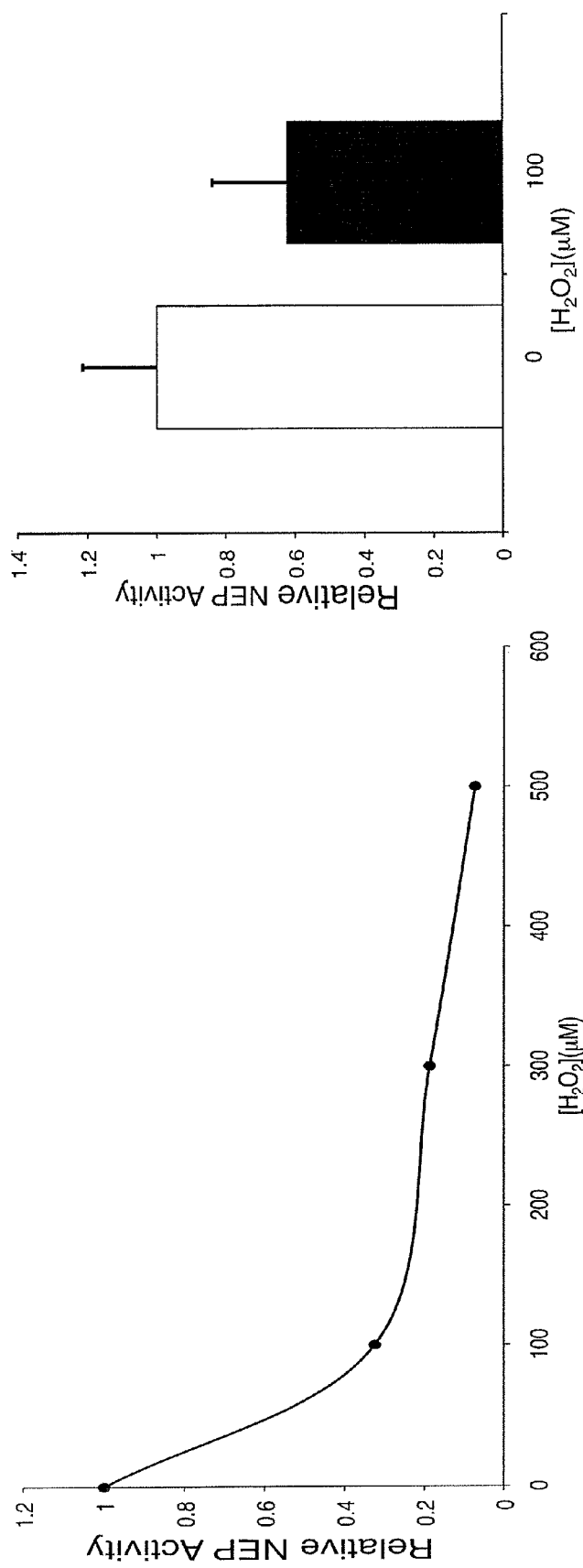
FIGS. 6A-B. NEP Activity is Susceptible to Oxidation by $H_2O_2$.

$H_2O_2$, a powerful oxidizer, was used tp determine whether oxidation by ROS inactivates or decreases NEP activity. It is important to note that the inventor used $H_2O_2$ only as a readily available, easy-to-use reagent which would model the response of NEP to a number of oxidants. As shown in FIG. 6 (left), 24 h incubation of recombinant human NEP with various concentrations of $H_2O_2$ leads to potent inactivation of residual rNEP activity (68% inhibition with 100 µM $H_2O_2$, more inhibition with higher concentrations), comparable to the results of Shinall et al. (2005). Moreover, as shown in FIG. 6 (right), NEP activity present in 'Control' crude lung homogenates is also inactivated by $H_2O_2$ (38% inhibition with 100 µM $H_2O_2$ after 24 h).

NEP Activity and Expression in Human PA SMCs.

To begin to understand some of the mechanisms responsible for the decreases in NEP activity/expression that occur in COPD lung, and to follow up on the observation that NEP expression is decreased in the distal remodeled vasculature, the inventor moved to a simplified cell system utilizing human PA SMCs. Since SMC proliferative changes have been observed at both proximal and distal sites in the pulmonary vasculature (Dempsey et al., 2010) and proximal-derived human PA SMCs are much easier to obtain, the inventor used proximal PA SMCs to complete these initial studies.

As exposure to CSE, hypoxia, and ROS may mimic some of the conditions leading to COPD and vascular remodeling in vivo, human PA SMCs were exposed to normoxia (20% $O_2$), 5 µg/ml CSE, hypoxia (3% $O_2$), or 100 µM $H_2O_2$ for 48 h, and the patterns of NEP activity, protein and mRNA expression were compared to those of 'Control' vs COPD lungs. Shown in FIG. 7A is a representative light image of human PA SMCs with characteristic spindle shape. As shown in FIGS. 7B-D, PA SMC NEP activity was decreased by 30-39% (FIG. 7B), protein expression was decreased by 28-38% (FIG. 7C), and relative mRNA levels were decreased by 11-48% (7D), compared to the normoxic control, following 48 h exposure to CSE, hypoxia, or $H_2O_2$. Note that, in vitro, NEP activity, protein expression, and mRNA expression were all decreased to about the same extents, in contrast to what was observed in vivo. Also, $H_2O_2$ did not significantly decrease NEP mRNA expression (FIG. 7D). However, in preliminary experiments, the inventor has observed a transient but significant decrease (40%) in NEP mRNA after 4 h exposure to $H_2O_2$ (not shown).

Prevention of Decreases in NEP Activity by Various Antioxidants.

Figure 8:
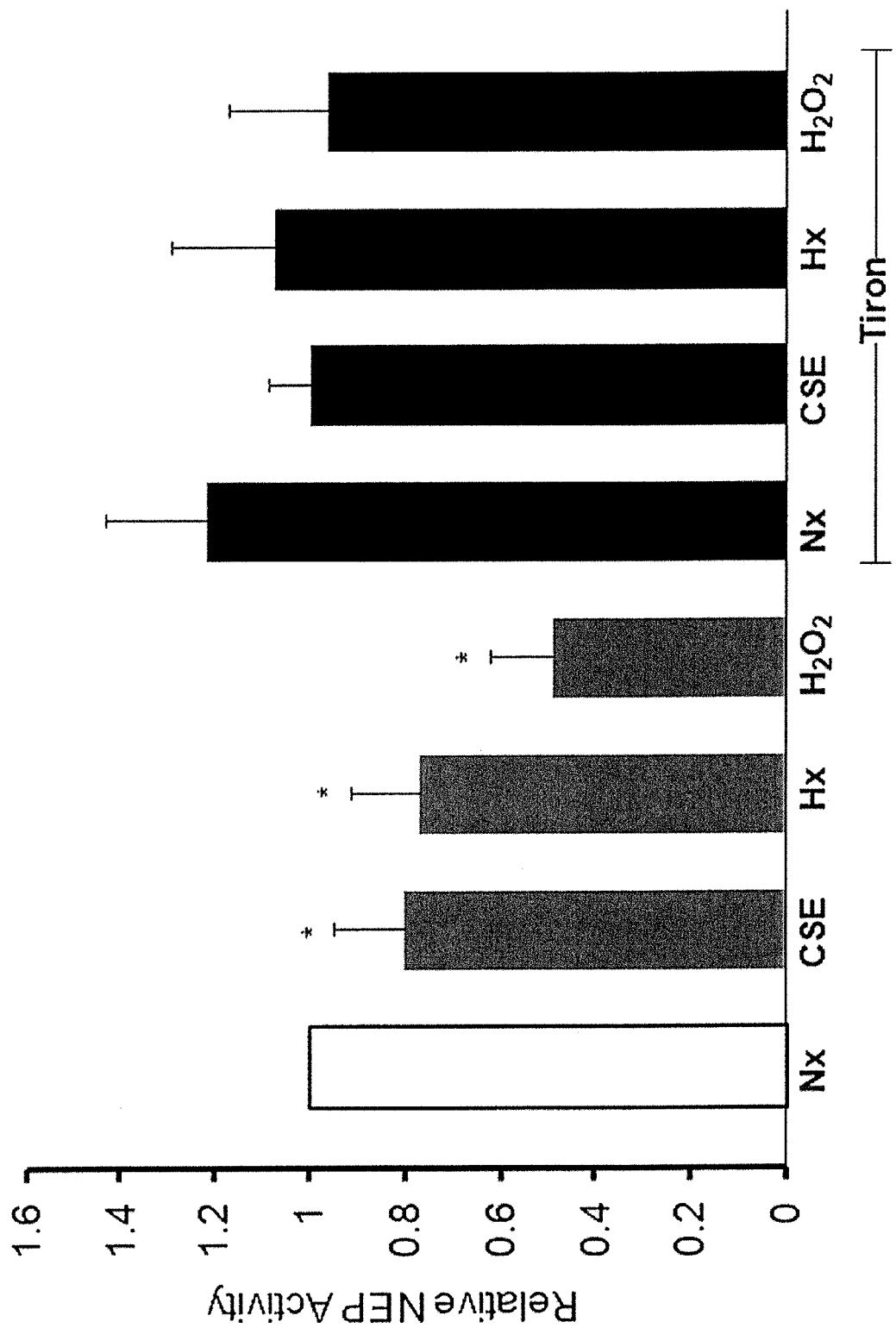
FIG. 8. Prevention of Decrease in NEP Activity by the Antioxidant, Tiron. Human PA SMCs were incubated with 2.5 mM of the antioxidant, Tiron, 0.5 h before, and throughout 4 h exposure to CSE (5 µg/ml), hypoxia (3% $O_2$; Hx), or $H_2O_2$ (100 µM). NEP catalytic activity was then determined fluorometrically. Four bars without Tiron: Nx, CSE, Hx, n=8. $H_2O_2$, n=7. Four bars with Tiron: Nx, CSE, Hx, n=4. $H_2O_2$, n=3, *p<0.05 vs Nx alone. Nx with Tiron did not differ significantly from Nx alone, nor from CSE, Hx, or $H_2O_2$ (also with Tiron).

If oxidant stress is an important mechanism for decreasing NEP activity in vivo, then an antioxidant should be able to prevent at least some of the observed decreases in PA SMC NEP activity. Therefore, human PA SMCs were incubated for 0.5 h with the antioxidant Tiron (2.5 mM) and exposed to normoxia, CSE, hypoxia, or $H_2O_2$ for 4 h, which is sufficient time to observe NEP activity, but not expression, losses. As demonstrated in FIG. 8, without Tiron, NEP activity was significantly decreased after 4 h exposure to CSE, hypoxia, and especially $H_2O_2$. All decreases in NEP activity were prevented by the antioxidant, Tiron. An additional experiment was performed in the same manner with the antioxidants Tiron, MnTMPyp (a dual superoxide dismutase (SOD)/catalase mimetic) (Day et al., 1997) and polyethylene glycol (PEG) conjugated catalase, to address how Tiron, which is known for its SOD mimetic properties, may reverse the effects of $H_2O_2$ on NEP activity. All three antioxidants (MnTMPyp, PEG-catalase, and Tiron) prevented $H_2O_2$-induced decreases in PA SMC NEP activity (not shown).

Prevention of NEP Protein Degradation by Lysosomal and Proteasomal Inhibitors.

Because COPD lung NEP protein expression is decreased more than is NEP mRNA expression (48% vs 30%; FIG. 3 (left and right), a mechanism in COPD lung which may be involved in this differential effect is an increase in NEP protein degradation. Because NEP is a membrane protein, the inventor considered both lysosomal and proteasomal protein degradation mechanisms. Following serum withdrawal, human PA SMCs were pre-incubated for 2 h with the lysosomal protein degradation inhibitor Folimycin (50 nM) and exposed to normoxia, CSE, hypoxia, or $H_2O_2$, for 48 h. Cell lyates were then examined for NEP protein expression by Western analysis. Although Folimycin did not have much effect on NEP protein expression under normoxic conditions, it provided nearly complete protection to the NEP protein from CSE or hypoxia exposure, while protection from $H_2O_2$ exposure was somewhat weaker (10-40%; not shown). Similar experiments conducted with the proteasomal protein degradation inhibitor Clastolactacystin β-lactone (1 µM) indicated that this inhibitor provided only partial protection to the NEP protein (20-65%) from all three types of exposures (CSE, hypoxia or $H_2O_2$; not shown).

Prevention of Enhance Migration and Proliferation of PASMCs, and Increase of SRF and SM Contractile Proteins by Restoration of NEP Protein.

PASMCs isolated from NEP−/− mice exhibited enhanced migration and proliferation in response to serum and PDGF, which was attenuated by adding back NEP. NEP−/− cells had decreased levels of serum response factor (SRF) and smooth muscle (SM) contractile proteins (alpha (α)-SM-actin, calponin and SM-22), which were restored by NEP. Inhibition of NEP in NEP+/+ cells by phosphoramidon or knock down by siRNA resulted in an increase in basal migration and proliferation and a decrease in expression of SM contractile proteins. Further analysis showed that loss of NEP led to increase in PDGF receptor (PDGFR) associated src kinase activity and inactivation of PTEN by phosphorylation resulting in its constitutive activation. Inhibition of PDGFR attenuated the increased migration and proliferation and restored expression of SRF and α-SM-actin.

[Next Sections Use Ref Set A]

Loss of NEP Leads to Increased Migration and Proliferation of PASMC.

Figure 9E:
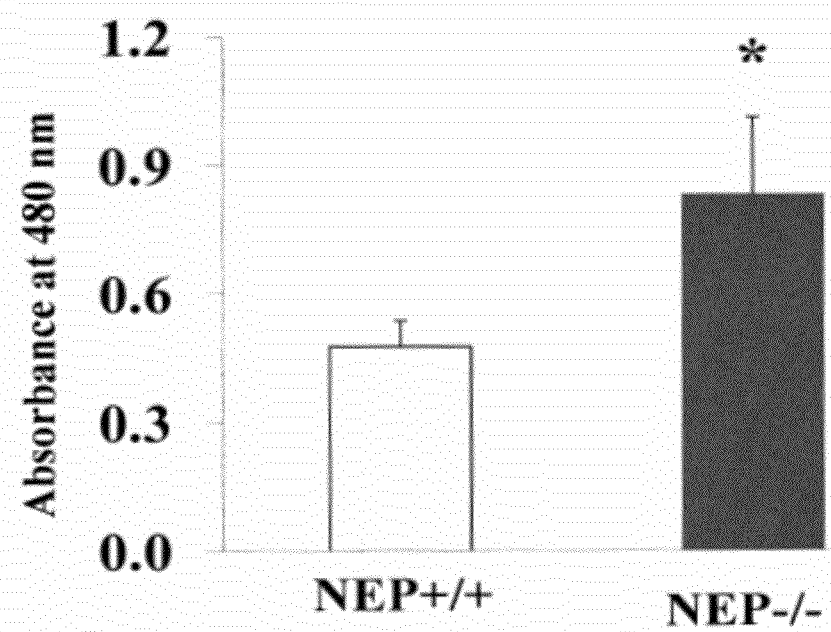
Figure 11C:
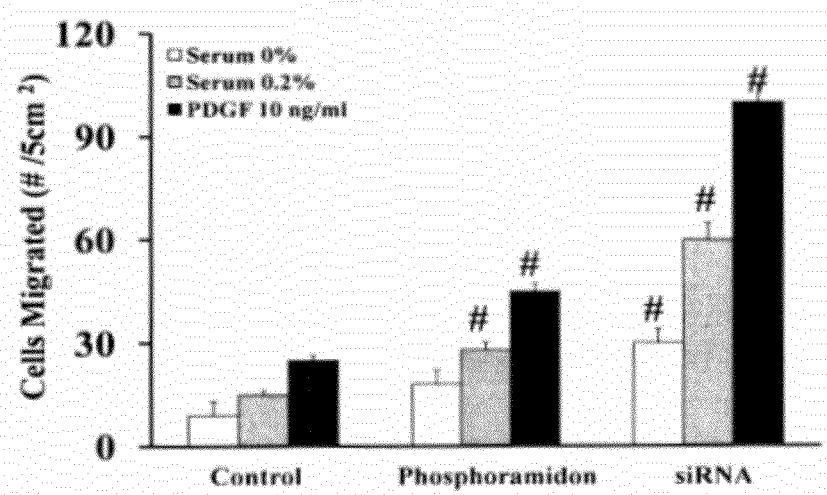

NEP null mice develop exaggerated hypoxia-induced pulmonary vascular remodeling (Dempsey et al., 2009). Migration and proliferation of PASMCs are important mechanisms contributing to pulmonary vascular remodeling (Hassoun et al., 2009). Therefore, the inventor compared these responses in PASMCs isolated from C57BL/6 NEP+/+ and NEP-/- mice. He found that PASMCs from NEP-/- mice exhibited increased migration in the presence of serum (0.2%) and PDGF-BB (10 ng/mL) compared to wild-type cells assessed by wound healing and Boyden chamber assays (FIGS. 9A-C). Proliferation was measured by $^3$H-thymidine incorporation at three different doses of serum and PDGF and showed 3- to 4-fold higher incorporation in NEP-/- PASMC compared to NEP+/+ cells (FIGS. 9D-E). The PDGF response was significantly higher than that observed with several known neuropeptide substrates of NEP (adrenomedulin, angiotensin II, bombesin, endothelin, neuromedin B) (data not shown) (Dempsey et al., 2009). The inventor initially tested PASMCs isolated from 15 different matched pairs of NEP+/+ and NEP-/- mice. Twelve pairs showed a major difference in proliferation; these cell lines were used for further study. Enhanced SMC outgrowth was also observed from NEP-/- PA tissue cultured ex vivo compared to control NEP+/+PA tissue (data not shown), suggesting that the differences observed in phenotype were intrinsic to the PASMC and not acquired over time in culture.

Lentiviral Expression of Full Length NEP Reduces Enhanced Migration and Proliferation of NEP-/- PASMC.

To determine whether replacing NEP in null cells would attenuate the enhanced responses observed, the inventor infected NEP-/- PASMC with lentiviral vector expressing full length human NEP at an MOI of 10 and migration and proliferation were measured after 48 hr. As seen in FIGS. 10A-C, lentiviral expression of NEP in -/- cells inhibited migration and proliferation in the presence of serum and PDGF. The inventor observed a greater inhibitory effect of NEP expression on migration than on proliferation of SMC (FIGS. 10B-C).

Inhibition of NEP Activity or Knock Down with siRNA Increases Migration and Proliferation in NEP+/+ PASMCs.

To test if increased migration and proliferation was directly due to loss of NEP and not an adaptive response, the inventor treated NEP+/+ cells with either the NEP inhibitor, phosphoramidon, or siRNA to mouse NEP for 48 h and measured migration and proliferation. The concentration of phosphoramidon (10 µmole/liter) used completely inhibits NEP activity in wild-type cells (Dempsey et al., 2009). There was a 98% loss of NEP expression after treatment with siRNA (FIG. 12C). Inhibition of NEP by phosphoramidon or knock down with siRNA in wild-type PASMCs caused increased migration and proliferation in response to serum and PDGF similar to that observed in NEP-/- cells (FIGS. 11A-E). In the case of siRNA treatment, the 0.2% serum induced increase in DNA synthesis did not achieve statistical significance.

NEP is Required for SM-Gene Expression.

The finding of increased migration and proliferation by NEP-/- PASMCs suggested that loss of NEP may induce a more synthetic phenotype. Phenotypic switching of SMC is accompanied by downregulation of SM-contractile proteins (Owens, 2007). The inventor measured levels of contractile proteins (α-SM-actin, SM-myosin, SM-22, and calponin) in NEP+/+ and NEP-/- SMCs. NEP-/- PASMCs expressed lower levels of SM-contractile proteins which was also observed at the mRNA level (FIGS. 12A-B). To determine whether NEP was directly regulating SM-gene expression, the inventor treated NEP+/+ cells with the NEP inhibitor, phosphoramidon, or with NEP specific siRNA to knockdown NEP and examined the effects on levels of SM-contractile proteins. Treatment with phosphoramidon or with NEP siRNA caused a decrease in expression of SM-contractile proteins in NEP+/+ cells (FIG. 12C). In addition, lentiviral expression of NEP or rNEP in null PASMCs restored levels of SM-markers, in particular α-SM-actin, SM-22 and calponin, suggesting a direct role for NEP in SMC function (FIG. 12D). Graphical representation of expression levels measured in 6 paired isolates is shown in FIG. 12E.

Loss of NEP Increases PDGFR Expression and Activation in PASMCs.

Figure 13D:
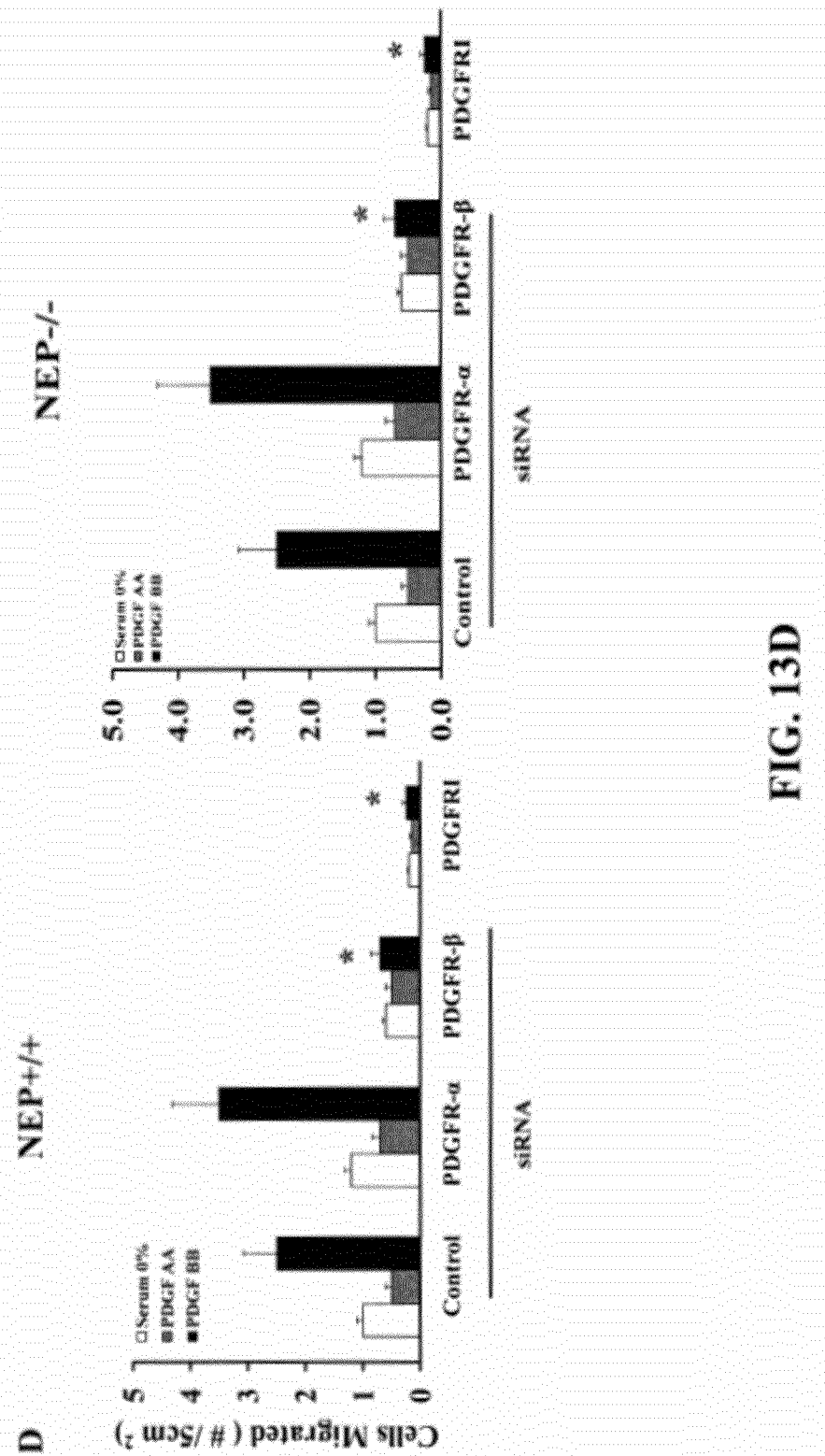
Figure 13E:
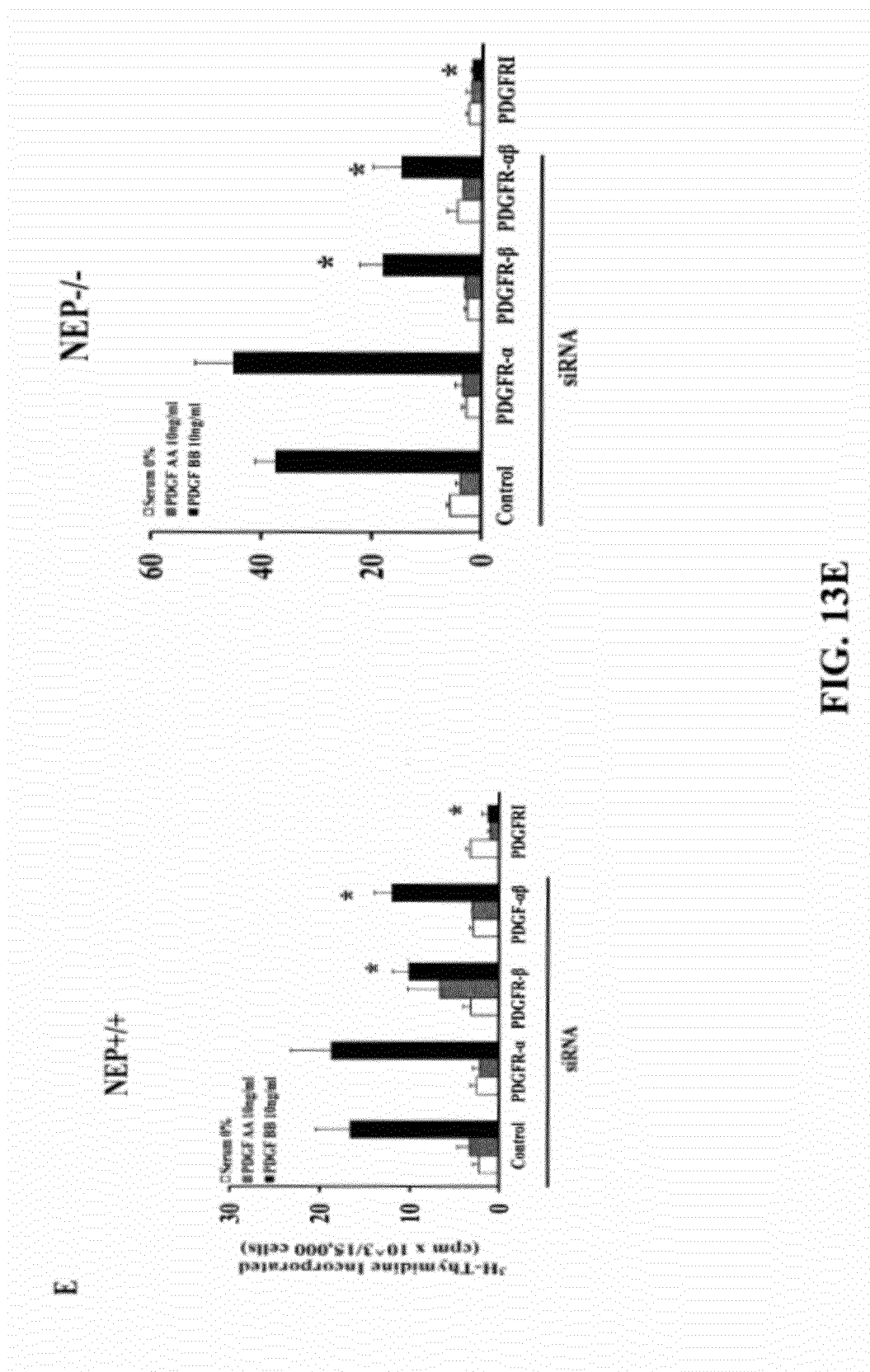
Figure 17:
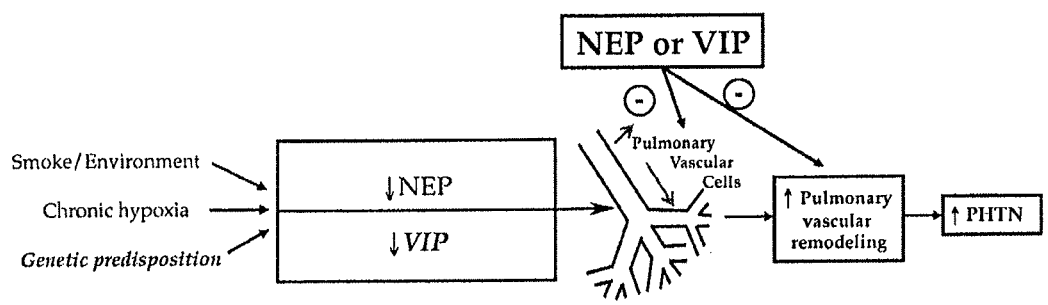
FIG. 17. Decreased NEP and VIP predispose to the development of increased pulmonary vascular remodeling. Chronic cigarette smoke, hypoxia, and genetic variation can cause a reduction in NEP activity and expression, leading to vascular dysfunction and remodeling. Decreases in, or the absence of, NEP predispose to exaggerated remodeling, not spontaneously, but in response to injury. Genetic variation can also cause a reduction in VIP, predisposing to spontaneous pulmonary vascular remodeling and PHTN. Whether reductions in VIP also increase remodeling in response to common injurious stimuli is not known.

To determine whether the migratory and proliferative responses were due to an increase in PDGFR receptor expression, the inventor measured PDGFR-α and PDGFR-β protein and mRNA levels by Western blot and semi quantitative RT-PCR respectively. As shown in FIG. 13A, protein levels of PDGFRα and PDGFR β were higher in NEP-/-.cells (1.3- and 1.9-fold, respectively). In contrast, mRNA levels for both PDGFR-α (0.67-fold) and PDGFR-β (0.56-fold) were lower in NEP-/- cells (FIG. 13B). To determine whether loss of NEP causes hyperactivation of PDGFR, the inventor measured levels of phospho$^{Y751}$ and total PDGFR β in NEP+/+ and NEP-/- cells by Western blotting. In addition since Src and PTEN are known to regulate PDGFR signaling by phosphorylation dependent mechanisms (Lu et al., 2003), the inventor also measured levels of phospho and total Src and PTEN by Western blotting using phospho-specific antibodies. Phosphorylation of Src$^{Y416}$ increases its activity and phosphorylation of PTEN$^{ser380}$ decreases its activity. As shown in FIG. 13C, the inventor found increased levels of PDGFR$^{Y715}$, p-Src$^{y416}$ and p-PTEN$^{ser380}$ in NEP-/- PASMCs. Total PTEN levels were lower (0.6-fold) in NEP-/- compared to +/+ cells but did not reach statistical significance. Association of Src with PDGFR has been shown to increase phosphorylation of PDGFR$^{Y751}$ (Kypta et al., 1990; Bromann et al., 2004). The inventor detected increased association of active Src kinase with PDGFR in null PASMCs in co-immunoprecipitation experiments (data not shown). SiRNA mediated knock down of NEP in wild-type PASMCs caused an increase in PDGFR signaling similar to that seen in null cells (FIG. 13D). Conversely, lentiviral expression of NEP in null SMCs attenuates PDGFR, Src and PTEN phosphorylation (FIG. 13D). Graphical representation of expression levels is shown in FIG. 13E. Loss of NEP significantly increased phosphorylation states of PDGFR, Src and PTEN resulting in a rise in Src kinase and decrease in PTEN activity in PASMC.

[Next Sections Use Ref Set B]

Background on NEP and VIP.

NEP (Genbank Accession # NC_000069) is a single transmembrane $Zn^{2+}$ metallopeptidase found in the lung, brush-border membrane of renal tubules, intestine, adrenal gland, brain, heart and peripheral blood vessels (Sumitomo et al., 2005). Its gene is located on mouse (and human) chromosome 3. The NEP protein has 750 amino acids: most of the protein is extracellular and contains the active site of the enzyme; the final N-terminal 25-28 amino acids are cytoplasmic (Sumitomo et al., 2005). The enzymatic action of NEP is to cleave peptides on the amino terminal side of hydrophobic amino acids, but NEP also has been shown to engage in intracellular signaling by novel peptidase-independent mechanisms that involve complex formation with other intracellular proteins and signaling intermediates (FIG. 14A) (Scholzen et al., 2001). The contributions of these non-enzymatic mechanisms of NEP to the regulation of pulmonary artery (PA) pressure are presently unknown, but may be quite significant.

NEP activity/expression is down-regulated in response to cigarette smoke and hypoxia (Grasemann et al., 1999; Sturiale et al., 1999; Lu et al., 1996; Marr and Spencer, 2010), and in diseases like lung and prostate cancer and Alzheimer's disease (Kirkwood et al., 2001; Shipp et al., 1990; Lu et al., 1997). The inventors speculate that individuals could vary in their susceptibility to chronic smoke- and hypoxia-induced PHTN depending on NEP activity/expression levels.

VIP, a 28 amino acid peptide with a molecular weight of 3.33 kD, was isolated in 1970 (Jandeleit-Dahm et al., 2005). The VIP gene is located on mouse chromosome 10 (human chromosome 6; Genbank Accession # NC_000076). Its translation product, a 170 amino acid precursor of VIP, is further processed to yield VIP and peptide histidine isoleucine (PHI) in mice, or peptide histidine methionine (PHM) in humans. PHI and PHM share many of VIP's actions, but are much less potent than VIP. VIP is widely, but selectively, distributed; its source is largely neuronal bodies that innervate tissues, including vascular and nonvascular smooth muscle (SM), cardiac muscle, and skeletal muscle. In the lungs, VIP has been localized within airway columnar epithelial cells, and within the medial SM layer and the junction of the medial and adventitial layers of blood vessels (Becker et al., 2010; Day et al., 2005; Dempsey et al., 2009).

VIP has two receptors sharing 50% identity, both belonging to the class II seven transmembrane spanning G protein-coupled receptor family (FIG. 14B). VPAC1 receptors are distributed within the CNS, liver, heart, lung, intestines, and blood vessels. VPAC2 receptors have also been reported within areas of the CNS, heart, and lung, but are also found in kidney, pancreas, and skeletal muscle (Becker et al., 2010; Dempsey et al., 2009; Owens, 2007). These receptors couple to stimulatory G proteins and increase adenylate cyclase activity, resulting in an increase of intracellular cAMP concentrations, but the full mechanism of action of VIP is not well-understood. In some cases, the VPAC1 and VPAC2 receptors may couple to inhibitory G proteins, stimulating guanylate cyclase activity (Holycross et al., 1992).

VIP is known to cause vasodilation, mediated through both/either endothelium-dependent (involving nitric oxide [NO]) and endothelium-independent mechanisms (which increase cAMP, and perhaps cGMP; FIG. 14B) (Turner, 2003; Becker et al., 2010; Barst, 2005). VIP also has important anti-inflammatory properties (Iwata et al., 2001). Anti-inflammatory, together with vasodilatory, effects and VIP's observed ability to inhibit the in vitro proliferation of human PA SMCs, may contribute to its anti-PHTN properties (Turner, 2003; Iwata et al., 2001; Garrington et a., 2000; Cuevas et al., 2003; Chen et al., 2006; Hassoun et al., 2009).

There is not much evidence that endogenous NEP and VIP interact in the lung under normal circumstances. NEP may be able to degrade VIP if the concentrations of VIP are high, as when it is applied exogenously (Sumitomo et al., 2004; Lu et al., 2003). However, the importance of NEP hydrolysis of endogenous VIP is equivocal in the lung (Lu et al., 2003; Kyupta et al., 1990). Conversely, it was reported that exogenous VIP did not affect NEP enzymatic activity (Bromann et al., 2004).

Background on Development and Initial Characterization of NEP and VIP KO Mice.

NEP null mice were first constructed in 1995 on a C57BL6 genetic background (Fitzpatrick et al., 2009), by disrupting exon 13 and a partial intron fragment of the gene with a neomycin resistance cassette (FIG. 15A). Although some gene-trapped mice with insertional mutations have also been created [International Knockout Mouse Consortium], they are not well-characterized and will not be discussed here. NEP KO mice were originally studied in a model of septic shock (Fitzpatrick et al., 2009); subsequent studies suggested an important role for NEP in the regulation of systemic blood pressure, permeability and inflammatory responses (Sirvent wet al., 2008). NEP KO mice were also used to characterize NEP's role in decreasing acute hypoxic ventilatory drive at sea level (Eddahibi et al., 2000). Finally, NEP KO mice were used in studies to characterize NEP's role in decreasing cutaneous inflammatory response to allergens (Perros et al., 2008) and in decreasing amyloid beta protein accumulation, which may contribute to the development of Alzheimer's disease (Chhina et al., 2008).

VIP null mice were constructed in 2003, also on a C57BL6 genetic background (Horiguchi et al., 2008). The targeting construct disrupts the VIP and PHI-encoding regions of the VIP precursor gene. To our knowledge, the construction of other VIP KO mice has not been reported. Colwell et al. and others (Horiguchi et al., 2008; Nisbet et al., 2010) have used these mice to characterize the circadian rhythm-regulatory mechanisms and effects of VIP and PHI. These mice have also been used to characterize many other effects of VIP, including effects on learning and behavior (Hansmann et al., 2008), GI morphology and function (Guignabert et al., 2009), regulation of male sex hormones (Ganju et al., 1996), inflammation (Garrington et al., 2000; Cuevas et al., 2003; Chen et al., 2006; Platek et al., 2007), and asthma (Platek et al., 2007).

Defining the Pulmonary Vascular Phenotype of the NEP and VIP KO Mice.

The inventor obtained C57BL6 NEP KO mice (Fitzpatrick et al., 2009) and characterized their pulmonary vascular phenotype (Grasemann et al., 1999). Normoxic C57BL6 NEP KO mice appear normal in most regards. Their body weights and lung structures (airway and alveolar structure, blood vessel density, and main PA diameter) do not differ from those of normoxic C57BL6 wt mice; however, there is a subtle trend towards decreased thicknesses of the adventitial/medial walls of the 50-125 µm pulmonary arteries at baseline. The hearts of normoxic C57BL6 NEP KO mice function normally with regard to the cardiac index, but they exhibit trends towards decreased cardiac (especially right ventricular, RV) mass vs normoxic C57BL6 wt mice. Interestingly, normoxic C57BL6 NEP KO mice have an increased number of lung neuroendocrine cells vs normoxic C57BL6 wt mice. However, we did not detect increases in lung levels of the peptidases ACE, ECE, APN, and DPPIV in compensation for NEP gene deletion (Grasemann et al., 1999).

In contrast, following 5 wks of hypoxia (18000 ft., hypobaric chamber), adult NEP KO mice exhibit increased right ventricular systolic pressure (RVSP: an indirect index of PA pressure), increased RV weight, and exaggerated pulmonary vascular remodeling (an important contributor to PHTN, apparent as thickened blood vessel walls). Morphometric analyses and quantitation showed that the pulmonary vessels of chronically hypoxic NEP KO (−/−) mice were more muscularized compared to those of hypoxic wt controls, as evidenced by a marked increase in the number of small (10-50 µm) α-SM actin positive vessels (FIG. 15B) with no change in overall vessel density. Vascular remodeling of the 50-125 µm pulmonary arteries of hypoxic NEP KO mice involves primarily a thickening of the medial layer, but, as shown in FIG. 15C, the adventitial layer of these pulmonary vessels is also thickened. FIGS. 15D-E provide a histological demonstration of these vascular changes. The adventitial layer thickening is an important finding, as it is rare that a mouse model of PHTN exhibits adventitial remodeling, an observation made in human PHTN. This may indicate that NEP KO mice may be able to model human PHTN quite well. Further morphometric analysis suggested there was local recruitment of α-SM actin positive/SM-specific myosin negative cells into the distal pulmonary vasculature in the NEP KO mice following exposure to chronic hypoxia, and that migration of de-differentiated SMC or myofibroblasts into the distal circulation may be a feature of this exaggerated remodeling (Grasemann et al., 1999).

Isolated PA SMCs from normoxic C57BL6 NEP KO (−/−) mice grow at a faster rate in response to serum or select neuropeptides than do PA SMCs from normoxic wt mice (NEP+/+ mice; FIG. 15F). Addition of recombinant NEP (rNEP) to the cell culture media (FIG. 15G) or lentiviral transduction with NEP cDNA (not shown here) result in a dose-dependent inhibition of proliferation of the NEP KO PA SMCs (Grasemann et al., 1999). This suggests that NEP may be protective against PHTN, in part, by attenuating the growth of SMCs.

In 2006 and 2007, Said et al. (Garrington et al., 2000; Hassoun et al., 2009) initially reported that C57BL6 VIP KO mice (FIG. 16A) (Horiguchi et al., 2008) spontaneously develop moderately severe PHTN. They noted, however, that female VIP KO mice did not exhibit PHTN as robustly as male VIP KO mice did (reason unknown); therefore, further experiments were completed mostly with male mice. PHTN in male VIP KO vs wt mice was evidenced by significant increases in RVSP, RV hypertrophy, and pulmonary vascular remodeling of both the proximal and distal PAs. As shown in FIGS. 16B-C, the 45-50 μm PAs of adult male VIP KO mice displayed increased medial thickness. Pulmonary vascular remodeling in VIP KO mouse lung is histologically demonstrated in FIG. 16D versus 16E. VIP KO mice displayed primarily an increase in the medial or SM layer of the arterial wall with little or no intimal or endothelial cell layer thickening. In addition, the VIP KO mice had extensive infiltrates of mononuclear inflammatory cells surrounding these thickened vessels, indicating that these lungs were inflamed. It was suggested that VIP may normally suppress immune function by inhibiting calcineurin-nuclear factor of activated T cell (NFAT) transcription factor pathways, which act as master switches of many immunological functions (Iwata et al., 2001).

Example 3

Discussion

The current study demonstrates that NEP is likely an important factor in the regulation of susceptibility of humans to pulmonary vascular remodeling in response to smoke inhalation and hypoxia. The inventor previously demonstrated that loss of NEP increases susceptibility to pulmonary vascular remodeling and PHTN in chronically hypoxic mice (Dempsey et al., 2009). The present work was undertaken because of the importance of extending findings made in animal models to human tissue. In COPD, pulmonary vascular remodeling requires several factors, including cigarette smoke, oxidant stress, inflammation, and intermittent or persistent hypoxia. Hypoxia may play a particularly important role in the PHTN of at least a portion of COPD patients (Thabut et al., 2005). A number of additional factors and pathways, including Il-6 and 5-HTT (also 5-HT itself) and bone morphogenic protein (BMP) may contribute to COPD-associated PHTN and variable susceptibility to PHTN in COPD (Steiner, 2009; Kubo et al., 2000; Chaouat et al., 2009; Ulrich et al., 2010; Morrell, 2010). This work suggests that NEP may also contribute to variable susceptibility to COPD-associated PHTN. Likewise, there is a wide range of expression levels of NEP in human lung (Cohen et al., 1996). Furthermore, the immunostaining results suggest that NEP protein expression in COPD lung, and also in lungs of humans with other causes of PHTN, is decreased more in the distal vasculature, where prominent remodeling is observed. This may be taken as additional evidence of the importance of NEP in pulmonary vascular disease. Whereas NEP expression in alveolar walls of COPD lung is low, this does not conflict with the inventor's finding that NEP expression is even lower in the distal pulmonary vasculature of COPD lung. NEP expressed on alveolar wall cells regulates the local neuropeptide balance and microenvironment and thus impacts nearby vascular cells.

NEP is involved in several signaling pathways, both by peptidase-dependent and -independent mechanisms (Sumitomo et al., 2005; Papandreou and Nanus, 2010); it is not clear which of these pathways may influence PA SMC biology. The inventor postulates that the loss of NEP activity/expression leads to the proliferation/migration of de-differentiated SMCs or myofibroblasts into the distal circulation, promoting pulmonary vascular remodeling and PHTN. However, besides proliferative and migratory effects, the loss of NEP may lead to vasoconstrictive, angiogenic, and inflammatory effects on many cell types, particularly on the PA SMCs of the distal pulmonary vasculature. The inventor's laboratory has found (Dempsey et al., 2009; Karoor et al., 2010) that serum, select neuropeptides, and growth factors like PDGF have proliferative and migratory effects on mouse PA SMCs, which are inversely dependent on NEP (i.e., these effects are increased or decreased when NEP is decreased or increased, respectively). NEP null PA SMCs also have increased proliferative responses to hypoxia in the presence of trace serum and neuropeptides (Dempsey et al., 2009). However, the magnitude of the responses to hypoxia, CSE, or $H_2O_2$ are quite small compared to those of major peptide mitogens, like PDGF alone (not shown). Recently, the inventor obtained evidence that one mechanism whereby NEP inhibits the proliferation and migration of wt mouse PA SMCs is through inhibition of the association of Src-Kinase and the PDGF receptor (Karoor et al., 2010).

The NEP substrates endothelin-1 (Lee and Channick, 2005) and the bombesin-like peptides (BLPs) (Jensen et al., 2008) have proliferative and vasoconstrictive properties; Basic fibroblast growth factor-2 (FGF-2; 155 amino acids) has potent angiogenic effects (Papandreou and Nanus, 2010). Decreases in NEP would be expected to increase the effects of these NEP substrates. The anti-inflammatory effects of NEP (Lu et al., 1997) are important also, as it is thought that inflammation contributes to pulmonary vascular remodeling in COPD (Weitzenblum et al., 2009). Pro-inflammatory peptide substrates such as substance P and bradykinin are degraded by NEP. NEP has also been found to reduce local concentrations of select pro-inflammatory mediators, likely through peptidase-independent interactions with other signaling molecules (Lu et al., 1996).

NEP may be involved in pathways with other mediators that have been proposed to play roles in PHTN or COPD-associated PHTN, such as 5-HT (or 5-HTT). NEP gene deletion is associated with increased numbers of pulmonary neuroendocrine cells [NECs; (Dempsey et al., 2009)], which secrete, among other neuropeptides and amines, the pulmonary vasoconstrictor 5-HT (Gosney, 1997). Since patients with COPD may have up to 2-fold increases in the number of pulmonary NECs compared to normal smokers (Aguayo, 1994), NEP may be negatively correlated with pulmonary hypertensive levels of 5-HT. The inventor plans to investigate interactions between NEP and other possible mediators of COPD-associated PHTN, such as 5-HT (or 5-HTT), 11-6, or BMP, in future studies. The inventor believes that the above facts and findings strongly suggest an inverse functional link between NEP and pulmonary: vascular remodeling.

All of the present advanced COPD lung samples showed evidence of pulmonary vascular remodeling (including a 'dropout' of the distal vessels and vascular wall thickening). Although the inventor cannot obtain direct PA pressure data on the majority of these patients, the vascular remodeling data is sufficient to indicate the likely presence of PHTN either at rest or with exercise. The inventor found in his advanced COPD samples, a dropout, or decreased density of the small (25-100 μm) pulmonary vessels (FIG. 1A). Matsuoka et al. (2010) recently demonstrated that, among severe COPD patients, there is a significant correlation of rarification or 'dropout' of the small, distal pulmonary vessels with PA pressure, measured at rest. This relationship indicates that many of the COPD patients may have had rest PHTN. Secondly, as Kubo et al. (2000) have shown, pulmonary vascular wall thickness in advanced COPD patients is significantly related to exercise-induced PHTN. The inventor concludes that a large proportion of the advanced COPD patients had rest PHTN, but in addition, most, if not all, of the inventor's patients would have had PHTN induced by exercise.

CS-induced damage to endothelial cells is considered to be the primary alteration that initiates PHTN in COPD (Peinado et al., 2008). Chronic CS exposure causes a thickening of the endothelial (intimal) layer of the pulmonary vessels, where SMC-like cells have been found. Although these intimal changes contribute to the remodeling found with COPD, medial and adventitial changes become more prominent in advanced disease (Santos et al., 2002) as the inventor has found in his advanced COPD patients. It is unknown what causes the progression from CS injury to PHTN associated with COPD. The inventor proposes that a decrease in lung NEP activity/expression may be one of these factors.

In lung tissue, the inventor found a differential effect, i.e., NEP activity in COPD (versus 'Control') lungs was decreased by 76%, whereas NEP protein expression in COPD lungs was only decreased by 48%. This differential effect may at least in part involve ROS-inactivation of the NEP enzyme through chemical adduct formation, while still allowing antibody detection of the NEP protein (Shinall et al., 2005; Wang et al., 2003). ROS present in COPD lungs may come directly from cigarette smoke products, or may be generated in COPD lungs due to inflammatory responses, or localized hypoxia (Bowers et al., 2004; Park et al., 2009; Church and Pryor, 1985). The inventor found that COPD lung tissue has much higher levels of nitrotyrosine and 8-HG residues when compared to 'Controls' (indicating greater oxidative stress in the COPD samples), that NEP activity is directly inactivated by $H_2O_2$ (which models the response of NEP to a number of oxidants in general), and that an antioxidant (Tiron) prevents loss of NEP activity due to CSE or hypoxia (or to $H_2O_2$), further strengthening this connection between reduced NEP activity and ROS in COPD. Although Tiron acts as an SOD mimetic, it also is able to chelate certain metal ions, and has been shown to react with ('scavenge') hydroxyl radicals (which are likely the major reactive species through which $H_2O_2$ acts) at 100 times the rate that it reacts with superoxide radicals; Tiron has been characterized as an 'electron trap' (Taiwo, 2008). A preliminary experiment with other antioxidants with catalase-like activity suggests that, like these other antioxidants, in these experimental systems, Tiron is able to combat oxidation by $H_2O_2$.

The inventor also found differential decreases of NEP protein and mRNA levels (48% and 30% decreases in 'Control' vs COPD, respectively), which may involve inductions of lysosomal and/or proteasomal NEP protein degradation in COPD lung. Because NEP is associated with the cell membrane, the inventor presumed that a substantial amount of NEP protein may be degraded in the lysosome; however, proteasomal mechanisms could not be ruled out. The inventor found evidence that both types of mechanisms may be of importance in mediating NEP protein degradation in PA SMCs. However, Malhotra et al. have found that proteasomal expression is decreased in humans with severe COPD (Malhotra et al., 2009). This may mean that lysosomal, rather than proteasomal, NEP protein degradation is more important in humans with COPD.

The inventor has not investigated mechanisms resulting in decreases in NEP mRNA. In COPD, there may be important changes in the concentrations of or interactions of NEP with various transcription factors, or of NEP gene methylation. These mechanisms will be addressed in future work.

It is acknowledged that the current studies have limitations, but these issues in any way compromise the conclusions set forth herein. Human lung samples are difficult to obtain, as they are often collected during major invasive procedures. If they are obtained from tissue donors, they may be accompanied with concerns about ischemic time during the harvest. Lung tissue may be subject to a 'satellite' effect from adjacent tumors or granulomas. Unintentional variations in harvest and preparation of the samples make morphometric analyses more technically difficult but these variables did not impact the activity and expression measurements. Morphometric analyses were also complicated by the heterogeneity observed in COPD lung sections, i.e., localized areas of advanced disease often co-exist within or near areas of relatively normal-looking tissue. This in vitro cell system, human PA SMCs exposed to CSE, hypoxia, and $H_2O_2$, obviously represents an over-simplification, which did not model differential effects on NEP activity and expression observed in vivo. However, most COPD patients are subject to varying conditions for years, whereas the treatments of the PA SMCs are short-term, and they can be expected to only partially model some of the conditions, cell-types, and tissue destructive factors present in COPD lungs. Proximal PA SMCs from humans were used as the best available model of distal PA SMCs (Dempsey et al., 1991), because it would have been very difficult, if not impossible, to obtain sufficient numbers of distal human PA SMCs for the current study. However, the pattern of SMC responses was consistent with observations made with lung tissue. The inventor has found that CS (not shown), like hypoxia (Dempsey et al., 2009), decreases NEP activity and expression in wild-type mouse lung. No adaptive changes in other relevant lung peptidases, including DPPIV, Endothelin converting enzyme (ECE), and Angiotensin converting enzyme (ACE), were found in mouse lung when NEP levels were reduced (Dempsey et al., 2009). In human lung, the inventor has also observed by immunohistochemistry that CS inhibits NEP protein expression (not shown), but the present results indicate that CS may not affect NEP mRNA much. The decreases observed here in humans in NEP activity/expression are not due to general cell loss, and may also be selective for NEP. The inventor compared decreases observed for NEP in human lung to another peptidase, DPPIV, which in many respects may be similar to NEP, but has important differences (Lambeir et al., 2001; Mentlein, 1999; Jung et al., 2006). Both NEP and DPPIV are found within the lung, as well as within many other tissues, are cell surface type II membrane peptidases, and have similar structures, despite the fact that DPPIV is a serine aminopeptidase, whereas NEP is a zinc endopeptidase. Both peptidases are involved in the degradation of substance P, bradykinin, neuropeptide Y, and to a varying extent, VIP (Mentlein, 2004; van der Velden and Hulsmann, 1999; Gourlet et al., 1997; Lambeir et al., 2001; Mentlein, 1999), but both enzymes have other substrates that are unique to each. In addition, DPPIV is much more actively involved in the degradation of VIP than is NEP. NEP can hydrolyze VIP when it reaches high concentrations, resulting in the generation of several peptides which are still active (Gourlet et al., 1997). Also, in contrast to NEP, DPPIV inhibition tends to promote lung function (Jung et al., 2006). DPPIV activity/protein expression did not vary between 'Control' and COPD lungs. The studies presented here do not exclude the possibility that other lung peptidases, like ACE-2 (Ferreira et al., 2009, may also contribute to the pathogenesis of PHTN in chronic diseases like COPD. In future work, the inventor plans a wider analysis of these and other peptidases in control and diseased tissue.

Because of the high incidence of COPD and the increased availability of characterized lung tissue, COPD is a useful human model for the study of mechanisms of pulmonary vascular disease induced by smoke inhalation and hypoxia. There is much individual variation in the severity of COPD-associated PHTN, and also in the normal range of NEP pulmonary activity/expression. Based on these results, the inventor hypothesizes that individuals may vary in their susceptibility to pulmonary vascular remodeling and PHTN depending on their level of lung NEP activity/expression. These studies could lead to new treatments based on the concept that maintaining or increasing lung NEP may protect against PHTN in response to chronic smoke and hypoxia.

[Ref Set B Below]

Currently, treatment options for PHTN are inadequate, making therapies suggested by work with the NEP and VIP KO mice important. We hypothesize that maintaining or increasing lung NEP levels may protect against smoke and hypoxia-induced secondary PHTN. We have shown, with mouse NEP KO PA SMCs, that replacement of NEP decreases their enhanced growth (FIG. 15G and (Dempsey et al., 2009)). In order to test the efficacy of NEP to prevent or reverse pulmonary vascular remodeling and PHTN in vivo, we have constructed transgenic mice that overexpress NEP in a conditional manner. We also have plans to test if NEP replacement can prevent or treat PHTN in murine models of smoke- and hypoxia-induced PHTN.

VIP replacement has been tested in VIP KO mice and a few humans with IPAH. In mice, IP injections of VIP, given every other day, reduced RV hypertrophy and PA medial thickening (Said et al., 2007). In human IPAH patients, VIP inhalation therapy (in which subjects reported no untoward effects) resulted in significant improvement of PaO$_2$ and exercise capacity, parameters that suggest that PHTN was also reduced. Also, VIP inhibited the in vitro proliferation of human PA SMCs from IPAH patients (Petkov et al., 2003). These observations suggest that further studies on the use of VIP as a treatment for PHTN are warranted (Lykouras et al., 2008; Petkov et al., 2003; Said et al., 2010; Said et al., 2007).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference:

U.S. Pat. No. 4,196,265
U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,873,191
U.S. Pat. No. 4,879,236
U.S. Pat. No. 4,883,750
U.S. Pat. No. 4,952,500
U.S. Pat. No. 5,217,879
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
EPO 0273085

EPO 329 822
GB Appn. 2 202 328
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 9217598
PCT Appln. WO 94/09699
PCT Appln. WO 95/06128
Abraham, *Genes Dev.,* 15:2177-2196, 2001.
Aguayo, *Am. J. Respir. Crit. Care Med.,* 149:1692-1698, 1994.
Aldridge et al., *J. Neurosci. Methods,* 172:250-254, 2008.
Almendro et al., *J. Immunol.,* 157(12):5411-5421, 1996.
Amado and Chen, *Science,* 285(5428):674-676, 1999.
Angel et al., *Cell,* 49:729, 1987b.
Angel et al., *Mol. Cell. Biol.,* 7:2256, 1987a.
Armentano et al., *Proc. Natl. Acad. Sci. USA,* 87(16):6141-6145, 1990.
Atchison and Perry, *Cell,* 46:253, 1986.
Atchison and Perry, *Cell,* 48:121, 1987.
Ausubel et al., In: *Current Protocols in Molecular Biology,* John, Wiley & Sons, Inc, New York, 1994.
Banerji et al., *Cell,* 27(2 Pt 1):299-308, 1981.
Banerji et al., *Cell,* 33(3):729-740, 1983.
Barany and Merrifield, In: *The Peptides,* Gross and Meienhofer (Eds.), Academic Press, NY, 1-284, 1979.
Barst, *J. Clin. Invest.,* 115:2691-2694, 2005.
Bates, *Mol. Biotechnol.,* 2(2):135-145, 1994.
Batra et al., *Am. J. Respir. Cell Mol. Biol.,* 21(2):238-245, 1999.
Battraw and Hall, *Theor. App. Genet.,* 82(2):161-168, 1991.
Becker et al., *PLoS One,* 5, 2010.
Beckman et al., *J. Biol. Chem.,* 263:6884-6892, 1988.
Bellus, *J. Macromol. Sci. Pure Appl. Chem.,* A31(1): 1355-1376, 1994.
Berkhout et al., *Cell,* 59:273-282, 1989.
Bett et al., *J. Virololgy,* 67(10):5911-5921, 1993.
Bhattacharjee et al., *J. Plant Bioch. Biotech.,* 6(2):69-73. 1997.
Bilbao et al., *Transplant Proc.,* 31(1-2):792-793, 1999.
Blackwell et al., *Arch. Otolaryngol. Head. Neck Surg.,* 125 (8):856-863, 1999.
Blanar et al., *EMBO J.,* 8:1139, 1989.
Blomer et al., *J. Virol.,* 71(9):6641-6649, 1997.
Bodine and Ley, *EMBO J.,* 6:2997, 1987.
Boshart et al., *Cell,* 41:521, 1985.
Bosze et al., *EMBO J.,* 5(7):1615-1623, 1986.
Bowers et al., *Am. J. Respir. Crit. Care Med.,* 169:764-769, 2004.
Braddock et al., *Cell,* 58:269, 1989.
Brinster et al., *Proc. Natl. Acad. Sci. USA,* 82(13):4438-4442, 1985. Levine, *Cell,* 88:323-331, 1997.
Bromann et al., *Oncogene,* 23:7957-7968, 2004.
Bulla and Siddiqui, *J. Virol.,* 62:1437, 1986.
Campbell and Villarreal, *Mol. Cell. Biol.,* 8:1993, 1988.
Campbell et al., *Am. Rev. Respir. Dis.,* 130(3):417-423, 1984.
Campere and Tilghman, *Genes and Dev.,* 3:537, 1989.
Campo et al., *Nature,* 303:77, 1983.
Capaldi et al., *Biochem. Biophys. Res. Comm.,* 76:425, 1977.
Cape et al., *Pharmaceutical Research* 25:1967-1990, 2008.
Caplen et al., *Gene Ther.,* 6(3):454-459, 1999.
Carbonelli et al., "*FEMS Microbiol Lett.* 177(1):75-82, 1999.
Carpenter and Stenmark, *Am. J. Physiol. Lung Cell Mol. Physiol.,* 281:L941-948, 2001.
Case et al., *Proc. Natl. Acad. Sci. USA,* 96(6):2988-2893, 1999.
Celander and Haseltine, *J. Virology,* 61:269, 1987.
Celander et al., *J. Virology,* 62:1314, 1988.
Chandler et al., *Cell,* 33:489, 1983.
Chandler et al., *Proc. Natl. Acad. Sci. USA,* 94(8):3596-601, 1997.
Chang et al., *Mol. Cell. Biol.,* 9:2153, 1989.
Chaouat et al., *Chest,* 136:678-687, 2009.
Chatterjee et al., *Proc. Natl. Acad. Sci. USA,* 86:9114, 1989.
Chen and Okayama, *Mol. Cell. Biol.* 7:2745-2752, 1987.
Chen et al., *Carcinogenesis,* 27:903-915, 2006.
Chen et al., *Genes Dev.,* 10:2438-2451, 1996.
Chhina et al., *Expert Rev. Respir. Med.,* 2:419-431, 2008.
Chillon et al., *J. Virol.,* 73(3):2537-2540, 1999.
Cho et al., *Biotechniques,* 30:562-572, 2001.
Choi et al., *Cell,* 53:519, 1988.
Christou et al., *Proc. Natl. Acad. Sci. USA,* 84(12):3962-3966, 1987.
Church and Pryor, *Environ. Health Perspect.,* 64:111-126, 1985.
Churg et al., *Am. J. Physiol. Lung Cell Mol. Physiol.,* 294: L612-631, 2008.
Clay et al., *Pathol. Oncol. Res.,* 5(1):3-15, 1999.
Cocea, Biotechniques, 23(5):814-816, 1997.
Coffey et al., *Science,* 282(5392):1332-1334, 1999.
Cohen et al., *Cancer Res.,* 56:831-839, 1996.
Cohen et al., *J. Cell. Physiol.,* 5:75, 1987.
Colwell et al., *Am. J. Physiol. Regul. Integr. Comp. Physiol.,* 285(5):R939-949, 2003.
Cook et al., *Cell,* 27:487-496, 1981.
Cool et al., *Am. J. Respir. Crit. Care Med.,* 174:654-658, 2006.
Costa et al., *Mol. Cell. Biol.,* 8:81, 1988.
Cripe et al., *EMBO J.,* 6:3745, 1987.
Cuevas et al., *Embo. J.,* 22:3346-3355, 2003.
Culotta and Hamer, *Mol. Cell. Biol.,* 9:1376, 1989.
Culver et al., *Science,* 256(5063):1550-1552, 1992.
Dandolo et al., *J. Virology,* 47:55-64, 1983.
Day et al., *Arch. Biochem. Biophys.,* 347:256-262, 1997.
Day et al., *J. Surg. Res.,* 128:21-27, 2005.
De Villiers et al., *Nature,* 312(5991):242-246, 1984.
DeLuca et al., *J. Virol.,* 56(2):558-570, 1985.
Dempsey et al., *Am. J. Pathol.,* 174(3):782-796, 2009.
Dempsey et al., *Am. J. Physiol.,* 260:L136-145, 1991.
Dempsey et al., *J. Perinatol.,* 16:S2-11, 1996.
Deng et al., *Cell,* 82:675-684, 1995.
Derby et al., *Hear Res.,* 134(1-2):1-8, 1999.
Deschamps et al., *Science,* 230:1174-1177, 1985.
D'Halluin et al., *Plant Cell,* 4(12):1495-1505, 1992.
Dick et al., *J. Biol. Chem.,* 271:7273-7276, 1996.
Dorai et al., *Int. J. Cancer,* 82(6):846-852, 1999.
Dusser et al., *Clin. Invest.,* 84:900-906, 1989.
Edbrooke et al., *Mol. Cell. Biol.,* 9:1908, 1989.
Eddahibi et al., *Am. J. Respir. Crit. Care Med.,* 162:1493-1499, 2000.
Edlund et al., *Science,* 230:912-916, 1985.
El-Deiry, *Semin. Cancer Biol.* 8:345-357, 1998.
Engel and Kohn, *Front Biosci.,* 4:e26-33, 1999.
Falck et al., *Nature,* 434:605-611, 2005.
Fechheimer, et al., *Proc Natl. Acad. Sci. USA,* 84:8463-8467, 1987.
Feldman et al., *Semin. Interv. Cardiol.,* 1(3):203-208, 1996.
Feng and Holland, *Nature,* 334:6178, 1988.
Feng et al., *Nat. Biotechnol.,* 15(9):866-870, 1997.
Ferreira et al., *Am. J. Respir. Crit. Care Med.,* 179:1048-1054, 2009.

Firak and Subramanian, *Mol. Cell. Biol.*, 6:3667, 1986.
Fisher et al., *Virology*, 217(1):11-22, 1996.
Fitzpatrick et al., *Int. J. Biochem. Cell Biol.*, 41:2287-2294, 2009.
Foder et al., *Science*, 251:767-773, 1991.
Foecking and Hofstetter, *Gene*, 45(1):101-105, 1986.
Forster and Symons, *Cell*, 49:211-220, 1987.
Fraley et al., *Proc. Natl. Acad. Sci. USA*, 76:3348-3352, 1979.
Freifelder, In: *Physical Biochemistry Applications to Biochemistry and Molecular Biology*, 2nd Ed. Wm. Freeman and Co., NY, 1982.
Frohman, In: *PCR Protocols: A Guide To Methods And Applications*, Academic Press, N.Y., 1990.
Fujita et al., *Cell*, 49:357, 1987.
Fujiwara and Tanaka, *Nippon Geka Gakkai Zasshi*, 99(7): 463-468, 1998.
Ganju et al., *Blood*, 88:4159-4165, 1996.
Garat et al., *Mol. Cell Biol.*, 26:4934-4948, 2006.
Garoff and Li, *Curr. Opin. Biotechnol.*, 9(5):464-469, 1998.
Gamido et al., *J. Neurovirol.*, 5(3):280-288, 1999.
Garrington et al., *Embo. J*, 19:5387-5395, 2000
Gefter et al., *Somatic Cell Genet.*, 3:231-236, 1977.
Gerlach et al., *Nature (London)*, 328:802-805, 1987.
Ghosh and Bachhawat, In: *Liver Diseases, Targeted Diagnosis and Therapy Using Specific Receptors and Ligands*, Wu and Wu (Eds.), Marcel Dekker, New York, 87-104, 1991.
Gilles et al., *Cell*, 33:717, 1983.
Gloss et al., *EMBO J.*, 6:3735, 1987.
Gnant et al., *Cancer Res.*, 59(14):3396-403, 1999.
Gnant et al., *J. Natl. Cancer Inst.*, 91(20):1744-1750, 1999.
Godbout et al., *Mol. Cell. Biol.*, 8:1169, 1988.
Goding, In: *Monoclonal Antibodies: Principles and Practice*, 2d ed., Orlando, Fla., Academic Press, 60-61, 65-66, 71-74, 1986.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Gosney, *Microsc. Res. Tech.*, 37:107-113, 1997.
Gottifredi and Prives, *Semin. Cell Dev. Biol.*, 16:355-368, 2005.
Gourlet et al., *Biochem. Pharmacol.*, 54:509-515, 1997.
Graham and Prevec *Mol. Biotechnol.*, 3(3):207-220, 1995.
Graham and Van Der Eb, *Virology* 52:456-467, 1973
Grasemann et al., *J. Appl. Physiol.*, 87:1266-1271, 1999.
Greene et al., *Immunology Today*, 10:272, 1989
Grosschedl and Baltimore, *Cell*, 41:885, 1985.
Guignabert et al., *Am. J. Physiol. Lung Cell Mol. Physiol.*, 297:L1082-1090, 2009.
Hacia et al., *Nature Genet.*, 14:441-449, 1996.
Haecker et al., *Hum. Gene Ther.*, 7(15):1907-1914, 1996.
Hamidi et al., *Eur. Respir. J.*, 31(1):135-139, 2008.
Han et al., *Euro. J. Surgical Oncology*, 25:194-198, 1999.
Hansmann et al., *J. Clin. Invest.*, 118:1846-1857, 2008.
Harland and Weintraub, *J. Cell Biol.*, 101:1094-1099, 1985.
Harlow and Lane, In: *Antibodies: A laboratory Manual*, Cold Spring Harbor Laboratories, Cold Spring Harbor, N.Y., 1988.
Haslinger and Karin, *Proc. Natl. Acad. Sci. USA*, 82:8572, 1985.
Hassoun et al., *J. Am. Coll. Cardiol.*, 54:S10-19, 2009.
Hauber and Cullen, *J. Virology*, 62:673, 1988.
Hayashi et al., *Neurosci. Lett.*, 267(1):37-40, 1999.
He et al., *Plant Cell Reports*, 14 (2-3):192-196, 1994.
Hen et al., *Nature*, 321:249, 1986.
Hensel et al., *Lymphokine Res.*, 8:347, 1989.
Hermens and Verhaagen, *Prog. Neurobiol.*, 55(4):399-432, 1998.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Hogan et al., In: *Manipulating the Mouse Embryo: A Laboratory Manual*, 2nd ed., Cold Spring Harbor Laboratory Press, 1994.
Holbrook et al., *Virology*, 157:211, 1987.
Holycross et al., *Circ. Res.*, 71:1525-1532, 1992.
Holzer et al., *Virology*, 253(1):107-114, 1999.
Horiguchi et al., *Prostate Cancer Prostatic Dis.*, 11:79-87, 2008.
Horlick and Benfield, *Mol. Cell. Biol.*, 9:2396, 1989.
Hou and Lin, *Plant Physiology*, 111:166, 1996.
Howard et al., *Ann. NY Acad. Sci.*, 880:352-365, 1999.
Huang et al., *Cell*, 27:245, 1981.
Huard et al., *Neuromuscul Disord.*, 7(5):299-313, 1997.
Hug et al., *Mol. Cell. Biol.*, 8:3065, 1988.
Huss and Wieczorek, *J. Exp. Biol.*, 212:341-346, 2009.
Hwang et al., *Mol. Cell. Biol.*, 10:585, 1990.
Imagawa et al., *Cell*, 51:251, 1987.
Imai et al., *J. Virol.*, 72(5):4371-4378, 1998.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*, 85(24):9436-9440, 1988.
Irie et al., *Antisense Nucleic Acid Drug Dev.*, 9(4):341-349, 1999.
Iwata et al., *Science*, 292:1550-1552, 2001.
Jakobovits et al., *Mol. Cell. Biol.*, 8:2555, 1988.
Jameel and Siddiqui, *Mol. Cell. Biol.*, 6:710, 1986.
Jandeleit-Dahm et al., *J. Hypertens*, 23:2071-2082, 2005.
Jaynes et al., *Mol. Cell. Biol.*, 8:62, 1988.
Jeffery, *Am. J. Respir. Crit. Care Med.*, 164:S28-38, 2001.
Jensen et al., *Pharmacol. Rev.*, 60:1-42, 2008.
Johnson et al., IN: *Biotechnology And Pharmacy*, Pezzuto et al., (Eds.), Chapman and Hall, New York, 1993.
Johnson et al., *Mol. Cell. Biol.*, 9:3393, 1989.
Johnston et al., *J. Virol.*, 73(6):4991-5000, 1999.
Joyce, *Nature*, 338:217-244, 1989.
Jung et al., *J. Heart Lung Transplant.*, 25:1109-1116, 2006.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karin et al., *Mol. Cell. Biol.*, 7:606, 1987.
Karoor et al., *Am. J. Respir. Crit. Care Med.*, 181:A1171, 2010.
Katinka et al., *Cell*, 20:393, 1980.
Kato et al., *J. Biol. Chem.*, 266(6):3361-3364, 1991.
Kaufman et al., *Surv. Ophthalmol.*, 43Suppl 1:S91-97, 1999.
Kawamoto et al., *Mol. Cell. Biol.*, 8:267, 1988.
Kay, *Haemophilia*, 4(4):389-392, 1998.
Kiledjian et al., *Mol. Cell. Biol.*, 8:145, 1988.
Kim and Cech, *Proc. Natl. Acad. Sci. USA*, 84:8788-8792, 1987.
Kirkwood et al., *Am. J. Physiol. Gastrointest. Liver Physiol.*, 281:G544-551, 2001.
Klamut et al., *Mol. Cell. Biol.*, 10:193, 1990.
Klimatcheva et al., *Front Biosci.*, 4:D481-96, 1999.
Koch et al., *Mol. Cell. Biol.*, 9:303, 1989.
Kohler and Milstein, *Eur. J. Immunol.*, 6:511-519, 1976.
Kohler and Milstein, *Nature*, 256:495-497, 1975.
Kohut et al., *Am. J. Physiol.*, 275(6 Pt 1):L1089-94, 1998.
Kong et al., *Faseb.* 1, 20:2242-2250, 2006.
Kooby et al., *FASEB J.*, 13(11):1325-1334, 1999.

Kornberg, In: *DNA Replication*, W. H. Freeman and Company, New York, 1992.
Kraus et al., *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Krisky et al., *Gene Ther.*, 5(12):1593-1603, 1998.
Kubo et al., *Respir. Physiol.*, 120:71-79, 2000.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86(4):1173-1177, 1989.
Kypta et al., *Cell*, 62:481-492, 1990.
Kyte and Doolittle, *J. Mol. Biol.*, 157(1):105-132, 1982.
Lachmann and Efstathiou, *Clin. Sci. (Colch)*, 96(6):533-541, 1999.
Lambeir et al., *FEBS. Lett.*, 507:327-330, 2001.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lazzeri, *Methods Mol. Biol.*, 49:95-106, 1995.
Lee and Channick, *Semin. Respir. Crit. Care Med.*, 26:402-408, 2005.
Lee et al., *J. Auton. Nerv. Syst.*, 74(2-3):86-90, 1997.
Lee et al., *Korean J. Genet.*, 11(2):65-72, 1989.
Lee et al., *Nature*, 294:228, 1981.
Lee et al., *Nature*, 329(6140):642-645, 1987.
Lee et al., *Nucleic Acids Res.*, 12:4191-206, 1984.
Leibowitz et al., *Diabetes*, 48(4):745-753, 1999.
Leonhardt et al., *J. Cell Biol.*, 149:271-280, 2000.
Lesch, *Biol. Psychiatry*, 45(3):247-253, 1999.
Levenson et al., *Human Gene Therapy*, 9:1233-1236, 1998.
Levinson et al., *Nature*, 295:79, 1982.
Li et al., *Science*, 275:1943-1947, 1997.
Liang and Pardee, *Nature Reviews Cancer*, 3:869-876, 2003.
Liang, *Biotechniques*, 33:338-346, 2002.
Lin et al., *Mol. Cell. Biol.*, 10:850, 1990.
Littler et al., *Am. J. Physiol. Lung Cell Mol. Physiol.*, 289: L1083-1093, 2005.
Lu et al., *Ann. NY Acad. Sci.*, 780:156-163, 1996.
Lu et al., *J. Biol. Chem.*, 278:40057-40066, 2003.
Lu et al., *J. Exp. Med.*, 181(6):2271-2275, 1995.
Lu et al., *Nat. Med.*, 3:904-907, 1997.
Lundstrom, *J. Recept. Signal Transduct. Res.*, 19(1-4):673-686, 1999.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Lykouras et al., *Inflamm. Allergy Drug Targets*, 7 (4):260-269, 2008.
Macejak and Sarnow, *Nature*, 353:90-94, 1991.
Majors and Varmus, *Proc. Natl. Acad. Sci. USA*, 80:5866, 1983.
Malhotra et al., *Am. J. Respir. Crit. Care Med.*, 180:1196-1207, 2009.
Marienfeld et al., *Gene Ther.*, 6(6):1101-1113, 1999.
Marr and Spencer, *Curr. Alzheimer Res.*, 7:223-229, 2010.
Mastrangelo et al., *Cancer Gene Ther.*, 6(5):409-422 1999.
Matsuoka et al., *Am. J. Respir. Crit. Care Med.*, 181:218-225, 2010.
McNeall et al., *Gene*, 76:81, 1989.
Mentlein, *Int. Rev. Cytol.*, 235:165-213, 2004.
Mentlein, *Regul. Pept.*, 85:9-24, 1999.
Merrifield, *Science*, 232(4748):341-347 1986.
Michel and Westhof, *J. Mol. Biol.*, 216:585-610, 1990.
Miksicek et al., *Cell*, 46:203, 1986.
Miller et al., *Methods Enzymol.*, 217:581-599, 1993.
Miyatake et al., *Gene Ther.*, 6(4):564-572, 1999.
Moldawer et al., *Shock*, 12(2):83-101, 1999.
Mordacq and Linzer, *Genes and Dev.*, 3:760, 1989.
Moreau et al., *Nucl. Acids Res.*, 9:6047, 1981.
Moriuchi et al., *Cancer Res.*, 58(24):5731-5737, 1998.
Morrell, *Adv. Exp. Med. Biol.*, 661:251-264, 2010.
Morrison et al., *J. Gen. Virol.*, 78(Pt 4):873-878, 1997.
Muesing et al., *Cell*, 48:691, 1987.
Naeije and Barbera, *Crit. Care*, 5:286-289, 2001.
Nahle et al., *Nat. Cell Biol.*, 4:859-864, 2002.
Naldini et al., *Proc. Natl. Acad. Sci. USA*, 93(21):11382-11388, 1996.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987
Nisbet et al., *Am. J. Respir. Cell Mol. Biol.*, 42:482-490, 2010.
Nomoto et al., *Gene*, 236(2):259-271, 1999.
Ohara et al., *Proc. Natl. Acad. Sci. USA*, 86:5673-5677, 1989.
Omirulleh et al., *Plant Mol. Biol.*, 21(3):415-28, 1993.
Ondek et al., *EMBO J.*, 6:1017, 1987.
Ornitz et al., *Mol. Cell. Biol.*, 7:3466, 1987.
Owens, *Novartis Found. Symp.*, 283:174-191, 2007.
Palmiter et al., *Nature*, 300:611, 1982.
Papandreou and Nanus, *J. Pediatr. Hematol. Oncol.*, 32:2-3, 2010.
Park et al., *Respirology*, 14:27-38, 2009.
Parks et al., *J. Virol.*, 71(4):3293-8, 1997.
Pease et al., *Proc. Natl. Acad. Sci. USA*, 91:5022-5026, 1994.
Pech et al., *Mol. Cell. Biol.*, 9:396, 1989.
Peinado et al., *Chest*, 134:808-814, 2008.
Pelletier and Sonenberg, *Nature*, 334:320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Perros et al., *Am. J. Respir. Crit. Care Med.*, 178:81-88, 2008.
Petkov et al., *J. Clin. Invest.*, 111(9):1339-1346, 2003.
Petrof, *Eur. Respir. J.*, 11(2):492-497, 1998.
Pfaffl, *Nucleic Acids Res.*, 29:e45, 2001.
Picard and Schaffner, *Nature*, 307:83, 1984.
Pignon J et al., *Hum. Mutat.*, 3(2):126-132, 1994.
Pinkert et al., *Genes and Dev.*, 1:268, 1987.
Platek et al., *Exp. Cell Res.*, 313:1090-1105, 2007.
Polyak et al., *Genes Dev.*, 10:1945-1952, 1996.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Preston, *Antioxid. Redox. Signal*, 9:711-721, 2007.
Queen and Baltimore, *Cell*, 35:741, 1983.
Quinn et al., *Mol. Cell. Biol.*, 9:4713, 1989.
Rabinovitch et al., *Diabetes*, 48(6):1223-1229, 1999.
Rabinovitch, *J. Clin. Invest.*, 118:2372-2379, 2008.
Reddy et al., *J. Virol.*, 72(2):1394-1402, 1998.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.

Remington's Pharmaceutical Sciences 15th Edition, 33:624-652, 1990
Resendez Jr. et al., *Mol. Cell. Biol.,* 8:4579, 1988.
Rhodes et al., *Methods Mol. Biol.,* 55:121-131, 1995.
Ripe et al., *Mol. Cell. Biol.,* 9:2224, 1989.
Rippe et al., "DNA-mediated gene transfer into adult rat hepatocytes in primary culture," *Mol. Cell Biol.,* 10:689-695, 1990.
Rittling et al., *Nuc. Acids Res.,* 17:1619, 1989.
Robbins and Ghivizzani, *Pharmacol. Ther.,* 80(1):35-47, 1998.
Robbins et al., *Proc. Natl. Acad. Sci. USA,* 95(17):10182-10187 1998.
Robbins et al., *Trends Biotechnol.,* 16(1):35-40, 1998.
Rosen et al., *Cell,* 41:813, 1988.
Said et al., *Circulation,* 115(10):1260-1268, 2007.
Said et al., *Eur. Respir. J,* 35(4):730-734, 2010.
Said, *Ann. NY Acad. Sci.,* 1144:148-153, 2008.
Sakai et al., *Genes and Dev.,* 2:1144, 1988.
Sambrook et al., In: *Molecular Cloning: A Laboratory Manual,* Vol. 1, Cold Spring Harbor Laboratory Press, Cold Spring Harbor, N.Y., Ch. 7, 7.19-17.29, 1989.
Santos et al., *Eur. Respir. J,* 19:632-638, 2002.
Sarver et al., *Science,* 247:1222-1225, 1990.
Satake et al., *J. Virology,* 62:970, 1988.
Sawai et al., *Mol. Genet. Metab.,* 67(1):36-42, 1999.
Scanlon et al., *Proc. Natl. Acad. Sci. USA,* 88:10591-10595, 1991.
Schaffner et al., *J. Mol. Biol.,* 201:81, 1988.
Scharf et al., *Am. J. Respir. Crit. Care Med.,* 166:314-322, 2002.
Scholzen et al., *J. Immunol.,* 166:1285-1291, 2001.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Shinall et al., *Biochemistry,* 44:15345-15350, 2005.
Shipp et al., *Nature,* 347:394-396, 1990.
Shipp et al., *Proc. Nat'l. Acad. Sci. USA* 85: 4819-4923, 1988
Shoemaker et al., *Nature Genetics,* 14:450-456, 1996.
Sirvent et al., *Oncogene,* 27:3494-3500, 2008.
Sleigh and Lockett, *J. EMBO,* 4:3831, 1985.
Smith, *Arch. Neurol.,* 55(8):1061-1064, 1998.
Spalholz et al., *Cell,* 42:183, 1985.
Spandau and Lee, *J. Virology,* 62:427, 1988.
Spandidos and Wilkie, *EMBO J.,* 2:1193, 1983.
Stambolic et al., *Mol. Cell,* 8:317-325, 2001.
Steck et al., *Nat. Genet.,* 15:356-362, 1997.
Stein et al., *J. Biol. Chem.,* 279:48930-48940, 2004.
Steiner, *Chest,* 136:658-659, 2009.
Stephens and Hentschel, *Biochem. J,* 248:1, 1987.
Stewart and Young, "Solid Phase Peptide Synthesis", 2d. ed., Pierce Chemical Co., 1984.
Stewart et al., *Gene Ther.,* 6(3):350-363, 1999.
Stuart et al., *Nature,* 317:828, 1985.
Sturiale et al., *Proc. Natl. Acad. Sci. USA,* 96:11653-11658, 1999.
Sullivan and Peterlin, *Mol. Cell. Biol.,* 7:3315, 1987.
Sultana et al., *Methods Mol. Biol.,* 519:351-361, 2009.
Sumitomo et al., *Biochim. Biophys. Acta,* 1751:52-59, 2005.
Sumitomo et al., *Cancer Cell,* 5:67-78, 2004.
Sunday et al., *Clin. Invest.,* 90:2517-2525, 1992.
Suzuki et al., *Biochem. Biophys. Res. Commun.,* 252(3):686-690, 1998.
Swartzendruber and Lehman, *J. Cell. Physiology,* 85:179, 1975.
Taiwo, *Spectroscopy,* 22:491-498, 2008.
Takebe et al., *Mol. Cell. Biol.,* 8:466, 1988.
Tam et al., *J. Am. Chem. Soc.,* 105:6442, 1983.
Tanaka et al., *Oncogene,* 8:2253-2258, 1993.
Taniura et al., *J. Biol. Chem.,* 274:16242-16248, 1999.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor and Stark, *Oncogene,* 20:1803-1815, 2001.
Taylor et al., *J. Biol. Chem.,* 264:15160, 1989.
Thabut et al., *Chest,* 127:1531-1536, 2005.
Thiesen et al., *J. Virology,* 62:614, 1988.
Timiryasova et al., *Int. J. Oncol.,* 14(5):845-854, 1999.
Timiryasova et al., *Oncol. Res.;* 11(3):133-144, 1999.
Treisman, *Cell,* 42:889, 1985.
Tronche et al., *Mol. Biol. Med,* 7:173, 1990.
Trudel and Constantini, *Genes and Dev.,* 6:954, 1987.
Tsukada et al., *Plant Cell Physiol.,* 30(4) 599-604, 1989.
Tsumaki et al., *J. Biol. Chem.,* 273(36):22861-22864, 1998.
Tur-Kaspa et al., *Mol. Cell. Biol.,* 6:716-718, 1986.
Turner, *Biochem. Soc. Trans.,* 31:723-727, 2003.
Tyndell et al., *Nuc. Acids. Res.,* 9:6231, 1981.
Ulrich et al., *Respiration,* 79:288-295, 2010.
van der Velden and Hulsmann, *Clin. Exp. Allergy,* 29:445-456, 1999.
Vanderkwaak et al., *Gynecol. Oncol.,* 74(2):227-234, 1999.
Vannice and Levinson, *J. Virology,* 62:1305, 1988.
Vasseur et al., *Proc Natl. Acad. Sci. USA,* 77:1068, 1980.
Vogelstein et al., *Nature,* 408(6810):307-310, 2000.
Vogelstein, *Nature,* 348(6303):681-682, 1990.
Vousden and Lu, *Nat. Rev. Cancer,* 2:594-604, 2002.
Vousden and Prives, *Cell,* 120:7-10, 2005.
Wagner et al., *Science,* 260:1510-1513, 1990.
Walker et al., *Nucleic Acids Res.,* 20(7):1691-1696, 1992.
Wang and Calame, *Cell,* 47:241, 1986.
Wang et al., *Biochem. Biophys. Res. Commun.,* 310:236-241, 2003.
Wang et al., *Gynecol. Oncol.,* 71(2):278-287, 1998.
Weber et al., *Cell,* 36:983, 1984.
Weihl et al., *Neurosurgery,* 44(2):239-252, 1999.
Weinberg et al., *Biochemistry,* 28:8263-8269, 1989.
Weinberger et al., *Mol. Cell. Biol.,* 8:988, 1984.
Weitzenblum et al., *Semin. Respir. Crit. Care Med.,* 30:458-470, 2009.
White et al., *J Virol.,* 73(4):2832-28340, 1999.
Wick et al., *Am. J. Respir. Crit. Care Med.,* 175:A44, 2007.
Wick et al., *Am. J. Respir. Crit. Care Med.,* 181:A3952, 2010.
Wick et al., *FASEB J.,* 23:770, 2009.
Wilson, *J. Clin. Invest.,* 98(11):2435, 1996.
Winoto and Baltimore, *Cell,* 59:649, 1989.
Wong et al., *Gene,* 10:87-94, 1980.
Wu and Wallace, *Genomics,* 4:560-569, 1989.
Wu and Wu, *J. Biol. Chem.,* 262:4429-4432, 1987.
Wu et al., *Biochem. Biophys. Res. Commun.,* 233(1):221-226, 1997.
Wu, *Chung Hua Min Kuo Hsiao Erh Ko I Hsueh Hui Tsa Chih,* 39(5):297-300, 1998.
Yamada et al., *Proc. Natl. Acad. Sci. USA,* 96(7):4078-4083, 1999.
Yang and Liang, *Mol. Biotechnol.,* 3:197-208, 2004.
Yeung et al., *Gene Ther.,* 6(9):1536-1544, 1999.
Yoon et al., *J. Gastrointest. Surg.,* 3(1):34-48, 1999.
Yu and Zhang, *Biochem. Biophys. Res. Commun.,* 331:851-858, 2005.
Yu et al., *Proc. Natl. Acad. Sci. USA,* 100:1931-1936, 2003.
Yu et al., *Proc. Natl. Acad. Sci. USA,* 96:14517-14522, 1999.
Yutzey et al., *Mol. Cell. Biol.,* 9:1397, 1989.
Zhao-Emonet et al., *Biochim. Biophys. Acta,* 1442(2-3):109-119, 1998.
Zheng et al., *J. Gen. Virol.,* 80(Pt 7):1735-1742, 1999.
Zhou et al., *Exp. Hematol,* 21:928-933, 1993.
Zufferey et al., *Nat. Biotechnol.,* 15(9):871-875, 1997.

What is claimed is:

1. A method for treating a subject with pulmonary vascular remodeling comprising administering to said subject a agent selected from (a) neprilysin, (b) an enzymatically active fragment of neprilysin comprising an intact peptidase domain, (c) an expression cassette comprising a polynucleotide encoding a neprilysin polypeptide or an enzymatically active fragment of neprilysin comprising an intact peptidase domain under the control of a promoter operable in eukaryotic cells.

2. The method of claim 1, wherein said subject is administered an expression cassette comprising a polynucleotide encoding a neprilysin polypeptide under the control of a promoter operable in eukaryotic cells.

3. The method of claim 2, wherein said promoter is heterologous to the polynucleotide sequence.

4. The method of claim 3, wherein said promoter is selected from the group consisting of hsp68, SV40, CMV, MKC, GAL4$_{UAS}$, HSV and β-actin.

5. The method of claim 2, wherein said expression cassette is contained in a viral vector.

6. The method of claim 2, wherein said expression cassette is contained in a non-viral vector.

7. The method of claim 6, wherein said non-viral vector is comprised within a lipid formulation.

8. The method of claim 2, wherein said expression cassette further comprises a polyadenylation signal.

9. The method of claim 1, wherein said subject is administered neprilysin or an enzymatically active fragment of neprilysin that comprises an intact peptidase domain.

10. The method of claim 1, wherein said agent is administered orally, intravenously, intraarterially, subcutaneously, transdermally or by inhalation.

11. The method of claim 1, wherein said subject is a human.

12. The method of claim 1, wherein said subject is or was a smoker.

13. The method of claim 1, wherein said subject has emphysema.

14. The method of claim 1, wherein said subject is administered a second therapy.

15. The method of claim 1, wherein said subject has pulmonary arterial hypertension (Group 1 PAH), pulmonary veno-occlusive disease (PVOD) and pulmonary capillary hemangiomatosis (PCH) (Group 1'), pulmonary hypertension due to left heart disease (Group 2 PH), pulmonary hypertension due to lung disease and/or hypoxia (Group 3), chronic thromboembolic pulmonary hypertension (Group 4), pulmonary hypertension with unclear or multifactorial etiologies (Group 5), idiopathic forms of pulmonary vascular disease, or a lung disorder that including any form of acute and chronic lung injury and inflammation (ARDS, ILD, pneumonia, COPD, asthma), or primary lung vascular disorders (idiopathic, collagen vascular associated, liver disease associated, drug-associated, HIV-associated, blood clot-induced pulmonary hypertension).

* * * * *